US012644895B2

(12) United States Patent
Remaley et al.

(10) Patent No.: US 12,644,895 B2
(45) Date of Patent: Jun. 2, 2026

---

(54) METHODS FOR ASSESSING CARDIOVASCULAR DISEASE OR INFLAMMATORY DISEASE RISK USING NON-EXCHANGEABLE LIPID PROBE

(71) Applicant: The United States of America, as represented by the Secretary, Department of Health and Human Services, Bethesda, MD (US)

(72) Inventors: Alan T. Remaley, Bethesda, MD (US); Edward B. Neufeld, Washington, DC (US); Masaki Sato, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1029 days.

(21) Appl. No.: 17/437,094

(22) PCT Filed: Mar. 6, 2020

(86) PCT No.: PCT/US2020/021494
§ 371 (c)(1),
(2) Date: Sep. 8, 2021

(87) PCT Pub. No.: WO2020/185598
PCT Pub. Date: Sep. 17, 2020

(65) Prior Publication Data
US 2022/0178953 A1      Jun. 9, 2022

Related U.S. Application Data

(60) Provisional application No. 62/844,957, filed on May 8, 2019, provisional application No. 62/815,604, filed on Mar. 8, 2019.

(51) Int. Cl.
| | |
|---|---|
| *G01N 33/92* | (2006.01) |
| *G01N 30/02* | (2006.01) |
| *G01N 30/74* | (2006.01) |
| *G01N 33/543* | (2006.01) |

(52) U.S. Cl.
CPC ............. *G01N 33/92* (2013.01); *G01N 30/74* (2013.01); *G01N 33/54313* (2013.01); *G01N 2030/027* (2013.01); *G01N 2333/775* (2013.01); *G01N 2800/32* (2013.01); *G01N 2800/50* (2013.01)

(58) Field of Classification Search
None
See application file for complete search history.

(56) References Cited

U.S. PATENT DOCUMENTS

| | | | | |
|---|---|---|---|---|
| 7,250,304 | B2 * | 7/2007 | Fogelman | .............. G01N 33/92 |
| | | | | 435/11 |
| 2010/0179066 | A1 | 7/2010 | Chapman et al. | |
| 2015/0316566 | A1 | 11/2015 | Dasseux et al. | |
| 2016/0274134 | A1 | 9/2016 | Mutharasan et al. | |
| 2017/0016924 | A1 | 1/2017 | Heinecke et al. | |
| 2018/0074080 | A1 * | 3/2018 | Thaxton | .................... A61P 9/10 |

OTHER PUBLICATIONS

Chazotte Cold Spring Harb Protoc. May 1, 2011;2011(5):pdb. prot5621. doi: 10.1101/pdb.prot5621 (Year: 2011).*
Mitra and Dungan, "Micellar properties of quillaja saponin. 2. Effect of solubilized cholesterol on solution properties" Colloids and Surfaces B: Biointerfaces vol. 17, Issue 2, Feb. 15, 2000, pp. 117-133. Available online Dec. 6, 1999. (Year: 1999).*
Doonan et al. "Cholesterol Efflux Capacity, Carotid Atherosclerosis, and Cerebrovascular Symptomatology" Atherosclerosis, Thrombosis and Vascular Biology. vol. 34, No. 4 https://doi.org/10.1161/ATVBAHA.113.302590. Published Feb. 20, 2014 (Year: 2014).*
Davidson et al. J Lipid Res. Apr. 2016;57(4):674-686. doi: 10.1194/jlr.M066613 (Year: 2016).*
Weibel et al. Arterioscler Thromb Vasc Biol. 2014;34:17-25 (Year: 2014).*
Horiuchi et al. Bioscience Reports (2019) 39 BSR20190213 https://doi.org/10.1042/BSR20190213 (Version of Record published: Apr. 2, 2019) (Year: 2019).*
Asztalos et al., "Metabolic and functional relevance of HDL subspecies," Curr Opin Lipidol., 22(3): 176-185 (Jun. 2011).
Brewer et al., "Isolation and characterization of apolipoproteins A-I, A-II, and A-IV," Methods Enzymol, 128: 223-246 (1986).
Chen et al., "Reconstituted HDL elicits marked changes in plasma lipids following single-dose injection in C57Bl/6 mice," J Cardiovasc Pharmacol Ther., 17(3): 315-323 (Sep. 2012), published online Nov. 8, 2011.

(Continued)

*Primary Examiner* — Gregory S Emch
*Assistant Examiner* — Fernando Ivich
(74) *Attorney, Agent, or Firm* — Leydig, Voit & Mayer, Ltd.

(57) ABSTRACT

A method of assessing the risk for development of cardiovascular disease (CVD) or an inflammatory disease in a patient comprises (i) incubating a sample of body fluid with donor particles, wherein the donor particles are coated with a lipid and a first quantity of detectably labeled, non-exchangeable lipid probe (NELP); (ii) separating the detectably labeled NELP-associated HDL into a first portion and the donor particles into a second portion; (iii) measuring the second quantity of detectably labeled NELP in the first portion; (iv) determining a detectably labeled NELP efflux value for the patient; and (v) comparing the detectably labeled NELP efflux value for the patient to a reference standard. Related methods of lowering the risk for development of CVD or an inflammatory disease in a patient and methods of measuring the quantity of functional HDL in a sample of body fluid are also provided.

23 Claims, 45 Drawing Sheets

(56) References Cited

OTHER PUBLICATIONS

Freeman et al., "Plasma lipoprotein-X quantification on filipin-stained gels: monitoring recombinant LCAT treatment ex vivo," *J Lipid Res.*, 60(5): 1050-1057 (May 2019), published online Feb. 26, 2019.

O et al., "Role of lecithin: cholesterol acyltransferase and apolipoprotein A-I in cholesterol esterification in lipoprotein-X in vitro," *J Lipid Res.*, 36(11): 2344-2354 (Nov. 1995).

Gordon et al., "High density lipoprotein proteome is associated with cardiovascular risk factors and atherosclerosis burden as evaluated by coronary CT angiography," *Atherosclerosis*, 278: 278-285 (Nov. 2018), published online Sep. 25, 2018, Author manuscript as published in PubMed.

Gordon et al., "Proteomic characterization of human plasma high density lipoprotein fractionated by gel filtration chromatography," *J Proteome Res.*, 9(10): 5239-5249 (Oct. 2010), Author manuscript as published in PubMed.

Harada et al., "Cholesterol uptake capacity: a new measure of HDL functionality for coronary risk assessment," *J Appl Lab Med.*, 2(2): 186-200 (Sep. 2017).

International Searching Authority, International Preliminary Report on Patentability in International Patent Application No. PCT/US2020/021494, 7 pp. (Aug. 25, 2021).

International Searching Authority, International Search Report in International Patent Application No. PCT/US2020/021494, 4 pp. (Jun. 12, 2020).

International Searching Authority, Written Opinion in International Patent Application No. PCT/US2020/021494, 8 pp. (Jun. 12, 2020).

Khera et al., "Cholesterol efflux capacity, high-density lipoprotein function, and atherosclerosis," *N Engl J Med.*, 364(2): 127-135 (Jan. 2011).

Lambert et al., "Analysis of glomerulosclerosis and atherosclerosis in lecithin cholesterol acyltransferase-deficient mice," *J Biol Chem*, 276(18): 15090-15098 (May 2001), published online Feb. 7, 2001.

Lerch et al., "Production and characterization of a reconstituted high density lipoprotein for therapeutic applications," *Vox Sang*, 71(3): 155-164 (1996).

Neufeld et al., "ApoA-I-mediated lipoprotein remodeling monitored with a fluorescent phospholipid," *Biology*, 8(3), 26 pp. (Jul. 12, 2019).

Neufeld et al., "Cell-Free HDL-Specific Phospholipid Efflux Predicts Plaque Burden and Coronary Artery Disease," *Circulation Journal of the American Heart Association*, 2019; 140: A13642 (Nov. 11, 2019), 1 p.

Neufeld et al., "Lipoprotein Remodeling and Cholesterol Exchange Monitored Using Fluorescent Lipids and Proteins," *Arteriosclerosis Thrombosis and Vascular Biology*, 2017; 37(Supplement 1): A556 (Aug. 2017), 1 p.

Neufeld et al., "The ABCA1 transporter modulates late endocytic trafficking: insights from the correction of the genetic defect in Tangier disease," *J Biol Chem*, 279(15): 15571-15578 (Apr. 2004), published online Jan. 27, 2004.

Ossoli et al., "Lipoprotein X causes renal disease in LCAT deficiency," *PLoS One*, 11(2): e0150083 (Feb. 2016), 26 pp.

Rosenson et al., "Cholesterol efflux and atheroprotection: advancing the concept of reverse cholesterol transport," *Circulation*, 125(15): 1905-1919 (Apr. 2012).

Rousset et al., "Effect of recombinant human lecithin cholesterol acyltransferase infusion on lipoprotein metabolism in mice," *J Pharmacol Exp Ther*, 335(1): 140-148 (Oct. 2010), published online Jul. 6, 2010.

Rubin et al., "Expression of human apolipoprotein A-I in transgenic mice results in reduced plasma levels of murine apolipoprotein A-I and the appearance of two new high density lipoprotein size subclasses," *Proc Natl Acad Sci USA*, 88(2): 434-438 (Jan. 1991).

Sakai et al., "Targeted disruption of the mouse lecithin: cholesterol acyltransferase (LCAT) gene. Generation of a new animal model for human LCAT deficiency," *J Biol Chem*, 272(11): 7506-7510 (Mar. 1997).

Vaisman et al., "Overexpression of human lecithin cholesterol acyltransferase leads to hyperalphalipoproteinemia in transgenic mice," *J Biol Chem*, 270(20): 12269-12275 (May 1995).

Wessel et al., "A method for quantitative recovery of a protein in dilute solution in the presence of detergents and lipids," *Anal Biochem*, 138(1): 141-143 (Apr. 1984).

Neufeld et al., "Lipoprotein Remodeling and Cholesterol Exchange Monitored Using Fluorescent Lipids and Proteins," Poster presented based on the abstract of *Arteriosclerosis Thrombosis and Vascular Biology*, 2017; 37(Supplement 1): A556 (Aug. 2017), 18 pgs.

Willem Kok et al., "A non-exchangeable fluorescent phospholipid analog as a membrane traffic marker of the endocytic pathway," *European Journal of Cell Biology* 53(1):173-184 (Oct. 1990).

Horiuchi et al., "Validation and application of a novel cholesterol efflux assay using immobilized liposomes as a substitute for cultured cells," *Bioscience Reports*, 38(2): BSR20180144 (Apr. 2018), 10 pp.

European Patent Office, Extended European Search Report dated Oct. 31, 2022, European Patent Application No. 20769307.8, 11 pages.

* cited by examiner $R^2 = 0.8534$
$p < 0.0001$

FC Normalized Pixel Intensity

PE Normalized Pixel Intensity

Fig. 15B $Y = 0.38X + 0.45$ r = 0.68
$P = 7.3 \times 10^{-13}$

Normalized HDL-SPE

Normalized *PE HDL pixel Intensity

METHODS FOR ASSESSING CARDIOVASCULAR DISEASE OR INFLAMMATORY DISEASE RISK USING NON-EXCHANGEABLE LIPID PROBE

CROSS-REFERENCE TO RELATED APPLICATIONS

This patent application is a U.S. National Phase of International Patent Application No. PCT/US2020/021494, filed Mar. 6, 2020, which claims the benefit of U.S. Provisional Patent Application No. 62/815,604, filed Mar. 8, 2019, and U.S. Provisional Patent Application No. 62/844,957, filed May 8, 2019, each of which is incorporated by reference herein in its entirety.

STATEMENT REGARDING FEDERALLY SPONSORED RESEARCH OR DEVELOPMENT

This invention was made with Government support under project number HL002058 by the National Institutes of Health, National Heart, Lung, and Blood Institute. The Government has certain rights in the invention.

BACKGROUND OF THE INVENTION

Cardiovascular disease (CVD) is a leading cause of death for people of most racial/ethnic groups in the United States. Effective treatment and/or prevention of CVD may be facilitated by early and reliable evaluation of a patient's risk for developing CVD. Accordingly, there is a need for improved methods of assessing the risk for development of CVD in a patient.

BRIEF SUMMARY OF THE INVENTION

An embodiment of the invention provides a method of assessing the risk for development of a disease in a patient, the method comprising: (i) incubating a sample of body fluid from the patient with donor particles, wherein the donor particles are coated with a lipid and a first quantity of a detectably labeled, non-exchangeable lipid probe (NELP) prior to incubating the donor particles with the sample, wherein the detectably labeled NELP is effluxed by HDL, wherein the body fluid comprises high density lipoprotein (HDL) and apolipoprotein A-I (apoA-I), wherein the apoA-I specifically transfers at least a portion of the detectably labeled NELP from the donor particles to the HDL to produce detectably labeled NELP-associated HDL having a second quantity of detectably labeled NELP; (ii) separating the detectably labeled NELP-associated HDL into a first portion and the donor particles into a second portion; (iii) measuring the second quantity of detectably labeled NELP in the first portion; (iv) determining a detectably labeled NELP efflux value for the patient, wherein the detectably labeled NELP efflux value for the patient equals the second quantity of detectably labeled NELP divided by the first quantity of detectably labeled NELP; and (v) comparing the detectably labeled NELP efflux value for the patient to a reference standard, wherein the reference standard is the detectably labeled NELP efflux value of control human body fluid sample(s) determined by carrying out (i)-(iv) using the control human body fluid sample(s) in place of the sample of body fluid from the patient; wherein a detectably labeled NELP efflux value for the patient that is equal to or higher than the reference standard is indicative of a lower risk for development of the disease in the patient, wherein a detectably labeled NELP efflux value for the patient that is lower than the reference standard is indicative of a higher risk for development of the disease in the patient, and wherein the disease is an inflammatory disease or CVD.

Another embodiment of the invention provides a method of measuring the quantity of functional HDL in a sample of body fluid from a patient, the method comprising: (i) incubating a sample of body fluid from the patient with donor particles, wherein the donor particles are coated with a lipid and a first quantity of a detectably labeled NELP prior to incubating the donor particles with the sample, wherein the detectably labeled NELP is effluxed by HDL, wherein the body fluid comprises HDL and apoA-I, wherein the apoA-I specifically transfers at least a portion of the detectably labeled NELP from the donor particles to the HDL to produce detectably labeled NELP-associated HDL having a second quantity of detectably labeled NELP; (ii) separating the detectably labeled NELP-associated HDL into a first portion and the donor particles into a second portion; (iii) measuring the second quantity of detectably labeled NELP in the first portion; and (iv) determining a detectably labeled NELP efflux value for the patient, wherein the detectably labeled NELP efflux value for the patient equals the second quantity of detectably labeled NELP divided by the first quantity of detectably labeled NELP, wherein the detectably labeled NELP efflux value is indicative of the quantity of functional HDL in the sample of body fluid from the patient, wherein the method does not comprise separating HDL from LDL or VLDL.

Still another embodiment of the invention provides a method of lowering the risk for development of a disease in a patient, the method comprising: receiving an identification of the patient as having higher risk for development of the disease, wherein the risk for development of the disease has been assessed by any of the inventive methods described herein; and (i) administering one or both of a lipoprotein-modifying drug and an anti-inflammatory drug to the patient identified as having the higher risk for development of the disease and/or (ii) recommending lifestyle changes to the patient identified as having the higher risk for development of the disease, wherein the disease is CVD or an inflammatory disease.

BRIEF DESCRIPTION OF THE SEVERAL VIEWS OF THE DRAWINGS

FIG. 11C is a graph showing that only *PE fluorescence is detected in the supernatant of plasma (P) incubated with either *PE-labeled or dually *PE/*Chol-labeled LC-CSH when *PE fluorescence is monitored.

FIG. 11D is a graph showing that only *Chol fluorescence is detected in the supernatant of plasma incubated with either *Chol-labeled or dually *PE/*Chol-labeled LC-CSH when *Chol fluorescence is monitored.

FIG. 12A is a graph showing effect of pooled normal human plasma (HP) volume on fluorescent lipid efflux. All data are mean±SD in triplicate assays.

FIG. 15B is a graph showing that normalized HDL-SPE and normalized *PE HDL pixel intensity were highly and significantly correlated. Supernatant *PE represents *PE HDL.

FIG. 17A is a graph showing receiver operating characteristic (ROC) curves for HDL-SPE and C-CEC. Area under the curve (AUC) of receiver operating characteristic (ROC) curve constructed for HDL-SPE was 0.67 (p=0.007) and C-CEC was 0.53 (p=0.67).

FIG. 18C is a graph showing receiver operating characteristic (ROC) curves for HDL-SPE and HDL-C.

DETAILED DESCRIPTION OF THE INVENTION

Figure 1A:
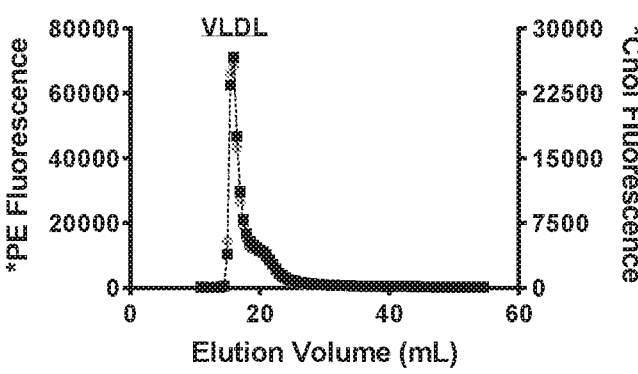
FIG. 1A is a graph showing the incorporation of fluorescent PE and cholesterol into human plasma lipoprotein VLDL. An FPLC analysis of fluorescent PE and cholesterol dual-labeled isolated human lipoprotein VLDL was carried out. Black squares: PE fluorescence; Gray circles: Cholesterol fluorescence.

An embodiment of the invention provides a method of assessing the risk for development of a disease in a patient. The inventive methods may provide any one or more of a variety of advantages. For example, the inventive methods may, advantageously, assess disease risk by assessing the ability of apoA-I and other HDL-associated lipids to remove phospholipid from fatty arterial lesions. Accordingly, the inventive methods advantageously assess disease risk based on HDL functionality in whole human plasma. Without being bound to a particular theory or mechanism, it is believed that the active removal of non-exchangeable lipids, e.g., phospholipids, from membranous structures in cardiovascular atherosclerotic lesions by functional apoA-I, a transferable protein residing on HDL, plays a role in the prevention and regression of CVD.

HDL has two basic structures: pre-β discoidal HDL and alpha spherical shaped HDL. Pre-β discoidal HDL contains two apoA-I molecules, phospholipids and cholesterol. Pre-β discoidal HDL is the nascent particle formed when apoA-I solubilizes phospholipids and cholesterol from cell membranes. Pre-β discoidal HDL removes cholesterol from lipid-laden macrophages that reside in fatty plaques in the wall of arteries, which is the initial step in the reverse cholesterol transport pathway.

Alpha spherical shaped HDL has a surface monolayer of phospholipids, cholesterol and other lipids along with over 80 different proteins. Each individual alpha spherical shaped HDL particle only contains a subset of a few proteins. The alpha spherical shaped HDL particle contains esterified cholesterol and some triglyceride in its core. These alpha spherical shaped HDL particles deliver cholesterol ester and triglycerides to the liver for elimination from the body by the reverse cholesterol pathway. Because apoA-I is an exchangeable protein, it can dissociate from an alpha spherical shaped HDL particle, and then bind to a cell membrane to solubilize lipids to form a new pre-β discoidal HDL particle.

The reverse cholesterol transport pathway refers to the removal of cholesterol from fatty lesions in the arterial wall and delivery of this cholesterol to the liver. The enzyme LCAT enlarges the HDL particles initially formed in the lesions and these large HDL particles then deliver cholesterol ester and triglycerides (HDL core lipids) to the liver for removal from the body in bile that is delivered to the gut. ApoA-I is synthesized in the liver and rapidly converted to pre-β discoidal HDL and small α4 HDL. The first step of reverse cholesterol transport is removal of cholesterol and phospholipids from macrophages in fatty lesions in the arterial wall by pre-β discoidal HDL and small α4 HDL. This is the step that the inventive methods advantageously assess: the ability of apoA-I and other HDL-associated lipids to remove phospholipid from fatty arterial lesions.

An embodiment of the invention provides a method of assessing the risk for development of a disease in a patient. The method may comprise incubating a sample of body fluid from the patient with donor particles. The body fluid may be any body fluid which may comprise HDL. Examples of body fluid include, but are not limited to, whole plasma, blood serum, urine and saliva. Urine and saliva are filtrates of plasma and may be possible sources of HDL that are more conveniently obtained from patients.

Whole plasma is the clear, straw-colored liquid portion of whole blood that remains after the platelets and blood cells are removed. The whole plasma comprises HDL and apoA-I (e.g., functional HDL and functional apoA-I), among other things. Whole plasma also contains water, enzymes, antibodies, glucose, clotting factors, electrolytes ($Na^+$, $Ca^{2+}$, $Mg^{2+}$, $HCO_3^-$, $Cl^-$, etc.), hormones, carbon dioxide, and oxygen. Whole plasma comprises other lipoproteins (including low density lipoprotein (LDL) and very low density lipoprotein (VLDL)) and other apolipoproteins. Whole plasma refers to plasma which has not been treated to remove HDL, LDL, or VLDL.

In an embodiment of the invention, the method does not comprise separating HDL from LDL or VLDL. In this regard, the method does not comprise pre-treating the body fluid to separate HDL from LDL or VLDL or separating HDL from LDL or VLDL by, e.g., electrophoresis or precipitation of non-HDL lipoproteins by polyethylene glycol (PEG) or any other treatment.

The donor particles may comprise a substrate composed of any of a variety of different materials. In an embodiment of the invention, the donor particle substrate comprises a lipid-binding particulate material. Examples of suitable donor particle substrates include, but are not limited to, calcium silicate hydrate, glass, plastic, latex, and magnetic material. For example, the donor particles may comprise calcium silicate hydrate crystals, glass beads, plastic beads, latex beads, or magnetic beads. In an embodiment of the invention, the donor particles are Lipid Removal Agent (LRA), which is a commercially available reagent composed of a substrate of calcium silicate hydrate crystals. LRA particles coated as described herein may, advantageously, be readily separated from HDL by centrifugation. The size (e.g., diameter) of the donor particles is not limited and may be, for example, less than about 1 micron, about 1 micron, about 10 microns, about 20 microns, about 40 microns, about 60 microns, about 80 microns, about 100 microns, or a range defined by any two of the foregoing values.

The donor particles are coated with a lipid and a detectably labeled, non-exchangeable lipid probe (NELP). The lipid may be any of a variety lipids. In an embodiment of the invention, the lipid is a phospholipid. The phospholipid may be any of a variety phospholipids. In an embodiment of the invention, the phospholipid is phosphatidylcholine. Phosphatidylcholine includes any of a variety of compounds including a mixture of stearic, palmitic, and oleic acid diglycerides linked to the choline ester of phosphoric acid. Examples of suitable phospholipids may include, but are not limited to, 1,2-dimyristoyl-sn-glycero-3-phosphocholine (DMPC) or a lecithin (e.g., egg lecithin or soy lecithin), dipalmitoyl phosphatidylcholine (DPPC), dipalmitoyl phosphatidylethanolamine (DPPE), distearoyl phosphatidylcholine (DSPC), dipalmitoyl phosphatidyl glycerol (DPPG), or any combination thereof. In a preferred embodiment, the phospholipid is DMPC.

In an embodiment of the invention, the method further comprises applying a sterol to the donor particles prior to incubating the donor particles with the sample. Although donor particles with phospholipid alone efflux fluorescent PE to plasma HDL, the addition of sterol may enhance efflux. The molar ratio of the lipid to the sterol coated on the donor particles may be about 4:1 to about 2:1. For example, the molar ratio of the lipid to the sterol coated on the donor particles may be from about 4:1, about 3:1, about 2:1, or a range defined by any two of the foregoing values.

The sterol may be any of a variety of sterols. Examples of suitable sterols include, but are not limited to, cholesterol, lathosterol, agnosterol, 7-dehydrocholesterol, cholecalciferol, desmosterol, lathosterol, cholestanol, coprastanol, campesterol, stigmasterol, sitosterol (e.g., β-sitosterol), avenasterol, stigmastenol, brassicasterol, 4-desmethyl sterols (i.e. with no substituent on carbon-4), 4α-monomethyl sterols and 4,4-dimethyl sterols, phytostanols (fully saturated), ergosterol, amyrin, cylcoartenol, or any combination thereof. In a preferred embodiment, the sterol is cholesterol.

The detectably labeled NELP may be any lipid that is effluxed by HDL. The detectably labeled NELP may be a lipid that will partition into a lipid membrane or surface. In an embodiment of the invention, the NELP may be a phospholipid, for example, any of the phospholipids described herein with respect to other aspects of the invention. Examples of suitable NELPs include, but are not limited to, phosphatidylethanolamine (PE), phosphatidylcholine, phosphatidylserine, sphingomyelin, glycolipids, or any combination thereof. In a preferred embodiment, the NELP is PE.

The NELP may be labeled with any detectable label. In an embodiment of the invention, the NELP comprises a radiolabel, a chemiluminescent label, or a fluorescent label. The detectable label may be placed on any location on the NELP provided that the location of the detectable label does not interfere with the specific transfer of the NELP from the donor particles to the HDL. In an embodiment of the invention, the NELP comprises a hydrophilic portion, a hydrophobic portion, and a detectable label positioned on hydrophilic portion.

The donor particles may be coated with a first quantity of detectably labeled NELP. During and/or after incubation of the donor particles with the body fluid sample, some or all of the detectably labeled NELP will be specifically transferred from the donor particles to the HDL from the body fluid, as explained in more detail below. The first quantity of detectably labeled NELP on the donor particles refers to the quantity of detectably labeled NELP on the donor particles prior to incubating the donor particles with the sample of body fluid.

The method may comprise mixing the body fluid with the donor particles. In this regard, the body fluid may be placed in physical contact with the donor particles so that the detectably labeled NELP can be specifically transferred from the donor particles to the HDL from the body fluid. The donor particles and the body fluid may be mixed in any suitable container, for example, multiwell plates (e.g., 96-well plates).

The method may comprise incubating the sample of body fluid from the patient with the donor particles. The incubation may be carried out at a temperature which does not disrupt the structure of the HDL or the apoA-I and which is suitable for facilitating the specific transfer of the detectably labeled NELP from the donor particles to the HDL. The incubation may be carried out at a temperature of from about 10° C. to about 90° C., from about 20° C. to about 80° C., from about 30° C. to about 70° C., or from about 35° C. to about 40° C. For example, the incubation may be carried out at a temperature of about 35° C., at about 36° C., at about 37° C., at about 38° C., at about 39° C., at about 40° C., or a range defined by any two of the foregoing values.

The incubation may be carried out for a duration suitable for facilitating the specific transfer of the detectably labeled NELP from the donor particles to the acceptor lipoprotein, namely HDL. The incubation may be carried out for a duration of from about 1 minute to about 24 hours, from about 20 minutes to about 18 hours, about 30 minutes to about 10 hours, about 40 minutes to about 8 hours, or about 50 minutes to about 6 hours. For example, the incubation may be carried out for a duration of about 30 minutes, 1 hour, 2 hours, 3 hours, 4 hours, 6 hours, or a range defined by any two of the foregoing values.

During and/or after the incubation, the apoA-I from the body fluid specifically transfers at least a portion of the detectably labeled NELP from the donor particles to the HDL to produce detectably labeled NELP-associated HDL having a second quantity of detectably labeled NELP. The second quantity of detectably labeled NELP is the quantity of detectably labeled NELP associated with the HDL after the body fluid is incubated with the donor particles and which has been specifically transferred from the donor particles to the HDL by apoA-I. The detectably labeled NELP transfers only to the HDL, in an apoA-I dependent manner. In contrast to the detectably labeled NELP, cholesterol transfers to all of HDL, LDL, and VLDL, as shown in the Examples.

The method may further comprise separating the detectably labeled NELP-associated HDL into a first portion and the donor particles into a second portion. The separating may be carried out in any of a variety of different ways. In an embodiment of the invention, the separating comprises centrifuging the detectably labeled NELP-associated HDL and the donor particles. When the separating is carried out by centrifugation, the first portion is a supernatant and the second portion is a pellet. The supernatant contains the detectably labeled NELP-associated HDL, and the pellet contains the donor particles. The centrifugation may be carried out at any speed and for any duration which does not disrupt the structure of the NELP-associated HDL. In an embodiment of the invention, the method comprises centrifuging the detectably labeled NELP-associated HDL and the donor particles at a speed of from about 100 to about 15,000 revolutions per minute (RPM), about 500 to about 1600 RPM, or about 1,000 to about 1,200 RPM. For example, the centrifugation may be carried out at a speed of about 100; about 500; about 1,000; about 1,500; about 2,000; about 3,000; about 4,000; about 5,000; about 6,000; about 7,000; about 8,000; about 9,000; about 10,000; about 11,000; about 12,000; about 13,000; about 14,000; about 15,000 RPM, or a range defined by any two of the foregoing values. In an embodiment of the invention, the method comprises centrifuging the detectably labeled NELP-associated HDL and the donor particles for a duration of from about 1 minute to about 60 minutes, about 2 minutes to about 45 minutes, about 3 minutes to about 30 minutes. For example, the centrifugation may be carried out for about 1, about 2, about 5, about 10, about 15, about 20, about 25, about 50, or about 60 minutes, or a range defined by any two of the foregoing values.

In an embodiment of the invention, the separating of the detectably labeled NELP-associated HDL from the donor particles is carried out by filtration. In this regard, the separating of the detectably labeled NELP-associated HDL into the first portion and the donor particles into the second portion comprises filtering the detectably labeled NELP-associated HDL from the donor particles.

In an embodiment wherein the donor particles are comprised of magnetic material, the separating of the detectably labeled NELP-associated HDL from the donor particles may be carried out using a magnet. The magnet will attract the donor particles into the second portion, leaving the detectably labeled NELP-associated HDL in a first portion.

The method may further comprise measuring the second quantity of detectably labeled NELP in the first portion. The second quantity of detectably labeled NELP is the quantity of detectably labeled NELP associated with the HDL after the body fluid is incubated with the donor particles and which has been specifically transferred from the donor particles to the HDL by apoA-I. The measurement of the quantity of detectably labeled NELP in the first portion represents the quantity of detectably labeled NELP-associated HDL in the first portion.

The measuring of the second quantity of detectably labeled NELP may be carried out in any of a variety of different ways and may be selected by the skilled person based on the type of detectable label chosen for the NELP. In an embodiment of the invention, when the detectably labeled PE is fluorescently labeled PE, the measuring of the quantity of the fluorescently labeled PE in the first portion is carried out by fluorometric measurement.

The method may further comprise determining a detectably labeled NELP efflux value for the patient. The detectably labeled NELP efflux value for the patient equals the second quantity of detectably labeled NELP divided by the first quantity of detectably labeled NELP.

The method may further comprise comparing the detectably labeled NELP efflux value for the patient to a reference standard. The reference standard may be the detectably labeled NELP efflux value of control human body fluid sample(s) determined by carrying out the same method as that which determined the detectably labeled NELP efflux value for the patient, but using the control human body fluid sample(s) in place of the sample of body fluid from the patient. The control human body fluid sample(s) may be the same type of body fluid as that of the patient. The control human body fluid sample(s) for the reference standard can be obtained from a single healthy donor or multiple healthy donors, wherein the healthy donor(s) is/are determined to be at a low or average risk of developing CVD as determined by, for example, the 2018 American College of Cardiology/ American Heart Association (AHA/ACC) Guidelines for assessing CVD risk based on a lipid panel that includes measuring the levels of one or more of total cholesterol, triglyceride, HDL-C, and LDL-C. A single sample of human body fluid from a single healthy donor may be used as a reference standard. A pool of human body fluid samples for the reference standard may be obtained from a single healthy donor or any number of different healthy donors, for example, about 10 to about 1,000 healthy donors.

The detectably labeled NELP efflux value for the patient (relative to the detectably labeled NELP efflux value for the control human body fluid sample(s)) is inversely correlated to the patient's risk for developing the disease. A detectably labeled NELP efflux value for the patient that is equal to or higher than the reference standard is indicative of a lower risk for development of the disease in the patient. A detectably labeled NELP efflux value for the patient that is lower than the reference standard is indicative of a higher risk for development of the disease in the patient. The disease may be CVD or an inflammatory disease. The CVD may be any of a variety of conditions which affect the cardiovascular system including, but not limited to, stroke, myocardial infarction, coronary artery disease (CAD), heart attack, arrhythmia, heart failure, congenital heart defects, cardiomyopathy, peripheral artery disease, angina, valve disease, high blood pressure, and inherited heart conditions.

The inflammatory disease may be any inflammatory disease, including, but not limited to asthma; lung fibrosis; bronchitis; respiratory infections; respiratory distress syndrome; obstructive pulmonary disease; allergic diseases; multiple sclerosis; infections of the brain or nervous system; dermatitis; psoriasis; burns; skin infections; gastroenteritis; colitis; Crohn's disease; cystic fibrosis; celiac disease; inflammatory bowel disease; intestinal infections; conjunctivitis; uveitis; infections of the eye; kidney infections; autoimmune kidney disease; diabetic nephropathy; cachexia; coronary restenosis; sinusitis, cystitis; urethritis; serositis; uremic pericarditis; cholecystis; vaginitis; drug reactions; hepatitis; pelvic inflammatory disease; lymphoma; multiple myeloma; vitiligo; alopecia; Addison's disease; Hashimoto's disease; Graves disease; atrophic gastritis/pernicious anemia; acquired hypogonadism/infertility; hypoparathyroidism; multiple sclerosis; Myasthenia gravis; Coombs positive hemolytic anemia; systemic lupus erthymatosis; Siogren's syndrome, and immune mediated (type-1) diabetes.

The inventive methods may, advantageously, also indicate relative levels of other clinical biomarkers of CVD. For example, the detectably labeled NELP efflux value for the patient (relative to the detectably labeled NELP efflux value for the control human body fluid sample(s)) may be significantly inversely correlated ($p<0.0001$) to clinical biomarkers of CVD. These biomarkers may include, but are not limited to, non-calcified plaque burden, total plaque burden, and fibrous fatty burden.

In an embodiment of the invention, a detectably labeled NELP efflux value for the patient that is equal to or higher than the reference standard is indicative of a lower non-calcified plaque burden in the patient. A detectably labeled NELP efflux value for the patient that is lower than the reference standard is indicative of a higher non-calcified plaque burden in the patient.

In another embodiment of the invention, a detectably labeled NELP efflux value for the patient that is equal to or higher than the reference standard is indicative of a lower total plaque burden in the patient. A detectably labeled NELP efflux value for the patient that is lower than the reference standard is indicative of a higher total plaque burden in the patient.

In an embodiment of the invention, a detectably labeled NELP efflux value for the patient that is equal to or higher than the reference standard is indicative of a lower fibrous fatty burden in the patient. A detectably labeled NELP efflux value for the patient that is lower than the reference standard is indicative of a higher fibrous fatty burden in the patient.

Another embodiment of the invention provides a method of lowering the risk for development of a disease in a patient. The method may comprise receiving an identification of the patient as having higher risk for development of the disease, wherein the risk for development of the disease has been assessed by the methods described herein with respect to other aspects of the invention. The method may further comprise administering a treatment to the patient identified as having the higher risk for development of the disease, wherein the treatment lowers the patient's risk for development of the disease. The treatment may comprise, but is not limited to, administering one or both of a lipoprotein-modifying drug and an anti-inflammatory drug. In an embodiment of the invention, the drug is a statin. Alternatively or additionally, the method comprises recommending lifestyle changes to the patient identified as having the higher risk for development of the disease. These lifestyle changes may include, but are not limited to, increasing exercise, reducing dietary intake of saturated fats, reducing dietary intake of trans fats, increasing dietary intake of omega-3 fatty acids, increasing dietary intake of soluble fiber, and increasing dietary intake of whey protein.

Still another embodiment of the invention provides a method of measuring the quantity of functional HDL in a sample of body fluid from a patient. The method may comprise incubating a sample of body fluid from the patient with donor particles. The body fluid, donor particles, and the incubating are as described herein with respect to other aspects of the invention. The method may further comprise separating the detectably labeled NELP-associated HDL into a first portion and the donor particles into a second portion and measuring the second quantity of detectably labeled NELP in the first portion, as described herein with respect to other aspects of the invention.

The method may further comprise determining a detectably labeled NELP efflux value for the patient, as described herein with respect to other aspects of the invention. The detectably labeled NELP efflux value for the patient equals the second quantity of detectably labeled NELP divided by the first quantity of detectably labeled NELP. The detectably labeled NELP efflux value is indicative of the quantity of functional HDL in the sample of body fluid from the patient.

In an embodiment of the invention, the method does not comprise separating HDL from LDL or VLDL. In this regard, the method does not comprise pre-treating the body fluid to separate HDL from LDL or VLDL or separating HDL from LDL or VLDL by, e.g., electrophoresis or precipitation of non-HDL lipoproteins by PEG or any other treatment.

The inventive methods may provide any one or more of a variety of advantages over conventional, cell-based assays that evaluate HDL function in CVD. These conventional, cell-based assays measure the acquisition of radiolabeled or fluorescently labeled cholesterol by HDL from labeled cells ("cholesterol efflux capacity assay" or "cell CEC assay," e.g., as described in Khera et al., *NEJM*, 364: 127-35 (2011)). In the cell CEC assay, the acquisition of cellular cholesterol by HDL occurs predominantly by passive exchange and reflects the capacity of the surface lipid monolayer on HDL to retain cholesterol. HDL for the cell CEC assay is isolated from body fluid by precipitating and then removing non-HDL lipoproteins from body fluid. The cell CEC assay requires days of preparation and evaluation to complete, and the coefficient of variation (CV) in the readout is relatively high (>10%).

In contrast to the cell CEC assay and other conventional assays, the methods are cell-free, rapid and require minimal equipment, reagents, and labor to carry out. In an embodiment of the invention, the method is carried out in less than about two hours, less than about one hour, less than about half an hour, or a range defined by any two of the foregoing values. Moreover, the inventive methods have a coefficient of variation (CV) of less than about 3%. The inventive methods are also automatable.

The following includes certain aspects of the invention.

1. A method of assessing the risk for development of a disease in a patient, the method comprising:

(i) incubating a sample of body fluid from the patient with donor particles, wherein the donor particles are coated with a lipid and a first quantity of a detectably labeled, non-exchangeable lipid probe (NELP) prior to incubating the donor particles with the sample, wherein the detectably labeled NELP is effluxed by HDL, wherein the body fluid comprises high density lipoprotein (HDL) and one or more HDL-associated protein(s) comprising apolipoprotein A-I (apoA-I), wherein the apoA-I specifically transfers at least a portion of the detectably labeled NELP from the donor particles to the HDL to produce detectably labeled NELP-associated HDL having a second quantity of detectably labeled NELP;

(ii) separating the detectably labeled NELP-associated HDL into a first portion and the donor particles into a second portion;

(iii) measuring the second quantity of detectably labeled NELP in the first portion;

(iv) determining a detectably labeled NELP efflux value for the patient, wherein the detectably labeled NELP efflux value for the patient equals the second quantity of detectably labeled NELP divided by the first quantity of detectably labeled NELP; and (v) comparing the detectably labeled NELP efflux value for the patient to a reference standard, wherein the reference standard is the detectably labeled NELP efflux value of control human body fluid sample(s) determined by carrying out (i)-(iv) using the control human body fluid sample(s) in place of the sample of body fluid from the patient;

wherein a detectably labeled NELP efflux value for the patient that is equal to or higher than the reference standard is indicative of a lower risk for development of the disease in the patient, wherein a detectably labeled NELP efflux value for the patient that is lower than the reference standard is indicative of a higher risk for development of the disease in the patient, and wherein the disease is an inflammatory disease or cardiovascular disease.

2. The method of aspect 1, wherein the disease is stroke, myocardial infarction, coronary artery disease (CAD), heart attack, arrhythmia, heart failure, congenital heart defects, cardiomyopathy, peripheral artery disease, angina, valve disease, high blood pressure, an inherited heart condition, or an inflammatory disease.

3. The method of aspect 1 or 2, wherein a detectably labeled NELP efflux value for the patient that is equal to or higher than the reference standard is indicative of a lower non-calcified plaque burden in the patient, and wherein a detectably labeled NELP efflux value for the patient that is lower than the reference standard is indicative of a higher non-calcified plaque burden in the patient.

4. The method of any one of aspects 1-3, wherein a detectably labeled NELP efflux value for the patient that is equal to or higher than the reference standard is indicative of a lower total plaque burden in the patient, and wherein a detectably labeled NELP efflux value for the patient that is lower than the reference standard is indicative of a higher total plaque burden in the patient.

5. The method of any one of aspects 1-4, wherein a detectably labeled NELP efflux value for the patient that is equal to or higher than the reference standard is indicative of a lower fibrous fatty burden in the patient, and wherein a detectably labeled NELP efflux value for the patient that is lower than the reference standard is indicative of a higher fibrous fatty burden in the patient.

6. A method of lowering the risk for development of a disease in a patient, the method comprising:

receiving an identification of the patient as having higher risk for development of the disease, wherein the risk for development of the disease has been assessed by the method of any one of aspects 1-5; and (i) administering one or both of a lipoprotein-modifying drug and an anti-inflammatory drug to the patient identified as having the higher risk for development of the disease and/or (ii) recommending lifestyle changes to the patient identified as having the higher risk for development of the disease, wherein the disease is an inflammatory disease or cardiovascular disease.

7. The method of any one of aspects 1-6, wherein the method does not comprise separating HDL from low density lipoprotein (LDL) or very low density lipoprotein (VLDL).

8. A method of measuring the quantity of functional high density lipoprotein (HDL) in a sample of body fluid from a patient, the method comprising:

(i) incubating a sample of body fluid from the patient with donor particles, wherein the donor particles are coated with a lipid and a first quantity of detectably labeled, non-exchangeable lipid probe (NELP) prior to incubating the donor particles with the sample, wherein the detectably labeled NELP is effluxed by HDL, wherein the body fluid comprises HDL and one or more HDL-associated protein(s) comprising apolipoprotein A-I (apoA-I), wherein the apoA-I specifically transfers at least a portion of the detectably labeled NELP from the donor particles to the HDL to produce detectably labeled NELP-associated HDL having a second quantity of detectably labeled NELP;

(ii) separating the detectably labeled NELP-associated HDL into a first portion and the donor particles into a second portion;

(iii) measuring the second quantity of detectably labeled NELP in the first portion; and (iv) determining a detectably labeled NELP efflux value for the patient, wherein the detectably labeled NELP efflux value for the patient equals the second quantity of detectably labeled NELP divided by the first quantity of detectably labeled NELP, wherein the detectably labeled NELP efflux value is indicative of the quantity of functional HDL in the sample of body fluid from the patient, wherein the method does not comprise separating HDL from LDL or VLDL.

9. The method of any one of aspects 1-8, wherein the lipid is a phosphatidylcholine.

10. The method of any one of aspects 1-9, wherein the donor particles comprise a lipid-binding particulate material.

11. The method of any one of aspects 1-10, further comprising applying a sterol to the donor particles prior to incubating the donor particles with the sample.

12. The method of aspect 11, wherein the molar ratio of the lipid to the sterol on the donor particles is from about 4:1 to about 2:1.

13. The method of aspect 11 or 12, wherein the sterol is cholesterol.

14. The method of any one of aspects 1-13, wherein the detectably labeled NELP comprises a hydrophilic portion, a hydrophobic portion, and a detectable label positioned on hydrophilic portion.

15. The method of any one of aspects 1-14, comprising incubating the sample of body fluid from the patient with the donor particles at a temperature of from about 10° C. to about 90° C.

16. The method of any one of aspects 1-15, comprising incubating the sample of body fluid from the patient with the donor particles for a period of from about 1 minute to about 24 hours.

17. The method of any one of aspects 1-16, wherein separating the detectably labeled NELP-associated HDL into the first portion and the donor particles into the second portion comprises centrifuging the detectably labeled NELP-associated HDL and the donor particles.

18. The method of aspect 17, comprising centrifuging the detectably labeled NELP-associated HDL and the donor particles at a speed of from about 100 to about 15,000 revolutions per minute (RPM).

19. The method of aspect 17 or 18, wherein the first portion is a supernatant and the second portion is a pellet.

20. The method of any one of aspects 1-16, wherein separating the detectably labeled NELP-associated HDL into the first portion and the donor particles into the second portion comprises filtering the detectably labeled NELP-associated HDL from the donor particles.

21. The method of any one of aspects 1-20, wherein the method is carried out in less than about two hours.

22. The method of any one of aspects 1-21, wherein the method is cell-free.

23. The method of any one of aspects 1-22, wherein the detectably labeled NELP comprises a radiolabel, a chemiluminescent label, or a fluorescent label.

24. The method of any one of aspects 1-23, wherein the lipid is 1,2-dimyristoyl-sn-glycero-3-phosphocholine (DMPC) or a lecithin.

25. The method of any one of aspects 1-24, wherein the non-exchangeable probe is phosphatidylethanolamine (PE).

It shall be noted that the preceding are merely examples of embodiments. Other exemplary embodiments are apparent from the entirety of the description herein. It will also be understood by one of ordinary skill in the art that each of these embodiments may be used in various combinations with the other embodiments provided herein.

The following examples further illustrate the invention but, of course, should not be construed as in any way limiting its scope.

EXAMPLES

The following materials and methods were employed in the experiments described in Examples 1-4.

Reagents

Phosphatidylcholine, Bodipy-cholesterol (23-(dipyrrometheneboron difluoride)-24-norcholesterol), (1,2-dioleoyl-sn-glycero-3-phosphoethanolamine-N-(lissamine rhodamine B sulfonyl)) and lecithin were obtained from a commercial source, AVANTI POLAR LIPIDS, INC. (Alabaster, AL). Lipid Removal Adsorbent (LRA) and cholesterol were obtained from a commercial source, SUPELCO (Bellefonte, PA).

Animals

Plasma was prepared from male mouse blood collected from the periorbital sinus of the eye as previously described (Ossoli et al., *PLoS One* 11: e0150083 (2016)) and lipids were measured enzymatically, as previously described (Rousset et al., *J. Pharmacol. Exp. Ther.*, 335: 140-148) (2010)). All mice including wild-type mice were on a C57BI/6N background. LCAT-KO mice (Sakai et al., *J. Biol. Chem.*, 272: 7506-7510) (1997) (MMRRC Stock No. 11840-MU) were obtained from JAX and LCAT-transgenic (Tg) mice were generated as described (Vaisman et al., *J. Biol. Chem.*, 270: 12269-12275 (1995)). ApoA-I KO (stock 002055; B6.129P2-Apoa1tm1Unc/J) and ApoA-I-Tg mice (stock 1927C57BL/6-Tg(APOA1)1Rub/J) were obtained from JAX. Mice were housed under controlled conditions, with a 12/12 h light/dark cycle, and were fed ad libitum either a standard rodent autoclaved chow diet containing 4.0% fat (NIH31 chow diet; Zeigler Brothers Inc., Gardners, PA). All animal experiments were approved by the Animal Care and Use Committee of the NHLBI (NIH Protocol #H-0050).

Fluorescent Lipid Exchange Between Lipoproteins

Pooled and individual human plasma samples were obtained from healthy and dyslipidemia donors. VLDL (very low density lipoprotein), LDL (low density lipoprotein), and HDL (high density lipoprotein) subfractions were obtained by differential ultracentrifugation (Brewer et al., Methods in Enzymolog., 128:223-246 (1986)). Lipoproteins were labeled with fluorescent PE and cholesterol either alone or together by adding 2 μl of fluorescent lipid stock solution (1 mg/ml ethanol) to 200 μl of human plasma or isolated VLDL, LDL, or HDL. The reaction mixture was gently mixed and then incubated overnight at 37° C. with mixing (700 rpm) using an Eppendorf 5436 THERMO-MIXER instrument. Human apoA-I, isolated as described in Brewer et al., Methods in Enzymolog., 128:223-246 (1986), was labeled with ALEXA FLUOR 647 dye as per the manufacturer's instructions (commercial supplier, INVITROGEN, Carlsbad, CA). To monitor cholesterol exchange between lipoproteins, 20 μl of VLDL, LDL, or HDL isolated from human plasma labeled with both fluorescent PE and cholesterol were added to 20 μl of unlabeled VLDL, LDL, or HDL, together with 4 μl ALEXA FLUOR 647 dye-tagged human apoA-I (1 mg/ml) and 16 μl of PBS (phosphatebuffered saline) (total reaction mixture of 60 μl) in 1.5 ml plastic conical tubes. Reference standard lipoproteins were prepared by adding 20 μl labeled lipoprotein to 40 μl PBS. Reference standard ALEXA FLUOR 647 dye-tagged human apoA-I contained 4 μl fluorescent apoA-I and 56 μl PBS. Reaction mixtures were gently mixed and then incubated overnight at 37° C., as above.

Multilamellar Vesicle Preparation

Multilamellar vesicles (MLVs) containing 24 mole % cholesterol were formed by combining 24.4 mg L-α-lecithin (32 μmoles) together with 4.25 mg cholesterol (10 μmoles) from their respective stock solutions in chloroform. Fluorescent MLVs included the addition of 171 μg (130 nmoles) fluorescent-tagged PE (1,2-dioleoyl-sn-glycero-3-phosphoethanolamine-N-(lissamine rhodamine B sulfonyl)), and/or 74 μg (128 nmoles) fluorescent Bodipy cholesterol (23-(dipyrrometheneboron difluoride)-24-norcholesterol) in chloroform. The lipid mixtures were dried under nitrogen. Two ml of PBS were added to the dried lipids, and then the lipids in buffer were vortexed for 10 min to re-suspend the dried lipids. Next the solution was sonicated for 10 min, using 1 min bursts separated by a 15 sec rest interval to generate MLVs. The cholesterol and phospholipid composition of the MLV particles was confirmed using enzymatic colorimetric assays (Waco) (Lambert et al., *J. Biol. Chem.*, 276: 15090-15098 (2001)).

rHDL preparation

Reconstituted HDL (rHDL) was prepared as described previously (Lerch et al., *Vox Sang* 71: 155-164 (1996); Thacker et al., *Immunology*, 149: 306-319 (2016)), with a final molar ratio of apolipoprotein A-I to soybean phosphatidylcholine of 1:150.

ApoA-I-Mediated Remodeling of MLVs

MLVs labeled with fluorescent PE and cholesterol either alone or together (20 μl containing 288 μg of total lipid) were incubated overnight at 37° C. with 20 μl pooled human plasma. In other experiments, unlabeled MLVs, or MLVs labeled with fluorescent PE and cholesterol either alone or together (20 μl containing 288 μg total lipid) was incubated overnight at 37° C. with excess ALEXA FLUOR 647 dye-tagged apoA-I (6 μl containing 6 μg apoA-I) and sufficient PBS for a total reaction mixture volume of 70 μl. ApoA-I was labeled with ALEXA FLUOR 647 dye according to the manufacturer's instructions (Invitrogen), as described in Neufeld et al., J. Biol. Chem., 279:15571-15578 (2004). Reaction mixtures were gently mixed and then incubated overnight at 37° C., as above.

Lipid-Coated LRA Preparation

Synthetic lipids were mixed as described above, using DMPC (1,2-dimyristoyl-sn-glycero-3-phosphocholine) or lecithin (PC:Cholesterol mole ratio 4:1) and with 5× fluorescent PE and cholesterol to increase acceptor lipoprotein fluorescent signal to optimal levels. Preliminary studies revealed that substituting lecithin with DMPC improved fluorescent PE transfer to lipoproteins. Lipid removal absorbent (LRA) was used as a source of calcium silicate hydrate crystals, with a mean diameter of 10 μM. Lipid-coated particles containing 21 mole % cholesterol were formed by combining 14 mg DMPC (21 μmoles) together with 2.12 mg cholesterol (5.48 μmoles) and the addition of 305 μg (200 nmoles) fluorescent-tagged PE (1,2-dioleoyl-sn-glycero-3-phosphoethanolamine-N-(lissamine rhodamine B sulfonyl)), and/or 27.5 μg (50 nmoles) fluorescent Bodipy cholesterol (23-(dipyrrometheneboron difluoride)-24-norcholesterol) from their respective stock solutions in chloroform. The lipid mixtures were dried under nitrogen. To form lipid-coated LRA particles, 80 mg of LRA was added along with 2 ml of PBS to the dried lipid mixture and then vortexed for 10 min. The resulting lipid-coated LRA particles were pelleted by centrifugation (1000 RPM, 1 min), and the supernatant was removed and replaced with 2 ml PBS. This washing process was repeated 5 times to ensure removal of any potential lipid vesicles not attached to LRA. For mouse plasma studies, which utilize much smaller plasma volumes than human plasma studies, the LRA particle lipid composition was optimized by increasing the DMPC:Chol ratio to 2:1 in order to enhance fluorescent PE transfer. These lipid-coated particles were formed by combining 11.8 mg DMPC (17.7 μmoles) together with 3.39 mg cholesterol (8.8 μmoles), 305 μg (200 nmoles) fluorescent-tagged PE (1,2-dioleoyl-sn-glycero-3-phosphoethanolamine-N-(lissamine rhodamine B sulfonyl)), and/or 27.5 μg (50 nmoles) fluorescent Bodipy cholesterol (23-(dipyrrometheneboron difluoride)-24-norcholesterol from their respective stock solutions in chloroform, and using 40 mg LRA. The minimum lipid to LRA ratio (mg/mg) of ≈4:1 was based on the previously determined lipid binding capacity of LRA (Gordon et al., *J. Proteome Res.*, 9: 5239-5249 (2010)). This lipid to LRA ratio provides sufficient lipid to completely cover the surface of LRA particles, thereby preventing direct lipoprotein binding to non-lipid-coated LRA surfaces. Herein, it was confirmed experimentally that lipoproteins do not bind to lipid-coated LRA particles by showing that *PE-labeled plasma did not transfer *PE to non-fluorescent lipid-coated LRA particles.

In Vitro Studies of Fluorescent Lipid Transfer from Lipid-Coated LRA Particles to Lipoproteins Human samples were obtained under study approved by the National Heart, Lung, and Blood institute's Institutional Review Board under protocol #93-CC-0094 and all subjects provided consent at enrollment. Pooled or individual human plasma samples (20 μl) were incubated with fluorescent PE- and cholesterol-tagged lipid-coated LRA (60 μl) and PBS (20 μl) for 4 hrs at 37° C. with mixing. Samples were then centrifuged at 1000 RPM for 1 min to pellet fluorescent lipid coated LRA particles. Supernatant samples were analyzed by agarose electrophoresis and FPLC. Lipid and lipoprotein composition of the pooled human plasma samples were determined by colorimetric assays for total cholesterol (TC), cholesterol, and triglycerides (TG) (Waco). Based on their composition, samples were designated as: low TG (LTG), high TG (HTG), low LDL (LL), and high HDL (HH). Total Cholesterol: 160.3, 227.5, 120.2, and 201.6, g/dL); HDL: 66.9, 39.2, 43.7, and 84.1, g/dL, respectively; Triglycerides: 37.9, 412.9, 114.7 and 60.9 g/dL, respectively. Triplicate samples of mouse plasma (10, 15, 20, or 25 μl) were incubated with fluorescent PE and cholesterol-tagged lipid-coated LRA (50 μl) and sufficient PBS for a total volume of 200 μl in 96-well plates for 1 hr at 37° C. with mixing (1200 RPM). Following the incubation, an additional 100 μl of PBS was added to each well, and then the plates were centrifuged at 2000 RPM for 2 min. 10 μl of supernatant from each triplicate sample was pooled for agarose gel electrophoresis analysis.

Fluorescent Lipid Agarose Gel Electrophoresis

Fluorescent lipoproteins were monitored by electrophoresis of 10 μl of reaction mixture or plasma samples, using SEBIA HYDRAGEL Lipoprotein(E) 15/30 agarose gels, which ran for 45, 60, or, 90 min. Fluorescent bands on the gel were imaged using a TYPHOON 9400 Variable Mode Imager (GE). Fluorescent PE, cholesterol, and apoA-I were detected using excitation/emission wavelengths of 532/560 nm, 488/520 nm and, 633/670 nm, respectively. Following imaging of fluorescent lipids and protein, gels were stained with SUDAN BLACK dye and rescanned. Quantitative analysis of fluorescent band intensity was performed using IMAGEQUANT 5.1 software.

FPLC Analysis

370 μl of plasma was applied to SUPEROSE 6 10/300 GL columns on an AKTA fast protein liquid chromatography (FPLC) (Amersham Biosciences) and 0.5 ml fractions were collected.

Supernatant PE and Cholesterol Fluorescence Measurements

For in vitro studies, 40 μl of reaction mixture supernatant was diluted with 200 μl of 1% TRITON X-100 surfactant to solubilize lipids. PE lissaminerhodamine and Bodipy-cholesterol fluorescence was measured with a Perkin Elmer VICTOR3 1420 Multichannel Counter using 540/600 and 485/520 excitation/emission filters, respectively. The amount of fluorescence emission/ng fluorescent lipid for lipid-coated LRA particles was determined by extracting various volumes of fluorescent PE and cholesterol-labeled lipid-coated LRA in TX-100 detergent and measuring lissaminerhodamine and Bodipy fluorescence. The mass of fluorescent PE and cholesterol per unit volume lipid LRA was then used to calculate fluorescence emission/ng of lipid LRA.

Proteomic Analysis

Agarose gel bands representing HDL or the band above HDL (15 lanes) were scraped from the gel plastic backing and transferred to plastic EPPENDORF tubes. Samples were subjected to in-gel reduction by dithiothreitol and carbamidomethylation by iodoacetamide, followed by overnight digestion with sequencing grade trypsin. Protein digests were filtered to separate peptides from gel fragments and desalted using ZIPTIP C18 columns (commercial supplier, MILLIPORE). Samples were re-suspended in 0.1% formic acid and analyzed by nanoLC-ESI-MS/MS on an ORBITRAP Elite mass spectrometer (commercial supplier, THERMO SCIENTIFIC). Mass data was searched against the Swiss-Prot database using MASCOT search engine and PROTEOME DISCOVER software (commercial supplier, THERMO). Identifications were validated using SCAFFOLD software (commercial supplier, PROTEOME SOFTWARE) with both peptide and protein thresholds set to 95% confidence and a minimum of 2 peptides for protein identification.

Example 1

This example demonstrates the incorporation of fluorescent PE and cholesterol into lipoproteins.

Figure 1B:
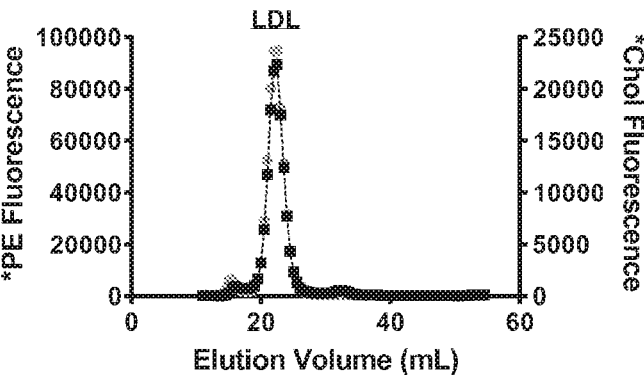
FIG. 1B is a graph showing the incorporation of fluorescent PE and cholesterol into human plasma lipoprotein LDL. FPLC analysis of fluorescent PE and cholesterol dual-labeled isolated human lipoprotein LDL was carried out. Black squares: PE fluorescence; Gray circles: Cholesterol fluorescence.
Figure 1C:
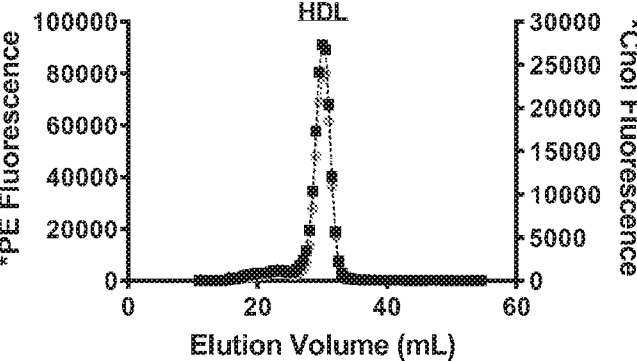
FIG. 1C is a graph showing the incorporation of fluorescent PE and cholesterol into human plasma lipoprotein HDL. FPLC analysis of fluorescent PE and cholesterol dual-labeled isolated human lipoprotein HDL was carried out. Black squares: PE fluorescence; Gray circles: Cholesterol fluorescence.

The effect of labeling isolated lipoprotein subfractions with trace amounts of both fluorescent PE (*PE (1,2-dioleoyl-sn-glycero-3-phosphoethanolamine-N-(lissamine rhodamine B sulfonyl))) and cholesterol (*Chol (23-(dipyrrometheneboron difluoride)-24-norcholesterol)) was first assessed by FPLC lipoprotein analyses, and it was found that the elution profiles for VLDL, LDL, and HDL were unaltered by the labeling process (FIG. 1A-C). The distribution of *Chol and *PE among lipoproteins detected by agarose gel electrophoresis was similar to that observed by FPLC analysis (FIG. 1A-C). The electrophoretic mobility of VLDL and HDL fractions on agarose gels was increased by dual *PE and *Chol labeling, most likely due to the presence of the positively charged fluorophore PE on the lipoprotein particles.

Figure 1D:
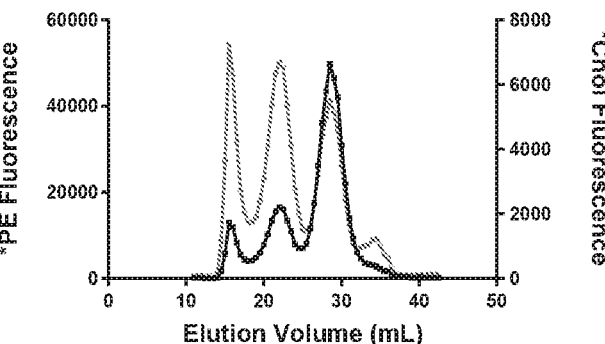
FIG. 1D is a graph showing the distribution of fluorescent PE and cholesterol in pooled human serum lipoproteins separated by FPLC. Black line: PE fluorescence; Gray line: Cholesterol fluorescence.
Figure 1E:
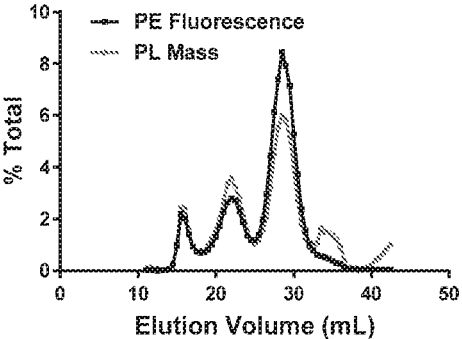
FIG. 1E is a graph showing a comparison of PE fluorescence (Black line; % of total PE fluorescence) with phospholipid mass (Gray line; % of total phospholipid mass).
Figure 1F:
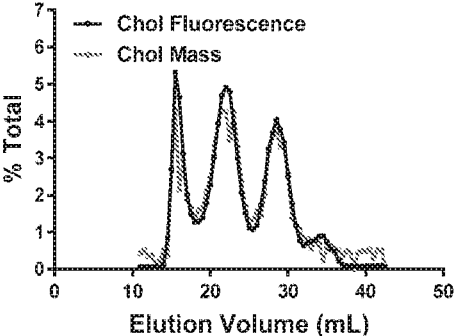
FIG. 1F is a graph showing a comparison of cholesterol fluorescence (Black line; % of total cholesterol fluorescence) with cholesterol mass (Gray line; % of total cholesterol mass).

It was next tested whether labeling of whole human plasma with *PE and *Chol would alter the FPLC elution profile of plasma lipoproteins, and, if incorporation of the fluorescent lipids into lipoproteins would be proportional to lipid mass. As above, the plasma lipoprotein phospholipid and cholesterol FPLC elution profiles were unaffected by labeling with either *PE or *Chol, but the pattern of incorporation of *PE and *Chol into plasma lipoproteins differed (FIG. 1D). Incorporation of *PE and *Chol into lipoproteins, however, was proportional to lipoprotein phospholipid and cholesterol mass, respectively (FIG. 1E, F). Thus, the differing patterns of incorporation of *PE and *Chol into lipoproteins reflects the different phospholipid and cholesterol composition of VLDL, LDL and HDL particles.

Example 2

This example demonstrates that fluorescent cholesterol incorporated into lipoproteins is exchangeable whereas fluorescent PE is not.

It was next assessed whether *PE would remain associated with labeled isolated lipoproteins when incubated with human plasma. When dual *PE and *Chol-labeled HDL, VLDL, or LDL was incubated with pooled human plasma, *PE did indeed remain associated with the original fluorescent-labeled lipoprotein in all cases, confirming the utility of non-exchangeable *PE as a lipoprotein marker. In marked contrast, fluorescent cholesterol readily exchanged between dual *PE and *Chol-labeled lipoproteins and unlabeled plasma lipoproteins.

It was next determined whether ALEXA647-tagged apoA-I would specifically bind to HDL. It was previously shown that apoA-I-mediated cellular cholesterol efflux is not altered when apoA-I is tagged with an ALEXA fluorophore (Neufeld et al., *J. Biol. Chem.,* 279: 15571-15578 (2004)). In the present study, ALEXA647-tagged apoA-I (*apoA-I) was co-incubated with dual *PE and *Chol-labeled HDL, VLDL, or, LDL isolated from whole plasma, and, unlabeled isolated lipoproteins for various amounts of time. *ApoA-I, *PE and *Chol fluorescence was monitored by agarose gel electrophoresis. *ApoA-I bound specifically to HDL, confirming that the fluorescent tag did not alter apoA-I binding to HDL nor induce non-specific binding to other lipoproteins. In these experiments, agarose gels were run for 45 min to avoid smearing of the *apoA-I bands on the gel. Consistent with the observation above in this Example, where fluorescent lipoproteins were incubated with unlabeled pooled human plasma, *PE remained associated with the original fluorescent-labeled lipoprotein, whereas *Chol rapidly exchanged (within 5 min) between fluorescent lipid-labeled and unlabeled lipoproteins. To better assess *Chol exchange between VLDL and LDL, agarose gels were run for 90 min to enhance resolution of the VLDL and LDL bands. *Chol rapidly equilibrated between VLDL and HDL, as well as between LDL and HDL, whereas *Chol exchange between VLDL and LDL was notably slower. Dose-response experiments demonstrated that net transfer of *Chol between VLDL or LDL after 4 hrs (at which time donor and acceptor cholesterol pools are in equilibrium), increased with increased amounts of unlabeled lipoprotein in the reaction mixture. These findings demonstrate that *Chol exchange between lipoproteins is both time and dose dependent.

Example 3

This example demonstrates that non-exchangeable fluorescent PE can be used to monitor lipoprotein remodeling.

Figure 2A:
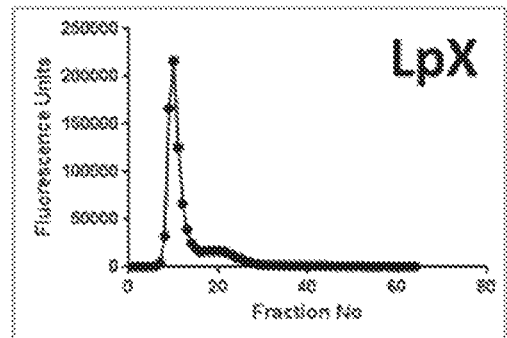
FIG. 2A is a graph showing the results of an FPLC analysis of synthetic fluorescent PE-tagged LpX before and after incubation with pooled human plasma.
Figure 2B:
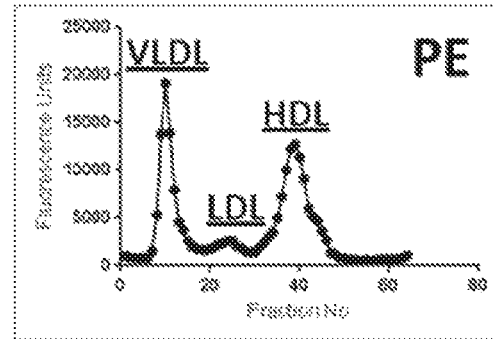
FIG. 2B is a graph showing the results of an FPLC analysis of synthetic fluorescent PE-tagged LpX before and after incubation with pooled human plasma.
Figure 2C:
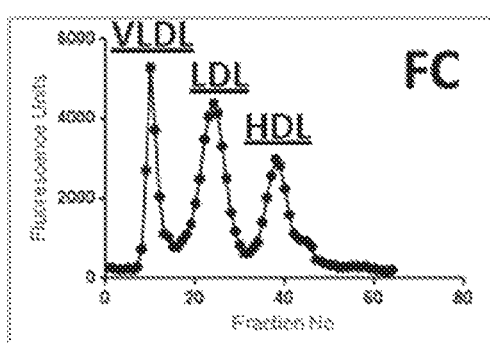
FIG. 2C is a graph showing the results of an FPLC analysis of synthetic fluorescent cholesterol-tagged LpX before and after incubation with pooled human plasma.

The studies were next extended to apoA-I-mediated remodeling of MLVs with a lipid composition similar to lipoprotein-X. Unlike typical lipoproteins, which contain a single layer of surface phospholipids and a hydrophobic core of cholesteryl esters and triglycerides, LpX (lipoprotein-X) is a multilamellar vesicle comprised of multiple phospholipid/cholesterol bilayers surrounding an aqueous core. In addition, unlike typical lipoproteins, LpX migrates toward the cathode during agarose gel electrophoresis (O and Frohlich, *J. Lipid Res.,* 36: 2344-2354 (1995)), and thus can be readily detected. It was previously shown that synthetic LpX is remodeled to HDL by the combined action of apoA-I and LCAT present in plasma (Ossoli et al., *PLoS One* 11: e0150083 (2016)). For the present studies, multilamellar synthetic LpX-like particles (Ossoli et al., *PLoS One* 11: e0150083 (2016)) that contained trace amounts of *PE, *Chol, or both, were synthesized, and then the fluorescent MLVs were incubated with human plasma (FIG. 2A-2C). Nearly all the fluorescent MLVs were consumed following incubation with human plasma. MLV-derived *PE associated specifically with HDL (FIG. 2A-2C). Unlabeled, dual, and singly fluorescent lipid-labeled MLVs underwent similar remodeling to HDL, indicating that the fluorophores on PE and cholesterol do not either alone or together perturb MLV remodeling. The partitioning of MLV-derived *Chol onto lipoproteins (FIG. 2A-2C) was similar to that seen above (Example 2), indicating that MLV-associated *Chol likely equilibrates among lipoproteins based on their cholesterol content. Single or dual fluorescent lipid-labeled MLVs were incubated with excess fluorescent-tagged or non-tagged apoA-I, to test if apoA-I would remove lipids from MLVs, and, if the fluorescent tags would interfere with this process. The results showed that *apoA-I did indeed remodel MLVs to form a new lipoprotein particle that contained *PE, *Chol and *apoA-I. The remodeling of MLVs did not appear to be perturbed by the presence of the fluorophores present on either of the lipids or on apoA-I.

Example 4

This example demonstrates fluorescent lipid transfer to lipoproteins from substrate-bound lipid donor membranes.

In Examples 1-3, lipoproteins were directly labeled with fluorescent lipids and apoA-I in order to monitor cholesterol exchange between lipoproteins and remodeling of lipoproteins. Given the interest in cellular cholesterol exchange as a marker of HDL function (Rosenson et al., *Circulation,* 125: 1905-1919 (2012)), fluorescent lipid-labeled donor membranes that mimic lipoprotein or cell membrane lipid surface structure or lipid composition, and are readily separable from acceptor membranes, could serve as an additional useful model system to study lipid transfer between lipid surfaces To this end, a simple method to assess fluorescent PE and cholesterol transfer from substrate-bound donor membranes to lipoproteins was developed. As proof of principle, DMPC:cholesterol lipid donor membranes were used with a composition similar to synthetic LpX, which as shown in Example 3, LpX transfers (i) both *PE and *Chol to HDL in an apoA-I-dependent manner, and (ii) *Chol to VLDL and LDL by exchange. Calcium silicate hydrate crystals (10 μm sized) (Lipid Removal Adsorbent (LRA), which readily adsorb lipids, were coated with DMPC, cholesterol and trace amounts of *PE and *Chol. The donor lipid membrane preparations were readily separated from the lipoprotein acceptor particles by a simple low speed centrifugation step, which pellets the donor, but not the acceptor particles.

Figure 6:
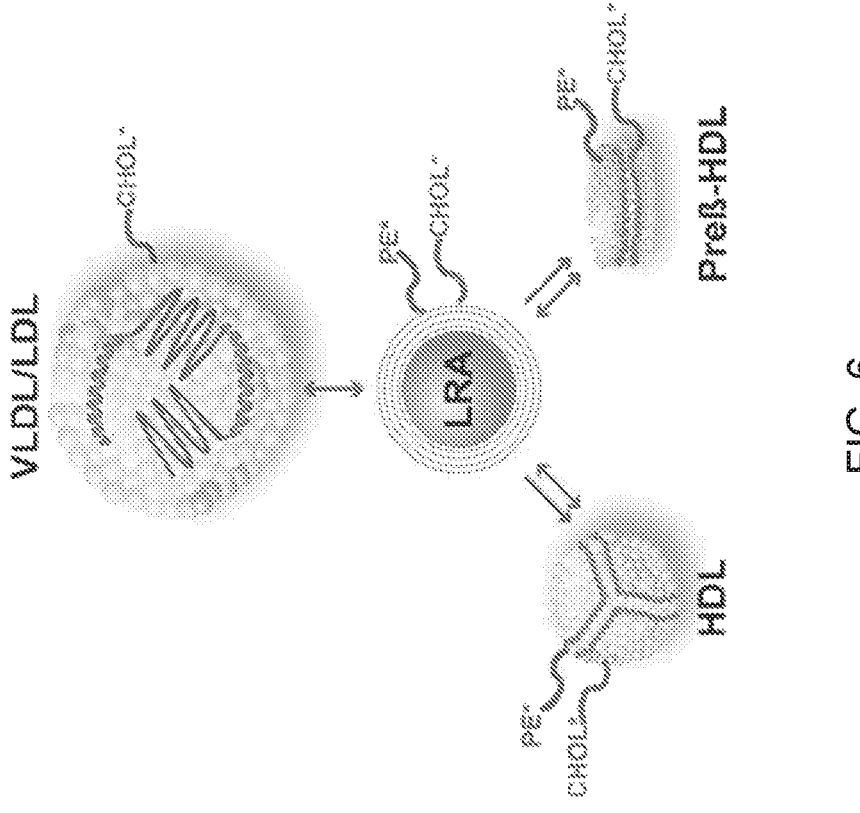
FIG. 6 is a schematic illustrating that lipid-coated LRA particles containing fluorescent cholesterol and PE can be used to monitor both the active removal of fluorescent non-exchangeable PE (HDL-apoA-I-mediated solubilization) and the passive exchange of fluorescent cholesterol to, and between, plasma lipoproteins.

To assess the potential specificity of the acquisition of lipid-coated LRA *PE by HDL as well as possible interactions between the lissaminerhodamine and Bodipy fluorophores, singly or doubly-labeled fluorescent *PE and *Chol lipid-coated LRA was incubated with human plasma. LRA-derived *PE robustly transferred to plasma HDL with relatively little transfer to VLDL or LDL, consistent with the previously observed HDL-specific uptake of LpX-derived *PE in whole human plasma (Example 3; FIG. 6). As seen previously using LpX alone (Example 3; FIG. 6), lipid-coated LRA *Chol transferred to all lipoproteins. Transfer of both lipid-coated LRA *PE or *Chol to lipoproteins occurred in a dose-dependent manner. The distribution of *PE and *Chol that transferred from singly- or doubly-labeled *PE and/or *Chol lipid-coated LRA to plasma lipids was nearly identical, indicating that the lissamine and Bodipy fluorescence was not altered when the two fluorophores were present together on lipoprotein particles.

Figure 3:
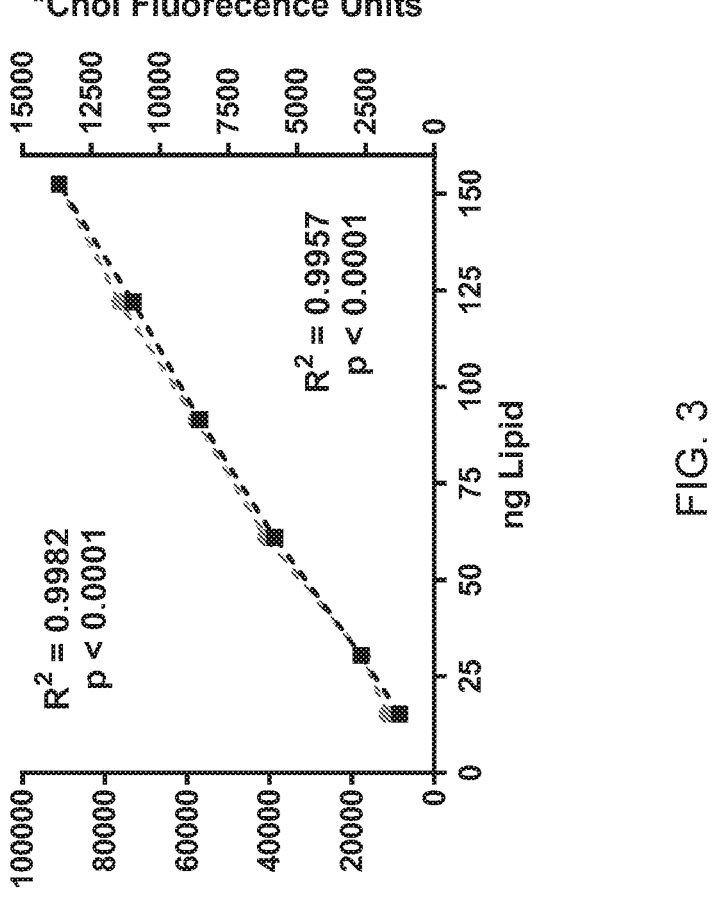
FIG. 3 is a graph showing the calibration of LRA lipid particle PE and cholesterol fluorescence. Volumes of fluorescent lipid-tagged LRA lipid particles corresponding to the lipid masses shown were extracted with TX-100 detergent and PE and cholesterol fluorescence were measured.

To further assess the potential specificity of the acquisition of fluorescent lipid-coated LRA-derived *PE by plasma HDL, reconstituted HDL (rHDL) and isolated plasma HDL and LDL were compared as acceptors. rHDL, an avid cholesterol acceptor, is a synthetic pre-β-like HDL particle that is made by reconstituting lipid-free apoA-I with phosphatidylcholine (Chen et al., *J. Cardiovasc. Pharmacol. Ther.,* 17: 315-323 (2012)). Donor particle-derived *PE robustly transferred to isolated HDL and reconstituted HDL but not to LDL, consistent with the previously observed HDL-specific uptake of LpX-derived *PE (Example 3) and lipid-coated LRA donor particle-derived *PE in whole human plasma. Transfer of both donor lipid particle *PE and *Chol to lipoproteins occurred in a dose-dependent manner. Interestingly, reconstituted HDL served as an avid cholesterol acceptor. Fluorescent agarose gel electrophoresis revealed that the reconstituted HDL formed two bands: (1) a slower migrating band that acquired both *Chol and *PE from lipid donor LRA particles, and (2) a faster migrating band that acquired only *PE. Thus, the latter band was only revealed by its uptake of *PE. Based on total *PE and *Chol fluorescence intensity, and their respective fluorescence/mass ratios (FIG. 3), it was calculated that 3 moles of *Chol transferred per mole of *PE from lipid LRA particles to reconstituted HDL.

The effect of altering the phospholipid composition and cholesterol content of LRA donor particles on the transfer of fluorescent PE and cholesterol to human plasma lipoproteins was examined. In the absence of cholesterol, apoA-I-mediated transfer of *PE was markedly reduced, independent of the phospholipid composition (DMPC vs. egg lecithin). However, with the addition of cholesterol to phospholipid donor particles, specific *PE transfer to plasma HDL was markedly increased, and was dependent on the phospholipid composition (DMPC>egg lecithin). This finding suggests that cholesterol alters the organization of phospholipids on the lipid coated LRA particle surface, rendering *PE more available for apoA-1-mediated removal. Transfer of *Chol from donor LRA particles to all plasma lipoproteins by passive exchange, on the other hand, was solely dependent on donor LRA phospholipid composition.

To directly confirm the role of HDL and apoA-I in mediating *PE transfer from donor LRA particles to plasma HDL, *PE transfer from fluorescent lipid-coated LRA particles was compared to plasma lipoproteins from wild-type and genetically engineered knock-out and transgenic LCAT and apoA-I mice. It was previously shown that plasma HDL concentrations are increased in LCAT-Tg mouse plasma (Vaisman et al., *J. Biol. Chem.,* 270: 12269-12275 (1995)) and are increased to an even greater extent in apoA-I Tg mice (Rubin et al., *PNAS,* 88, 434-438 (1991)). As compared to wild-type mouse plasma, *PE transfer to HDL was increased to LCAT-Tg mouse plasma HDL, in a plasma dose-dependent manner, and was absent in LCAT-KO mice, which lack HDL. These findings demonstrate that lipid donor particle *PE plasma uptake is HDL-dependent, and proportional to plasma HDL concentration. ApoA-I Tg mice have markedly increased levels of plasma HDL. Compared to both wild-type and LCAT-Tg mouse plasma, accordingly, LRA donor particle *PE transfer to apoA-I Tg mouse plasma HDL was markedly increased. *PE transfer to plasma HDL was also plasma dose-dependent, and absent in apoA-I KO mice, which lack HDL. These findings demonstrate that LRA donor particle *PE transfer to mouse plasma is apoA-I-dependent.

Figure 4B:
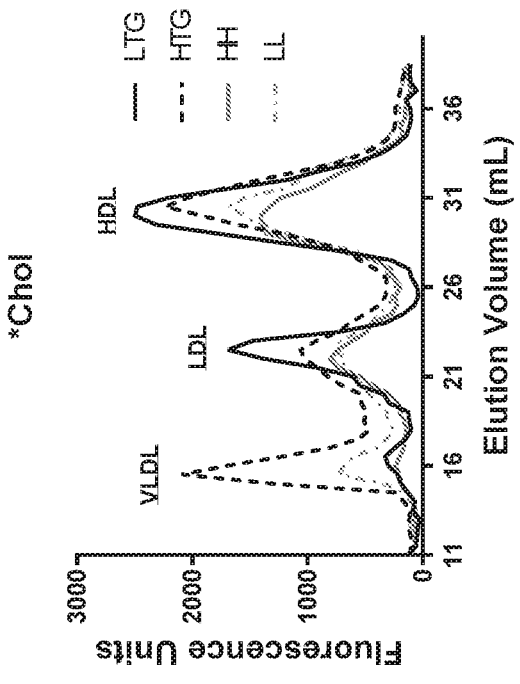
FIG. 4B is a graph showing the distribution of LpX LRA-derived fluorescent cholesterol in FPLC fractions of pooled human plasma samples. LTG: Low TG; HTG: High TG; LL: Low LDL; HH; High HDL.
Figure 4B:
Figure 4A:
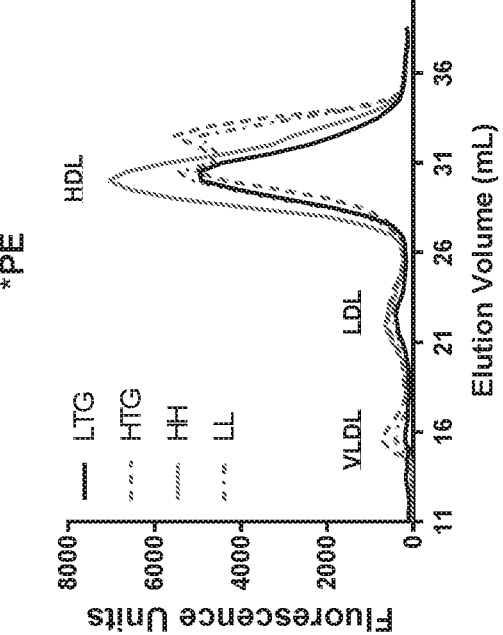
FIG. 4A is a graph showing the distribution of LpX LRA-derived fluorescent PE in FPLC fractions of pooled human plasma samples. LTG: Low TG; HTG: High TG; LL: Low LDL; HH; High HDL.

The utility of lipid-coated LRA in evaluating the transfer of fluorescent PE and cholesterol to pooled human plasma lipoprotein samples containing varying amounts of LDL, HDL, and triglycerides was next assessed (FIG. 4A-4B). As assessed by agarose gel analysis and FPLC, *PE transferred from donor particles to HDL, but little, if any, *PE transferred to VLDL or LDL (FIG. 4A, B). This finding is consistent with previous observations (Ossoli et al., *PLoS One* 11: e0150083 (2016)) that donor LRA particle *PE is actively incorporated into plasma HDL (see Example 4). In contrast, *Chol transferred from lipid-coated LRA to all lipoproteins (FIG. 4A, B), in a similar manner to the studies in Example 4. FPLC analysis revealed that the different pooled human plasma samples displayed unique patterns of uptake of both *PE and *Chol (FIG. 4A, B).

This method also allowed the identification of a band above the HDL band on agarose gels that acquired both *PE and *Chol (FIG. 4A, B). Proteomic analysis of the proteins that were identified in the HDL band vs. the established HDL proteome (//homepages.uc.edu/-davidswm/HDLproteome.html) revealed that all but one of the proteins (coagulation factor 10 (FA10)) were bona fide HDL binding proteins, thus validating the in-gel mass spectrometric proteomic analysis (Table 1). Mass spectrometric proteomic analysis revealed the uppermost band in the HTG sample was markedly enriched with apoA-I and apoA-II, but not other HDL-associated proteins (Table 1). Since robust uptake of both *PE and *Chol by rHDL from donor particles was shown, this finding suggests that other HDL species (potentially pre-α-HDL (Asztalos et al., *Curr. Opin. Lipidol.,* 22: 176-185 (2011)) present in the uppermost band likely acquire fluorescent PE and cholesterol from the donor particles.

TABLE 1

Proteomic Analysis of HTG Pooled Human Plasma ALB and HDL Bands

| Identified Proteins (30) | Accession Number | Molecular Weight | ALB (*TSC) | HDL (*TSC) |
|---|---|---|---|---|
| Serum albumin | ALBU | 69 kDa | 938 | 421 |
| Apolipoprotein A-I | APOA1 | 31 kDa | 58 | 4 |
| Vitamin D-binding protein | VTDB | 53 kDa | 0 | 50 |
| Prothrombin | THRB | 70 kDa | 0 | 49 |
| Inter-alpha-trypsin inhibitor heavy chain H2 | ITIH2 | 106 kDa | 0 | 39 |
| Cluster of Serum amyloid A-I protein | SAA1 | 14 kDa | 10 | 23 |
| Apolipoprotein A-II | APOA2 | 11 kDa | 14 | 19 |
| Afamin | AFAM | 69 kDa | 0 | 21 |
| Clusterin | CLUS | 52 kDa | 0 | 23 |
| Alpha-1-antitrypsin | A1AT | 47 kDa | 0 | 23 |
| Haptoglobin | HPT | 45 kDa | 0 | 30 |
| Apolipoprotein C-III | APOC3 | 11 kDa | 9 | 13 |
| Vitronectin | VTNC | 54 kDa | 0 | 19 |

TABLE 1-continued

Proteomic Analysis of HTG Pooled Human Plasma ALB and HDL Bands

| Identified Proteins (30) | Accession Number | Molecular Weight | ALB (*TSC) | HDL (*TSC) |
|---|---|---|---|---|
| Antithrombin-III | ANT3 | 53 kDa | 0 | 14 |
| Apolipoprotein E | APOE | 36 kDa | 3 | 14 |
| Alpha-1β-glycoprotein | A1BG | 54 kDa | 0 | 13 |
| Protein AMBP | AMBP | 39 kDa | 5 | 10 |
| Serum paraxonase/arylesterase 1 | PON1 | 40 kDa | 10 | 0 |
| Serum amyloid A-4 protein | SAA4 | 15 kDa | 0 | 9 |
| Ceruloplasmin | CERU | 122 kDa | 0 | 8 |
| Kininogen-1 | KNG1 | 72 kDa | 0 | 8 |
| Retinol-binding protein 4 | RET4 | 23 kDa | 0 | 9 |
| Inter-alpha-trypsin inhibitor heavy chain H1 | ITIH2 | 101 kDa | 0 | 9 |
| Alpha-2-HS-glycoprotein | FETUA | 39 kDa | 0 | 5 |
| Apolipoprotein A-IV | APOA4 | 45 kDa | 0 | 6 |
| Apolipoprotein C-II | APOC2 | 11 kDa | 0 | 2 |
| Apolipoprotein D | APOD | 21 kDa | 0 | 4 |
| Transthyretin | TTHY | 16 kDa | 0 | 3 |
| Coagulation factor X | FA10 | 55 kDa | 0 | 3 |

Figure 5:
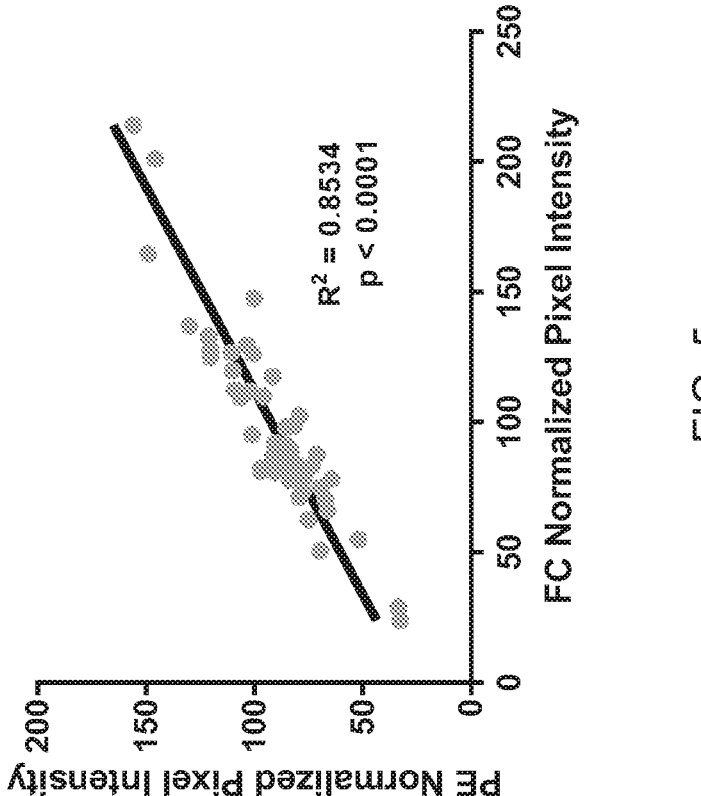
FIG. 5 is a graph showing the total pixel intensity of HDL PE and cholesterol bands quantified for all fifty samples and normalized with respect to the reference standard on the gels (unknown HDL *PE/standard HDL *PE; unknown HDL *Chol/standard HDL *Chol). Note that HDL *PE and *FC fluorescence are highly correlated.

Lastly, the transfer of *PE and *Chol from LRA lipid donor particles to a set of human plasma samples from fifty individuals was assessed (FIG. 5). Agarose gel electrophoresis reproduced the results observed, namely that *PE transferred only to HDL (and variably to the albumin band) and that *Chol transferred to VLDL, LDL, and HDL. The intensity of HDL *PE and *Chol fluorescence in these fifty samples was highly correlated (FIG. 5; $R^2=0.8534$; $p<0.0001$), suggesting that the mole ratio of phospholipid and cholesterol apoA-I-mediated transfer from LRA to HDL donor lipid particles is highly conserved.

Example 5

This example demonstrates a high-throughput, cell-free HDL lipid efflux assay.

A schematic of the assay is illustrated in FIG. 14. Pooled samples of whole human plasma from 84 donors were mixed with donor particles having a nominal diameter of 10 microns. The donor particles were calcium silicate hydrate crystals (LRA) coated with DMPC, unlabeled cholesterol, *Chol, and *PE. The quantity of *Chol and *PE on the donor particles prior to performing the assay were the total LRA *Chol and the total LRA *PE, respectively. The molar ratio of DMPC to cholesterol on the particles was 2:1. The mixture was incubated in 96-well plates for 1 hour at 37° C. with shaking at 1200 rpm (rotations per minute).

The donor particles were separated from lipoproteins by rapid centrifugation at 2,000 rpm for 2 minutes. A portion of the supernatant was removed (50 μL), mixed with an additional 50 μL of saline and 100 μL of 1% TX-100 in order to solubilize the fluorescent lipoprotein particles. The quantity of *PE and *Chol in the supernatant was then measured by fluorometric measurement.

ApoA-I in the whole plasma specifically transferred at least a portion of the *PE from the donor particles to the HDL. Thus, non-exchangeable *PE specifically labeled HDL in a manner that was dependent on apoA-I functionality.

*Chol, on the other hand, labeled all lipoprotein acceptor particles (VLDL, LDL and HDL) by passive exchange from the donor particles.

As a negative control, the donor particles were separately incubated with saline only. The fluorescence in the saline control supernatant was extremely low (<0.1%).

The percentage of *PE efflux (% *PE efflux) was calculated as follows:

%*PE efflux=Supernatant*PE/Total LRA*PE (50 μL).

The percentage of *Chol efflux (% *Chol efflux) was calculated as follows:

%*Chol efflux=Supernatant*Chol/Total LRA*Chol (50 μL).

The clinical characteristics of the 84 donors is shown in Table 2.

TABLE 2

| Cohort, n | 84 Donors |
|---|---|
| Gender (% male) | 51.19 |
| Age (years) | 60.43 ± 7.78 |
| BMI | 29.81 ± 6.74 |
| Systolic BP (mmHg) | 115.88 ± 14.82 |
| Diastolic BP (mmHg) | 62.29 ± 10.31 |
| Statins (%) | 52.38 |
| Total cholesterol (mg/dl) | 180.02 ± 33.26 |
| LDL cholesterol (mg/dl) | 93.57 ± 30.59 |
| HDL cholesterol (mg/dl) | 58.66 ± 17.54 |
| Triglycerides (mg/dl) | 140.28 ± 105.64 |
| HDL particle number (nmol/L) | 35.81 ± 6.07 |
| HDL size (nm) | 9.33 ± 0.54 |
| LDL particle number (nmol/L) | 1189.06 ± 414.78 |
| LDL size (nm) | 20.45 ± 0.60 |
| VLDL particle number (nmol/L) | 62.71 ± 53.17 |
| VLDL size (nm) | 50.17 ± 8.15 |
| TB (mm2) | 0.0109 ± 0.0037 |
| NCB (mm2) | 0.0107 ± 0.0036 |
| DCB (mm2) | 0.00024 ± 0.00046 |
| Calcified burden (Agatston score) | 137.76 ± 246.89 |

Example 6

This example demonstrates the plasma dose dependency and linearity of the assay of Example 5.

The analytical performance of the assay Example 5 was validated.

The % *PE efflux and % *Chol efflux was measured in human pooled plasma samples of various volumes ranging from 15-50 μL using the assay described in Example 5. The results are shown in FIG. 7 and Table 3.

TABLE 3

| μL | *PE | | | | *Chol | | | |
|---|---|---|---|---|---|---|---|---|
| | N | mean | SD | CV % | N | mean | SD | CV % |
| 15.0 | 3 | 2.10 | 0.100 | 4.76 | 3 | 1.60 | 0.100 | 6.25 |
| 17.5 | 3 | 2.67 | 0.153 | 5.73 | 3 | 2.13 | 0.058 | 2.71 |
| 20.0 | 3 | 3.30 | 0.173 | 5.25 | 3 | 2.67 | 0.115 | 4.33 |
| 22.5 | 3 | 3.63 | 0.208 | 5.73 | 3 | 2.97 | 0.058 | 1.95 |
| 25.0 | 3 | 4.00 | 0.100 | 2.50 | 3 | 3.27 | 0.058 | 1.77 |
| 30.0 | 3 | 4.93 | 0.058 | 1.17 | 3 | 4.10 | 0.100 | 2.44 |
| 50.0 | 3 | 7.70 | 0.100 | 1.30 | 3 | 6.27 | 0.058 | 0.92 |
| | | | | 3.78 | | | | 2.91 |
| | | | | CV % av. | | | | CV % av. |

Figure 7:
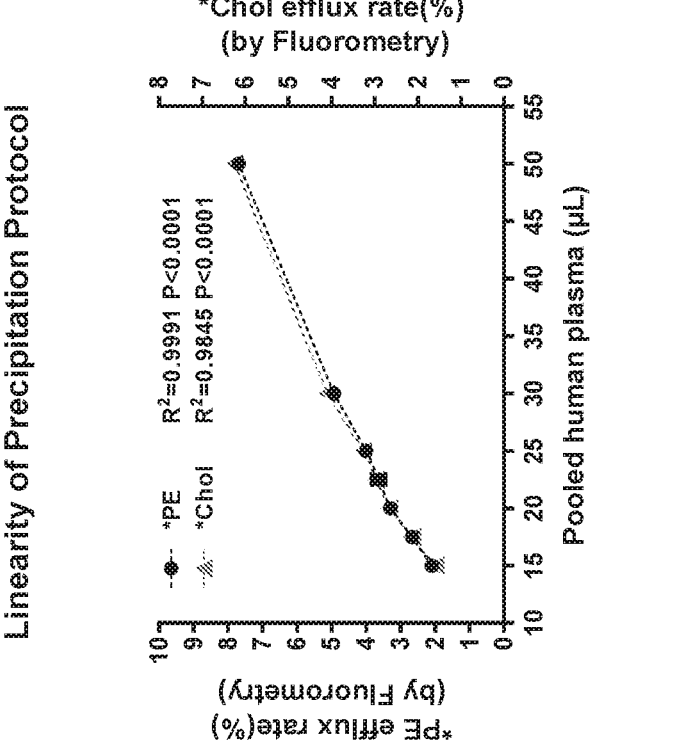
FIG. 7 is a graph showing *PE efflux rate (%), the *Chol efflux rate (%), measured by the assay of Example 5 for the indicated sample volumes of pooled human plasma.

As shown in FIG. 7, the *PE efflux value and *cholesterol efflux value showed plasma dose dependency and linearity between 15 μL and 50 μL. Moreover, as shown in Table 3, the coefficient of variation (CV) is totally under the average value of 4%, although it depends on plasma volume. Thus, the assay of Example 5 is very reproducible considering that the values of the conventional cell cholesterol efflux capacity (CEC) assay described in Khera et al., *NEJM*, 364:

127-35 (2011) ("cell CEC assay") usually have a greater CV (>10%). Thus, this assay is both quantitative and reproducible and amenable for clinical testing.

For the clinical studies that follow, the plasma volume of 25 μL was chosen. Typically, clinical assays are performed using ~10 μL of plasma in about 10 min.

Example 7

This example demonstrates that PE transfers from donor particles specifically to plasma HDL.

The assay of Example 5 was carried out using 84 clinical samples, except that the fluorescence was measured by separating the HDL and the LDL/VLDL in the supernatant on an electrophoresis gel. The electrophoresis gel separated the HDL and the LDL/VLDL into separate fluorescent bands. The electrophoresis gels showed that the *PE was present only in the HDL band, while the *Chol was present on both the HDL and the LDL/VLDL band. These data confirm that *PE transferred from LRA donor particles specifically to plasma HDL. In contrast, *Cholesterol transferred to not only HDL but also LDL/VLDL.

Example 8

This example demonstrates that the results obtained by fluorometric and gel analyses are highly correlated.

Figure 9:
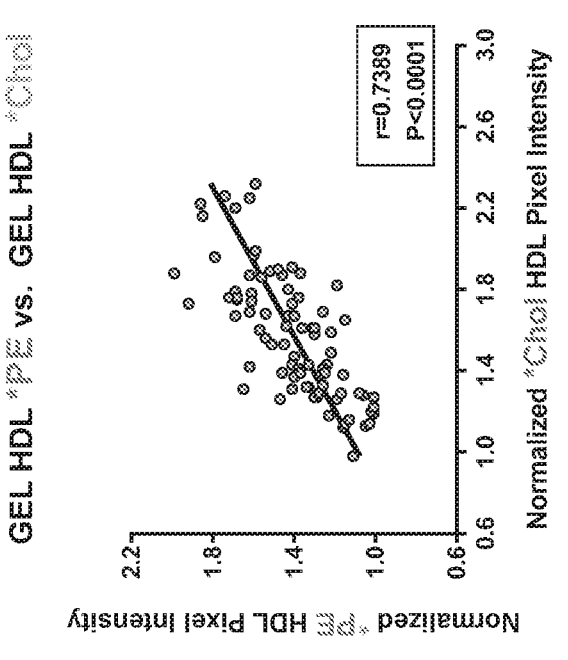
FIG. 9 is a graph showing the correlation of normalized *PE HDL pixel intensity with the normalized *Chol HDL pixel intensity.
Figure 8:
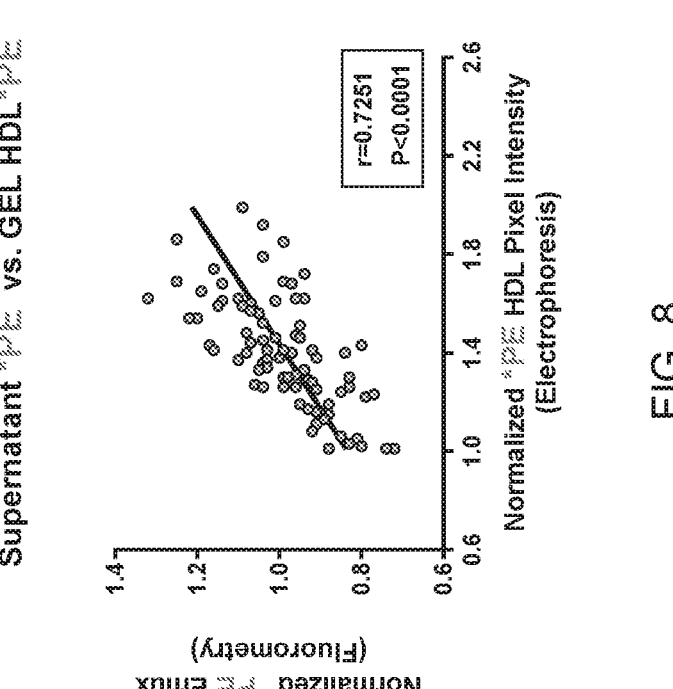
FIG. 8 is a graph showing the correlation of normalized *PE efflux measured by fluorometry with the normalized *PE HDL pixel intensity measured by electrophoresis.
Figure 10:
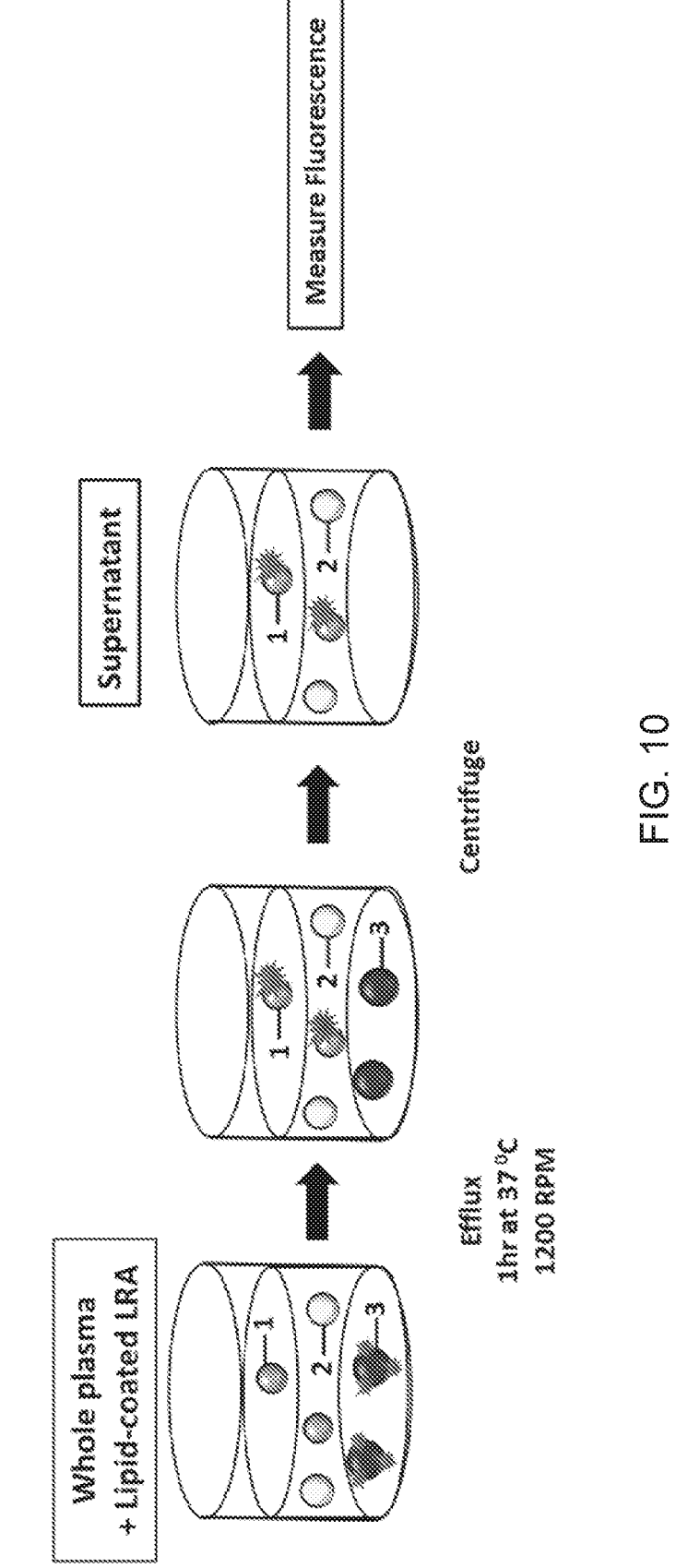
FIG. 10 is a schematic of the *PE efflux assay of Example 5 in accordance with an embodiment of the invention.

The correlation between the fluorometric analysis of the supernatant carried out in Example 6 and the electrophoresis analysis of the supernatant carried out in Example 7 was analyzed. The normalized *PE efflux (fluorometry) and the normalized *PE HDL pixel intensity (electrophoresis) were plotted on a graph (FIG. 8). The normalized *PE HDL pixel intensity and the normalized *Chol HDL pixel intensity were plotted on a graph (FIG. 9).

As shown in FIG. 8, the *PE efflux value by fluorometry highly correlates to *PE pixel intensity of HDL band by electrophoresis (Pearson correlation coefficient r=0.7251, P<0.0001). Thus, the *PE specificity to HDL allows the direct use of human whole plasma without any additional processing of the plasma.

However *cholesterol, which is commonly used in other methods, including the cell CEC assay, usually needs pretreatment to isolate HDL from human whole plasma in advance of the efflux assay. The isolation of HDL involves the depletion of ApoB-related lipoproteins such as LDL and VLDL from whole plasma by polyethylene glycol precipitation, thus the cell CEC assay gives separated HDL in the supernatant. Reportedly, supernatant after ApoB depletion still includes polyethylene glycol (PEG) at a high concentration. It is possible that the efflux data obtained by the cell CEC assay is effected by residual PEG.

In contrast, the assay of Example 5 advantageously reflects absolutely physiological condition excluding such an artifact as PEG.

Moreover, the *PE Pixel intensity of HDL band and *Cholesterol Pixel intensity of HDL band were also highly correlated (FIG. 9), which is consistent with the data shown in FIG. 5. Thus, *PE can be alternative marker for HDL functionality.

Example 9

This example demonstrates that the cell-free phospholipid transfer and cellular cholesterol efflux are correlated.

The assay of Example 5 and the cell cholesterol efflux capacity (CEC) assay described in Khera et al., *NEJM,* 364:

127-35 (2011) ("cell CEC assay") were carried out using 25 microliters of human plasma. The normalized *PE efflux measured by the assay of Example 5 and the normalized cellular CEC value measured by the cell CEC assay were plotted. The results of these assays were modestly correlated (Pearson correlation coefficient r=0.3457, P=0.0013).

Example 10

This example demonstrates that cell-free phospholipid transfer highly correlates with plasma apoA-I levels and HDL particle number.

A correlation analysis of normalized *PE efflux as measured by the assay of Example 5 or normalized cellular CEC value as measured by the cell CEC assay with Apo-AI and HDL particle number was carried out. The *PE transfer highly was correlated with ApoA-I plasma levels. Surprisingly, the Pearson correlation coefficient r was much higher with the *PE assay of Example 5 compared to the cell CEC assay. This suggests that the *PE efflux value is more specific to ApoA-I than the cell CEC value. The *PE transfer highly correlated with HDL particle number, although cell CEC assay value was also modestly correlated with HDL particle number.

Since ApoA-I is major component of HDL, the finding that both ApoA-I levels and HDL particle number correlate with *PE efflux is entirely consistent.

Example 11

This example demonstrates that *PE efflux inversely correlates with non-calcified plaque burden.

A correlation analysis of non-calcified plaque burden (NCB) of 223 arteries from 84 clinical samples with normalized *PE efflux as measured by the assay of Example 5 or normalized cellular CEC value as measured by the cell CEC assay was carried out. The measurement of NCB was determined by the method described by Gordon et al., *Atherosclerosis,* 278: 278-85 (2018).

These results showed that *PE efflux inversely correlates with NCB. Moreover, this correlation is higher than that of cell CEC assay.

Example 12

This example demonstrates that *PE efflux inversely correlates with non-calcified plaque burden.

The results of Example 11 were confirmed by another statistical analytical method. The *PE efflux and the cell CEC assay values were classified into three groups, namely LOW, MED and HIGH. Consistent with the Scatter plot analysis, the analysis of this Example indicated that NCB was associated with *PE efflux level. The association of cell CEC assay efflux with NCB was not as strong as with the assay of Example 5.

Example 13

This example demonstrates that *PE is significantly correlated with total burden, non-calcified burden and fibrous fatty burden.

The measurement of total burden, non-calcified burden and fibrous fatty burden was determined by the method described by Gordon et al., *Atherosclerosis,* 278: 278-85 (2018). The association of *PE efflux as measured by the assay of Example 5 with coronary computed tomography angiography (CCTA) all plaque parameters was also confirmed. The results are shown in Table 4.

TABLE 4

| Variable | Cell CEC assay | | *PE efflux | |
|---|---|---|---|---|
| | β | P | β | P |
| TB | −0.22 | 0.001 | −0.36 | 0.0001 |
| NCB | −0.21 | 0.001 | −0.37 | 0.0001 |
| DCB | −0.01 | 0.881 | 0.08 | 0.248 |
| FFB | −0.21 | 0.002 | −0.28 | 0.0001 |
| NB | −0.04 | 0.557 | −0.12 | 0.079 |
| CB (Aga) | −0.15 | 0.022 | −0.02 | 0.791 |

Linear regression model. Results reported as standardized β coefficient (P values).
TB: total burden,
NCB: non-calcified burden,
DCB: dense-calcified burden,
FFB: fibrous fatty burden,
NB: necrotic burden.
CB(Aga): Agastone Calcium Score.
DCB values were log10 transformed.

*PE was significantly correlated with total burden, non-calcified burden and fibrous fatty burden. Each of these associations with the *PE assay of Example 5 were better compared to the cell CEC assay.

Example 14

This example demonstrates that *PE is independent of various clinical markers to assess the risk of non-calcified plaque burden.

Multivariable adjusted linear regression analysis was carried out to determine the association between the *PE efflux assay of Example 5 (or the cell CEC assay) and non-calcified plaque burden. The results are shown in Table 5.

TABLE 5

| Variable | Cell CEC assay | | *PE efflux | |
|---|---|---|---|---|
| | β | P | β | P |
| Unadjusted | −0.21 | 0.001 | −0.37 | 0.0001 |
| Age-adjusted | −0.21 | 0.002 | −0.32 | 0.0001 |
| Gender-adjusted | −0.12 | 0.03 | −0.20 | 0.005 |
| BMI-adjusted | −0.06 | 0.311 | −0.33 | 0.0001 |
| LDL-C-adjusted | −0.22 | 0.001 | −0.35 | 0.0001 |
| HDL-C-adjusted | −0.09 | 0.164 | −0.18 | 0.004 |
| ApoA-I-adjusted | −0.14 | 0.038 | −0.27 | 0.0005 |
| Triglyceride-adjusted | −0.21 | 0.001 | −0.37 | 0.0001 |
| Statin-adjusted | −0.18 | 0.063 | −0.37 | 0.0001 |

These analyses revealed that the cell CEC assay was effected by body mass index (BMI), HDL-C and statin treatment. The *PE assay of Example 5 was not effected by any clinical biomarkers. Even when ApoA-I was adjusted, PE efflux was still significantly associated with NCB. This finding suggests that the association of *PE efflux with NCB includes other factors in addition to ApoA-I plasma concentration level.

Example 15

This example demonstrates advantages of the assay of Example 5.

The assay of Example 5 is unique as it uses *PE as a marker for HDL functionality. Because *PE is specific to HDL, it is possible to use human whole plasma without any pretreatment, unlike other cholesterol efflux methods. Furthermore, the conventional cell CEC assay requires radiolabeled cholesterol, cell culture and induction of ABCA1 expression, which is time-consuming, and moreover, provides highly variable data. The cell CEC assay is not amenable for use as a clinical assay.

The Sysmex Corp. method (described in Harada et al., *J. Applied Labor. Med.*, jalm.2016.022913; DOI: 10.1373/jalm.2016.022913 (2017)) measures Cholesterol Uptake Capacity (CUC) of HDL ("the Sysmex method"). These investigators found a high correlation with non-ABCA1 C-CEC efflux. Thus, this method is based on the passive exchange of cholesterol between donor liposomes and HDL. A major limitation of the Sysmex method is that it was only validated in patients with LDL-C<100 mg/dL, namely who had statin treatment for LDL-C control since their assay is seemingly effected by LDL-C levels. On the contrary, the *PE assay of Example 5 is not effected by any clinical markers (Example 14) and better correlates with NCB compared with conventional cell CEC assay.

The assay of Example 5 is unique because it measures apoA-I functionality, not cholesterol uptake capacity of HDL, using a non-exchangeable fluorescent phospholipid.

The features and advantages of the assay of Example 5 are shown in Table 6.

TABLE 6

| | Example 5 assay | Sysmex method | Cell CEC assay |
|---|---|---|---|
| Principle | Phospholipid efflux mediated by ApoA-I | Cholesterol uptake by HDL | Cholesterol efflux dependent on ApoA-I |
| ApoB depletion from plasma | NO | YES | YES |
| Cell culture | NO | NO | YES |
| Radioactive | NO | NO | YES |
| Total assay time | 1.5 hrs | 6 hrs | >3 days |
| Additional preparation | NONE | ■ ApoA-I conc. adjustment ■ Anti-ApoA-I antibody ■ H₂O₂ incubation . . . etc. | ■ ABCA1 induction ■ ACAT inhibition ■ Cell lysis . . . etc. |
| Limitations in CVD risk assessment | NONE | Only validated in patients with LDL-C < 100 (mg/dL) | Effected by BMI |

Example 16

Methods

Lipid-coated CSH (LC-CSH) preparation. Lipid coated-calcium silicate hydrate crystals (LC-CSH) were prepared as previously described with minor modifications (Neufeld, E. B. et al., Biology (Basel), 8, doi: 10.3390/biology8030053 (2019), incorporated by reference in its entirety). Briefly, Lipid Removal Absorbant (LRA; commercial supplier, SUPELCO #13358-U, MERCK KGaA, Darmstadt, Germany) was used as a source of CSH particles. LC-CSH were formed by combining 11.8 mg (17.7 μmoles) of DMPC (1,2-dimyristoyl-sn-glycero-3-phosphocholine) (commercial supplier, AVANTI POLAR LIPIDS #850345C, Alabaster, AL, USA) together with 3.39 mg (8.8 μmoles) of cholesterol (commercial supplier, SIGMA #C8667, MERCK KGaA, Darmstadt, Germany), 305 μg (200 nmoles) of non-exchangeable head-group labeled fluorescent-tagged phosphatidylethanolamine (1,2-dioleoyl-snglycero-3-phosphoethanolamine-N-(lissamine rhodamine B sulfonyl)); commercial supplier, AVANTI POLAR LIPIDS #810150C), and/or 55.0 µg (100 nmoles) of fluorescent Bodipy cholesterol (23-(dipyrrometheneboron difluoride)-24-norcholesterol); commercial supplier, AVANTI POLAR LIPIDS #810255), from their respective stock solutions in chloroform. The LC-CSH lipid mole ratio is DMPC:Cholesterol:*PE:*Chol=2:1:0.02:0.01. The lipid mixtures were dried under nitrogen. To form LC-CSH, 80 mg of LRA along with 2 mL of saline was added to the dried lipid mixture and then vortexed for 10 min. This lipid to LRA ratio provides sufficient lipid to completely cover the surface of LRA particles, thereby preventing direct lipoprotein binding to non-lipid-coated LRA surfaces. The resulting LC-CSH were pelleted by centrifugation (2000 rpm, 2 min), and the supernatant was removed and replaced with 5 mL of saline. This washing process was repeated 5 times to ensure removal of any potential lipid vesicles not attached to LRA. After the final wash the LC-CSH solution volume was brought up to 2.5 mL in saline. Confocal and transmission electron microscopy reveal the plate and needle crystal structure of LC-CSH particles.

Plasma and serum samples. For analytical validation studies, pooled human plasma and individual HDL-deficient plasma samples were obtained from healthy donors and Familial Lecithin:Cholesterol Acyltransferase Deficiency (FLD) patients, respectively. FLD plasma was stored on ice or at 4° C. prior to use. Lipoprotein-X (LpX), which is diagnostic for FLD, is an abnormal multilamellar lipoprotein that is enriched in phospholipids and free cholesterol. Because plasma LpX is unstable to freeze and thaw cycles, fresh, never-frozen FLD plasma was used in these studies. VLDL, LDL, and HDL subfractions from normal human plasma were obtained by differential ultracentrifugation. For clinical validation studies, individual human serum samples were obtained from CVD patients enrolled in Clinical Trials at the NIH (Clinical Studies I and II) and from Japanese CAD and non-CAD subjects (Clinical Study III). Blood collection was carried out following the rules of the Declaration of Helsinki of 1975, revised in 2013. The NIH study was approved by the National Heart, Lung, and Blood Institute, Institute Review Board. Japanese study was approved by the Ethics Committee of Jichi Medical University. All subjects provided informed consent prior to participation in these studies. Direct labeling of all lipoproteins in whole pooled human plasma was done as follows: 2 µL of *PE in ethanol and then 2 µL of *Chol in ethanol was injected into 200 µL pooled human plasma while vigorously mixing, as previously described (Neufeld, E. B. et al., Biology (Basel), 8, doi:10.3390/biology8030053 (2019), incorporated by reference in its entirety).

HDL-specific phospholipid efflux (HDL-SPE) and non-specific cholesterol efflux capacity (NS-CEC) assay. Standard assay reaction mixture (150 µL total volume): 25 µL of human plasma or serum (or, 25 µL of saline for negative controls), together with 50 µL of LC-CSH and 75 µL of saline were incubated in 96 well plates for 1 hr at 37° C. with shaking (1200 rpm). When increasing plasma volume from 10 to 50 µL, 90 to 50 µL of saline and 50 µL of LC-CSH were added to maintain a total reaction volume of 150 µL. After incubation, donor particles were pelleted via centrifugation (2000 rpm for 2 min). 50 µL of the supernatant was transferred to wells in black 96 well plates along with 50 µL of saline and 100 µL of 1% Triton-X100 in water (1% TX) (commercial supplier, THERMO SCIENTIFIC #28314). After mixing well, fluorescent-tagged PE (*PE) for HDL-SPE and/or fluorescent-tagged cholesterol (*Chol) for NS- CEC were measured by fluorimetry (*PE; 540 nm/600 nm Ex/Em, *Chol; 485 nm/520 nm Ex/Em). All assays were performed in triplicate for analytical validation studies or in duplicate for clinical validation studies.

Figure 11A:
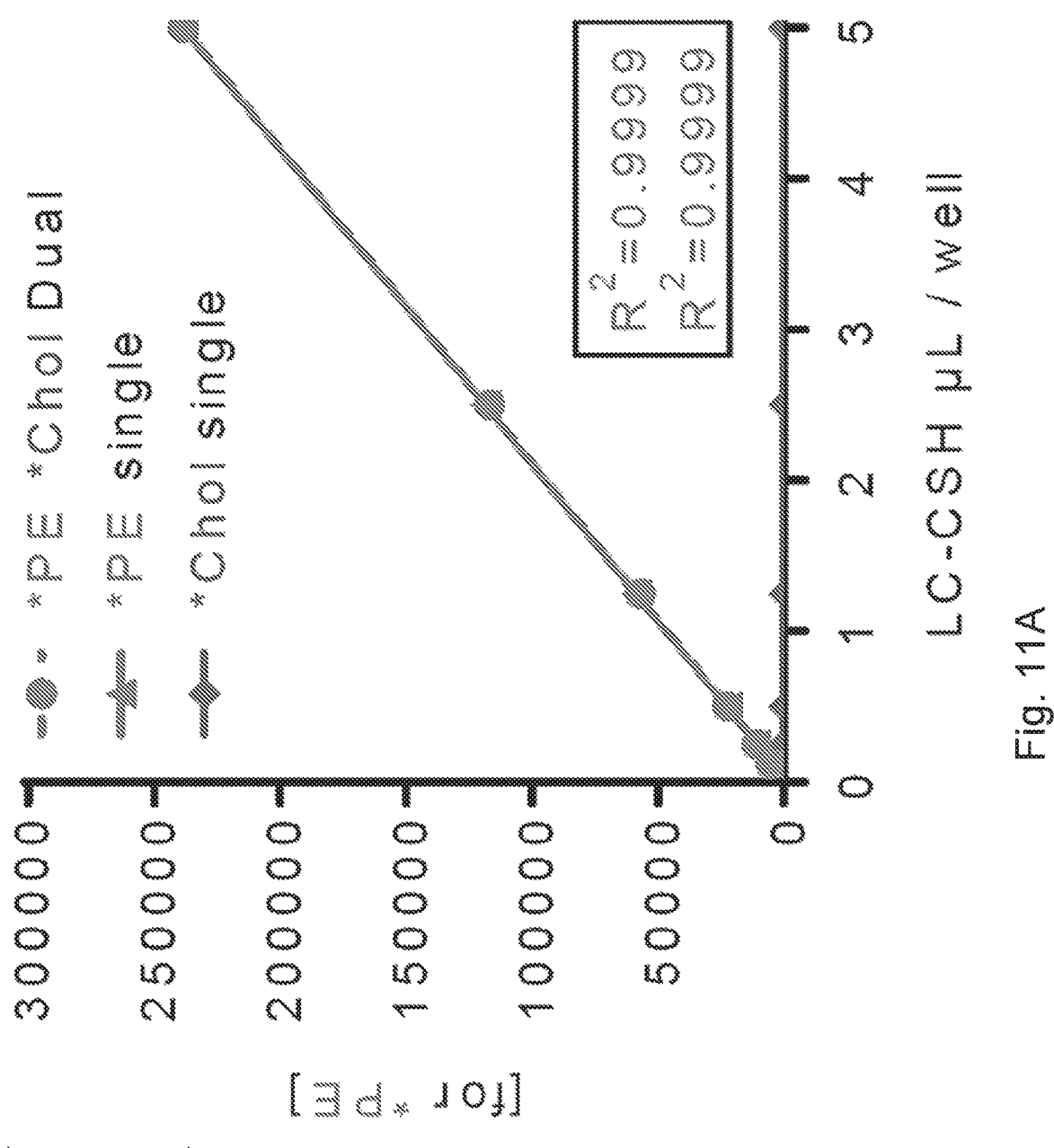
FIG. 11A is a graph showing fluorimetry using 540 nm/600 nm (Ex/Em). FLU=Arbitrary fluorescence units.
Figure 11B:
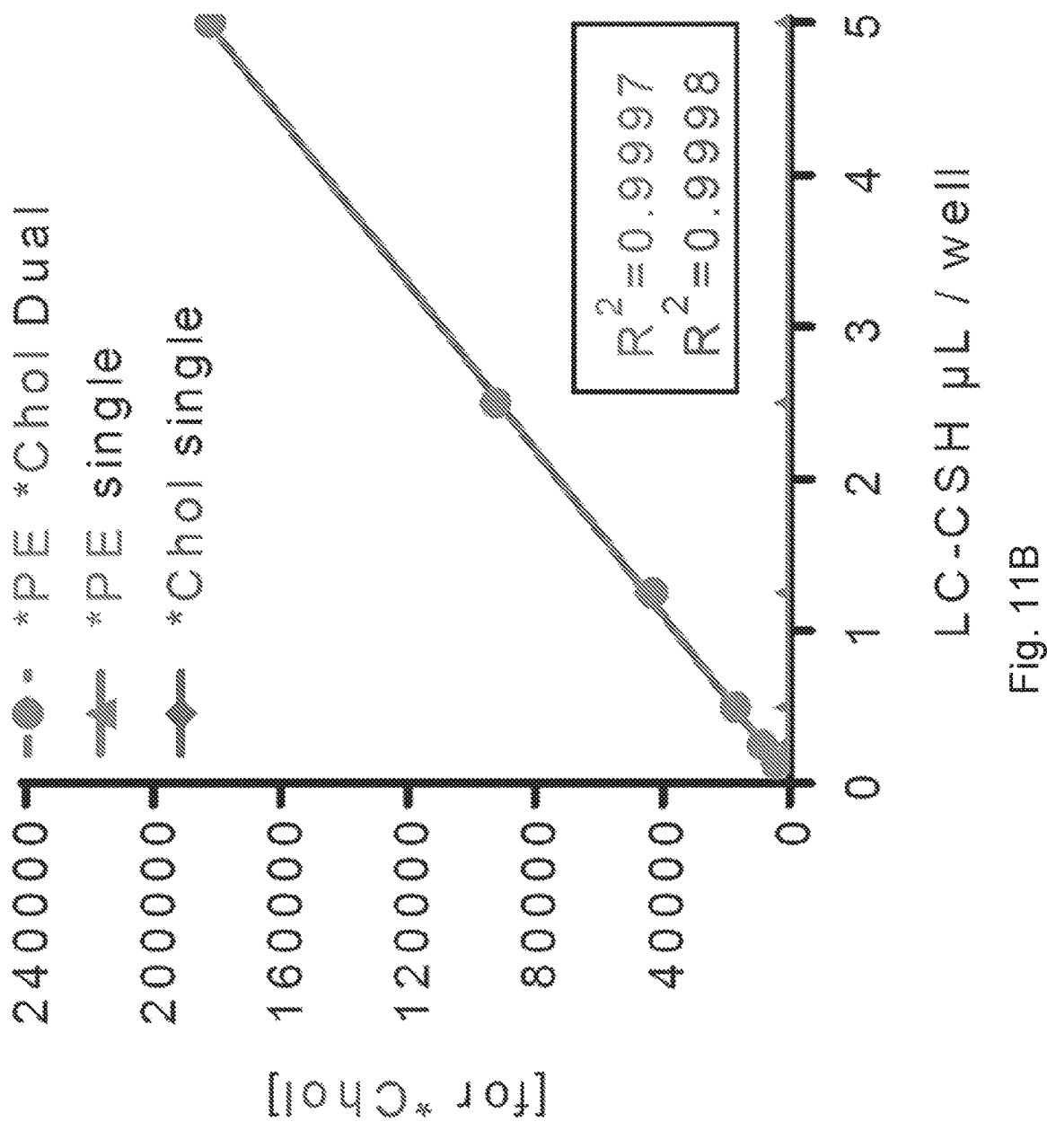
FIG. 11B is a graph showing fluorimetry using 485 nm/520 nm (Ex/Em). FLU=Arbitrary fluorescence units.
Figure 11C:
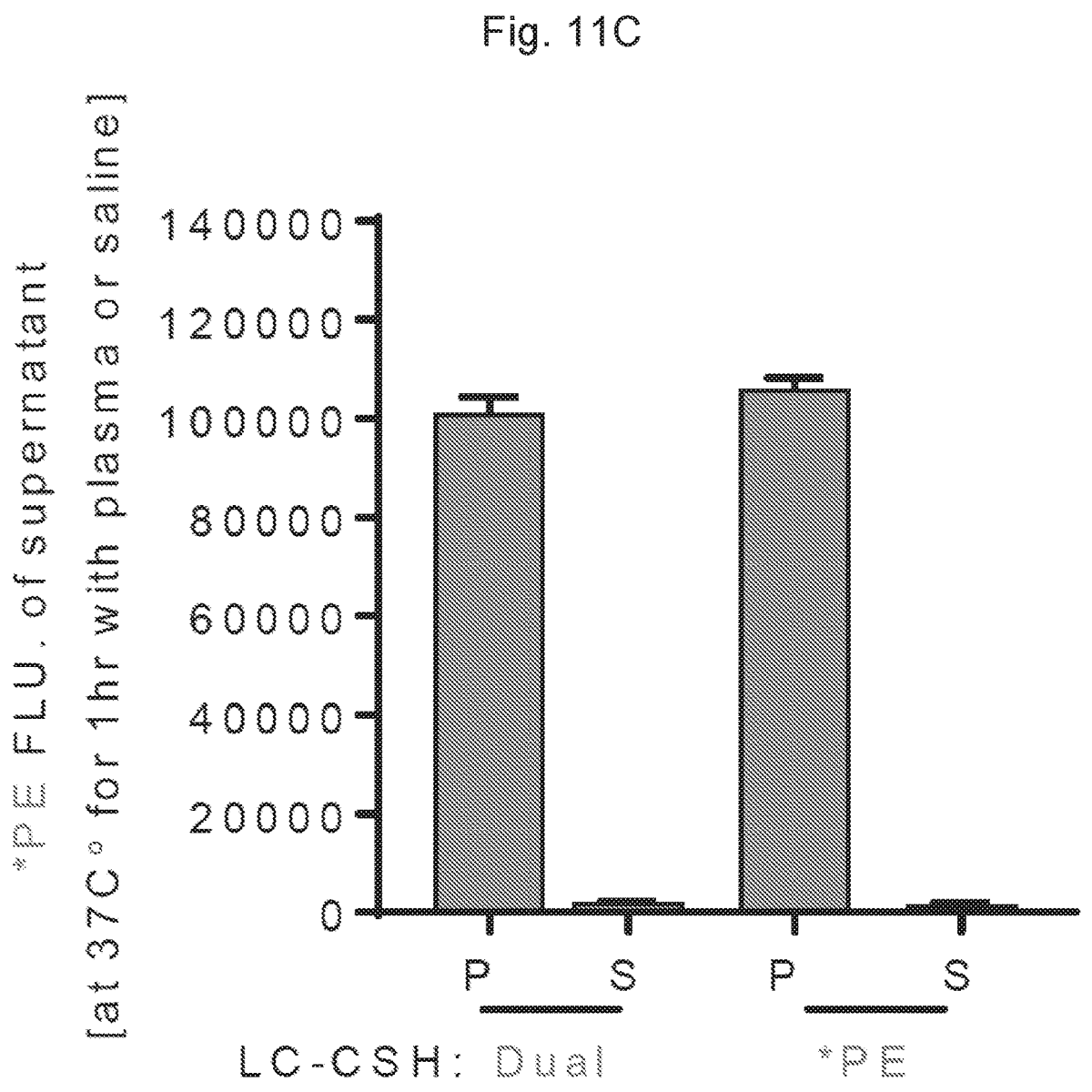
Figure 11D:
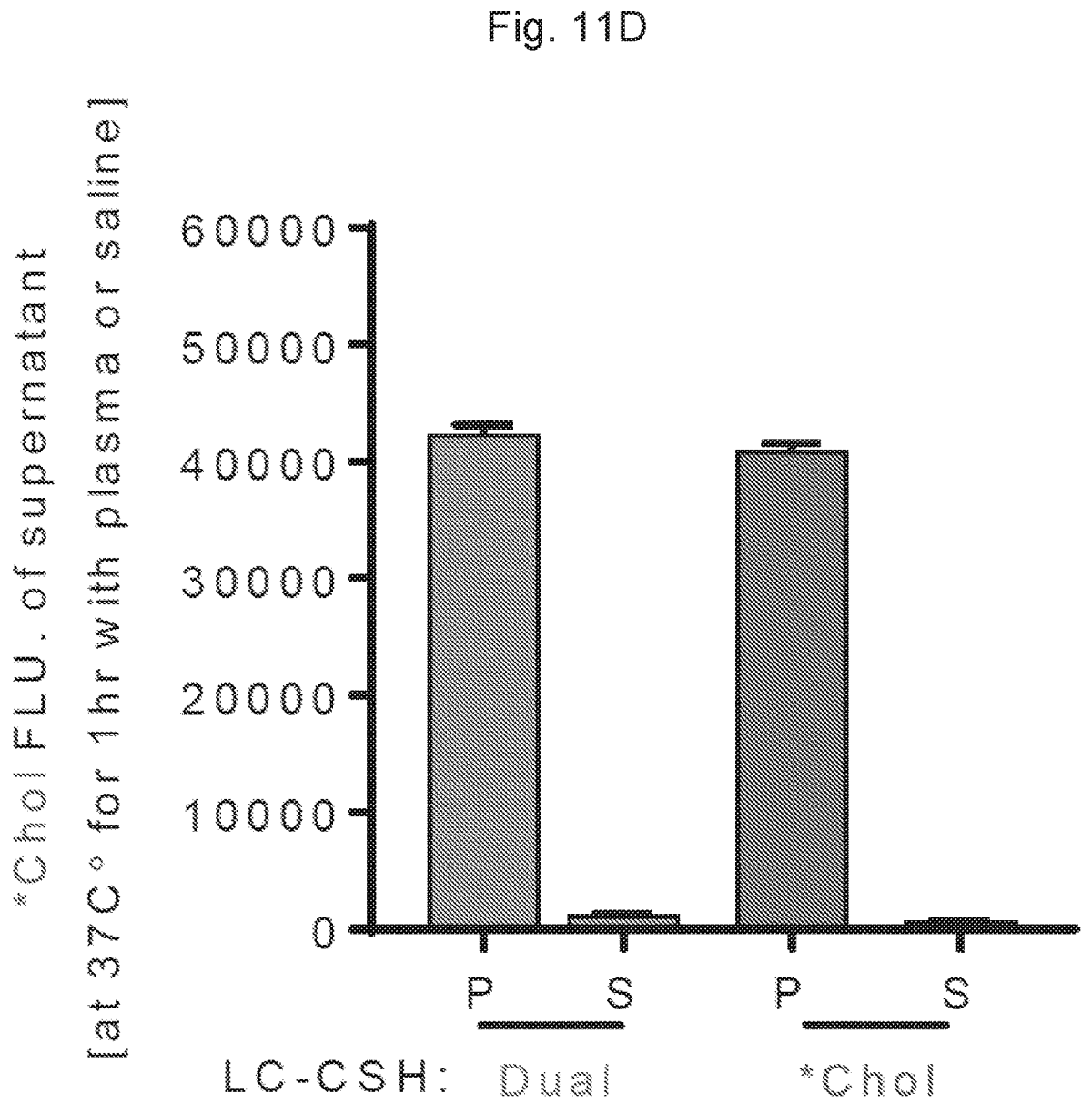

*PE and *Chol standard curves for HDL-SPE and NS-CEC. First, a 10-fold dilution of LC-CSH and a 100-fold dilution of LC-CSH in 15 mL tubes were prepared as follows: 10-fold dilution: 100 µL of LC-CSH and 900 µL of 1% Triton-X100 in water (1% TX); 100-fold dilution: 100 µL of 10-fold diluted LC-CSH and 900 µL of 1% TX. Second, also prepared were six sequential dilutions in 96 well plate using 10-fold dilution and 100-fold dilution as follows: 100 µL of 10-fold dilution+100 µL of 1% TX (equivalent to 10 µL of LC-CSH per well), 50 µL of 10-fold dilution+150 µL of 1% TX (equivalent to 5 µL of LC-CSH per well), 25 µL of 10-fold dilution+175 µL of 1% TX (equivalent to 2.5 µL of LC-CSH per well), 100 µL of 100-fold dilution+100 µL of 1% TX (equivalent to 1 µL of LC-CSH per well), 50 µL of 100-fold dilution+150 µL of 1% TX (equivalent to 0.5 µL of LC-CSH per well), 25 µL of 100-fold dilution+175 µL of 1% TX (equivalent to 0.25 µL of LC-CSH per well). Third, to completely dissolve LC-CSH-bound lipids, the samples were incubated at 24° C. for 1 hour with shaking (1200 rpm). Following this incubation, 100 µL of the entire suspension (including the delipidated CSH particles) was transferred to black 96 well plate wells along with 100 µL of saline. After mixing well, fluorescence of fluorescent-tagged PE (*PE) and/or fluorescent-tagged cholesterol (*Chol) were measured as described above. All assays were performed in triplicate. Note this protocol can provide precise standard curves for *PE ($R^2$=0.9999) and *Chol ($R^2$=0.9997), as shown in FIGS. 11A and 11B (note that LC-CSH (a)*PE fluorescence emission is unaltered in the presence of *Chol and conversely, (b) *Cholfluorescence emission is unaltered in the presence of *PE. In addition, (a)*PE-labeled LC-CSH has no *Chol emission and conversely, (b)*Chol-labeled LC-CSH has no *PE emission). It was confirmed that there is no cross-talk between *PE fluorescence and *Chol fluorescence using *PE singly-labeled LC-CSH and *Chol singly-labeled LC-CSH (FIGS. 11C and 11D). Moreover, no interference in the measurement of either HDL-SPE or NS-CEC was detected when dual *PE- and *Chol-labeled LC-CSH donor particles were used in the assay.

% Efflux calculation for HDL-SPE (*PE) and NS-CEC (*Chol). % *PE or *Chol efflux values were given by ((Supernatant sample FLU−Supernatant saline FLU)/total LC-CSH FLU)×100. Total LC-CSH FLU was calculated using standard curves, as described above. Normalized efflux values were defined as clinical sample % efflux value divided by reference control % efflux value. Identical pooled human plasma from healthy donors with normal lipid profile was used as a reference control. Normalization of efflux values in clinical studies was performed to correct for daily variation in reagent preparation and experimentation. HDL-SPE and NS-CEC assay protocols as well as the % efflux calculation method demonstrated high reproducibility with $R^2$=0.9984 and $R^2$=0.9969 for HDL-SPE and NS-CEC respectively. These reproducibility analyses were conducted using the same batch of materials including LC-CSH.

HDL-SPE assay using isolated lipoproteins (HDL, LDL and VLDL). Isolated HDL phospholipid concentration was adjusted to 80 mg/dL with saline, a previously reported HDL phospholipid concentration in human plasma. In order to compare the specificity of HDL-SPE between lipoproteins, isolated LDL and VLDL were also used at the same phospholipid concentration as HDL phospholipid, specifically, 10 µl (8 µg), 20 µl (16 µg), or 40 µl (32 µg).

Fluorescent Lipid Agarose Gel Electrophoresis. This assay was performed as previously reported (Neufeld, E. B. et al., Biology (Basel), 8, doi: 10.3390/biology8030053 (2019), incorporated by reference in its entirety). Briefly, fluorescent lipoproteins were monitored by electrophoresis of 10 µl of reaction mixture, using SEBIA HYDRAGEL LIPOPROTEIN (E) 15/30 agarose gels (commercial supplier, SEBIA #4134, France), which ran at 100V for 60 min at room temperature. Fluorescent bands on the gel were imaged using a TYPHOON 9400 VARIABLE MODE IMAGER (GE). Lipoprotein labelled with *PE and/or *Chol were detected using excitation/emission wavelengths of 532/560 nm and 488/520 nm, respectively. Following imaging of fluorescent lipids and protein, gels were stained with Sudan Black staining according to manufacturer's instructions and rescanned. Quantitative analysis of fluorescent band intensity was performed using IMAGEQUANT 5.1 software. Individual pixel intensities were normalized to total HDL pixel intensity for each sample.

Cellular-cholesterol efflux capacity assay (C-CEC). The C-CEC assay was performed as previously reported (Gordon, S. M. et al., Atherosclerosis, 278, 278-285, doi: 10.1016/j.atherosclerosis.2018.09.032 (2018), incorporated by reference herein in its entirety). Briefly, J774 cells were plated and radiolabeled with 2 µCi of $^3$H-cholesterol/mL and incubated with cAMP to upregulate ABCA1. PEG precipitated plasma was added to the efflux medium (final concentration 2.8%) for 4 hours. Efflux was calculated by using the following formula (µCi $^3$H-cholesterol):((3H-cholesterol in subject's plasma)–($^3$H-cholesterol in plasma-free media)/ (3H-cholesterol in media containing reference plasma pool)–($^3$H-cholesterol in plasma-free media)). The pooled human plasma was obtained from healthy volunteers. All assays were performed in duplicate.

Assessment of LC-CSH-bound and released plasma proteins. To allow binding of plasma proteins to LC-CSH particles, 25 µL of pooled human plasma (or saline), 50 µL of LC-CSH and, 75 µL of saline were incubated for 30 min at 37° C. with shaking at 1200 rpm. 120 µL of supernatant was removed and replaced with 120 µL of new cold saline. After pipetting vigorously 5 times, LC-CSH was precipitated by centrifugation (2000 rpm for 2 min), and 120 µL of the supernatant was removed and replaced with 120 µL of new cold saline. This procedure was repeated for a total of five washes. All washing procedures were performed at 4° C. It was determined that five washes were sufficient to eliminate unbound plasma proteins (see below). The final saline supernatant wash was removed and 120 µL saline was added to the washed LC-CSH pellet (30 µL volume) so that the total final reaction mixture volume was 150 µL. Plasma proteins bound to LC-CSH were then allowed to be released into saline by incubating the mixture for 1 hr at 37° C. with shaking at 1200 rpm. For In-solution digest (FIGS. 14C-14E), proteins in the supernatant were concentrated via speed-vac to obtain sufficient protein mass for LC-MS/MS analyses. For fluorescent lipid gel electrophoresis, *PE labeled-HDL in the supernatant was concentrated by centrifugation (10,000 rpm, 45 min) using a 3K filter (commercial supplier, MILLIPORE #UFC500324) in order to enhance the *PE intensity to allow for gel analysis.

Assessment of the efficacy of removal of unbound plasma proteins from LC-CSH by fluorimetry and SDS-PAGE electrophoresis. 25 µL of pooled human plasma, 50 µL of LC-CSH and, 75 µL of saline were incubated for 30 min at 37° C. with shaking at 1200 rpm. 120 µL of supernatant was removed and replaced with 120 µL of new cold saline. After pipetting vigorously 5 times, LC-CSH was precipitated by centrifugation (2000 rpm for 2 min), and 120 µL of the supernatant was removed and replaced again with of 120 µL of new cold saline. This washing process was repeated up to ten times. All washing procedures were performed at 4° C. *PE fluorescence in the supernatant (*PE not bound to LC-CSH) was reduced to the same level as saline background level after five washes, even after LC-CSH was pre-incubated for 240 min with human plasma. To confirm the stability of plasma protein binding to LC-CSH after 30 min pre-incubation with pooled human plasma, samples were prepared for SDS-PAGE electrophoresis as follows: 50 µL of lysis buffer (2% SDS, 10 mM DTT in 50 mM triethylammonium bicarbonate buffer pH8.5) was added to washed (1-10 times) and to unwashed LC-CSH as well as 1 µL of pooled human plasma, as reference controls. Samples were extracted and denatured for 5 min at 95° C. with shaking at 600 rpm in lysis buffer. 30 µL of the lysate was obtained from supernatant and incubated with 10 µL of 4×NUPAGE sample buffer (commercial supplier, INVITROGEN #NP0007, Carlsbad, CA, USA) for 5 min at 95° C. 40 µL of each sample was loaded on to NOVEX NUPAGE 4-12% Bis-Tris Gel 1.5 mm (commercial supplier, INVITROGEN #NP0335) and run with NUPAGE MOPS running buffer (commercial supplier, INVITROGEN #NP0001) at 200V for 50 min at room temperature, SEEBLUE PLUS2 prestained standard (commercial supplier, INVITROGEN #LC5925) was used as a protein size marker. After gel electrophoresis, protein bands were stained for 30 min with Coomassie Brilliant Blue (CBB: 1 g of R-250, 400 mL of methanol, 100 mL of acetic acid and 500 mL of double distilled water) and then de-stained overnight (200 mL of methanol, 100 mL of acetic acid and 700 mL of double distilled water). After five or more saline washes, apoA-I bands on the gel remained unaltered whereas albumin and other protein bands were reduced to a minimum compared to unwashed controls. ApoA-I and albumin were identified by in-gel proteomic analysis (not shown). These findings indicate that five washes optimally remove contaminating supernatant proteins and *PE, thus allowing for the proteomic analysis of LC-CSH-bound and released plasma proteins associated with*PE efflux.

In-gel proteomic analysis. Eluted plasma proteins that were bound to LC-CSH were subjected to SDS-PAGE, and gels were stained with CBB. Protein bands were excised, then destained, reduced, alkylated and digested overnight with trypsin (commercial supplier, PROMEGA, V511A Sequencing grade; Madison, WI, USA). Digested peptides were desalted, concentrated and purified using C18 ZipTips according to the manufacturer's protocol (ZTC18S096, MILLIPORE SIGMA, MERCK KGaA, Darmstadt, Germany) and transferred into sample vials (C4011-13, THERMO SCIENTIFIC, Waltham, MA, USA) for mass spectrometry.

In-solution proteomic analysis. Whole plasma proteins, LC-CSH-bound-proteins and concentrated LC-CSH-released proteins were solubilized in 100 µL of lysis buffer (7M Urea/2M thiourea in 50 mM TEAB). Bradford protein assay (23200, THERMO SCIENTIFIC PIERCE) was used to measure the protein concentrations for each sample. 40 µg of total protein from each sample were delipidated and concentrated using chloroform/methanol procedure adapted from a previous report (Wessel, D. & Flugge, U. I., Anal Biochem, 138, 141-143, doi: 10.1016/0003-2697 (84) 90782-6 (1984), incorporated by reference herein in its entirety). Delipidated protein precipitates were resuspended in 100 μL of 100 mM triethylammonium bicarbonate (TEAB), then reduced, alkylated and digested overnight with trypsin. Digested peptides were desalted, concentrated and purified using high capacity C18 tips according to the manufacturer's protocol (87784, THERMO SCIENTIFIC PIERCE) and transferred into sample vials for mass spectrometry.

Mass Spectrometry. All mass spectrometry experiments were performed in replicates on an ORBITRAP LUMOS TRIBRID coupled with an ULTIMATE 3000-nLC (commercial supplier, THERMO FISHER SCIENTIFIC). Peptides were separated on an EASY-Spray C18 column (commercial supplier, THERMO SCIENTIFIC; 75 μm×50 cm inner diameter, 2 μm particle size and 100 Å pore size). Separation was achieved by 4-35% linear gradient of acetonitrile+0.1% formic acid over 125 min. An electrospray voltage of 1.9 kV was applied to the eluent via the EASY-Spray column electrode. The ORBITRAP LUMOS was operated in positive ion data-dependent mode. Full scan MS1 was performed in the ORBITRAP with a normal precursor mass range of 380-1,500 m/z at a resolution of 120 k. The automatic gain control (AGC) target and maximum accumulation time settings were set to $4×10^5$ and 50 ms, respectively. MS2 was triggered by selecting the most intense precursor ions above an intensity threshold of 2.5× $10^4$ for collision-induced dissociation (CID)-MS2 fragmentation with an AGC target and maximum accumulation time settings of $5×10^4$ and 50 ms, respectively. Mass filtering was performed by the quadrupole with 0.7 m/z transmission window, followed by CID fragmentation in the ORBITRAP and a normalized collision energy (NCE) of 35% at a resolution of 15 k. To improve the spectral acquisition rate, parallelizable time was activated. The number of MS2 spectra acquired between full scans was restricted to a duty cycle of 3 s.

Data Processing. Raw data files were processed using *Andromeda* integrated in MaxQuant (v1.6.2.10, Max Planck Institute of Biochemistry). All the peak lists were searched against the UniProtKB/Swiss-Prot protein database released 2019_04 with *Homo sapiens* taxonomy (20,316 sequences) and concatenated with reversed copies of all sequences. The following search parameters were set for MS1 tolerance of 10 ppm; orbitrap-detected MS/MS mass tolerance of 20 ppm; enzyme specificity was set as trypsin with maximum two missed cleavages; minimum peptide length of 7 amino acids; carbamidomethylation of cysteine was set as a fixed modification; and oxidation of methionine was set as a variable modification. Data were filtered to a 10% false discovery rate (FDR) on PSMs estimated using the decoy hit distribution. To calculate the approximate abundance of each protein, the intensity based absolute quantification, or iBAQ algorithm, was used, provided in MaxQuant. iBAQ is the sum of the extracted ion intensities of all identified peptides per protein, normalized by the number of theoretically observable peptides of the protein. These normalized protein intensities are translated to protein copy number estimates based on the overall protein amount in the analyzed sample.

Native gel analysis. An equal volume of NOVEX TRIS-GLYCINE NATIVE SAMPLE BUFFER (2×) (commercial supplier, THERMO FISHER SCIENTIFIC) was added to each sample and 20.0 μl was immediately loaded onto NOVEX native 10-20% Tris-Glycine WEDGEWELL mini-gels, 1.0 mm thick (commercial supplier, THERMO FISHER SCIENTIFIC). AMERSHAM HMW CALIBRA-TION KIT FOR NATIVE GEL ELECTROPHORESIS (Catalog #17-0445-01 GE HEALTHCARE Piscataway, NJ, USA) was used for the HDL size marker (8.16 nm, 9.7 nm, 12.2 nm and 17 nm). Gels were run at 35V for 17 hours and fluorescent bands were imaged using a TYPHOON 9400 VARIABLE MODE IMAGER (GE) and *PE was detected using excitation/emission wavelengths of 532/560 nm.

Confocal microscopy. Structured Illumination Microscope (SIM) mages were acquired with a VT-iSIM IMAG-ING SYSTEM scanner from VISITECH INTERNA-TIONAL (Sunderland, UK) on an OLYMPUS IX 81 microscope using an OLYMPUS UPLSAPO 100×1.49 NA Oil objective and dual HAMAMATSU CMOS ORCA-FLASH 4 cameras. The total acquisition system was controlled using METAMORPH software (MOLECULAR DEVICES, LLC, San Jose, CA, USA). The *PE and *Chol fluorescence were excited with 561 nm and 488 nm lasers, respectively, and the emission light was filtered using a long pass 590 nm, and, 500-550 nm emission filters, respectively, before the camera. 3D volumes were taken at an interslice distance of 100 nm for a total of 30-36 individual planes. Exposure time for each plane was 250 ms.

Electron microscopy. Thin section TEM: LC-CSH particles were mixed with 10% liquefied low-melting point agarose and then solidified on ice. The embedded LC-CSH were maintained at 4° C. overnight and then fixed in 2.5% glutaraldehyde/1% paraformaldehyde in 0.12 M sodium cacodylate buffer (pH 7.4) at 4° C. overnight. Fixed samples were washed in cacodylate buffer, post-fixed in 1% OsO4 in cacodylate buffer, washed, stained en bloc with uranyl acetate, ethanol dehydrated, and EMbed-812 embedded ELECTRON MICROSCOPY SCIENCES, Hatfield, PA, USA). Thin sections were stained with uranyl acetate and lead citrate prior to imaging with a JEM1400 electron microscope (JEOL USA, Peabody, PA, USA) equipped with an AMT XR-111 digital camera (ADVANCED MICROS-COPY TECHNIQUES CORP, Woburn, MA, USA). Nega-tive staining: LC-CSH particles were diluted to 0.6 mg/ml with PBS sample buffer. 3 μl of sample solution was placed on each FCF300H-CU (ELECTRON MICROSCOPY SCI-ENCES, PA, USA) grid and left at room temperature for 1 minute. Grids were subsequently blotted using filter paper, washed with filtered distilled water three times and then stained with uranyl acetate 2% (ELECTRON MICROS-COPY SCIENCES) for 20 seconds. Grids were then blotted with filter paper to remove excess stain and left to dry at room temperature for 15 minutes. Samples were evaluated by FEI Tecnai T12 120 kV TEM & 2 k TVIPS camera.

Atherosclerosis burden assessment. Coronary CT scans were performed using a 320-detector row AQUILION ONE VISION system (TOSHIBA). Coronary plaque burden was separately evaluated in each of the main coronary arteries (left anterior descending, left circumflex, and right coronary arteries) using the dedicated software QANGIO CT (ME-DIS) by a single blinded reader as previously reported (Gordon, S. M. et al., Atherosclerosis 278, 278-285, doi: 10.1016/j.atherosclerosis.2018.09.032 (2018)). Plaque vol-ume index (mm²) was calculated by dividing total vessel plaque volume by total vessel length and was adjusted for luminal attenuation. Total plaque burden was defined as the sum of calcified plaque burden and non-calcified plaque burden.

Clinical study populations. Clinical Study I, II and III included 84, 76, and 217 subjects, respectively. For clinical study I, the sera used in the US cohort study included 84 cardiovascular disease (CVD) patients, recruited as part of an ongoing cohort study (#12-H-0141) as previously reported (Gordon, S. M. et al., *Atherosclerosis* 278, 278-285, doi:10.1016/j.atherosclerosis.2018.09.032 (2018)). For Clinical Study II, an additional 76 CVD subjects from Protocol #12-H-0141 were included. Severe CAD cases (n=40) and well-matched non-CAD (n=36) were recruited. Severe CAD was defined as patients with total coronary occlusion based on the angiographical results (CAD-RADS 5) and non-CAD was defined as persons with no significant stenosis or minimum stenosis (CAD-RADS 0 or CAD-RADS 1). These subjects (Clinical Study I and II) included both males and females that were at least 18 years of age and with clinical indication for a coronary CT angiography (CCTA) exam and no additional inclusion criteria. These studies protocol was approved by the National Heart, Lung, and Blood Institutional review board and all subjects provided informed consent at enrollment. ClinicalTrials.gov identifier: NCT01621594. For Clinical Study III, as an additional ethnic group study, 217 subjects of a Japanese cohort, consisting of CAD cases (n=63) and non-CAD (n=154), were included. These subjects included both males and females that were at least 20 years of age with, or at risk for, lifestyle-related diseases, with no additional inclusion criteria. CAD was evaluated based on coronary angiography. This study protocols (C17-R007, 122, 142 and 158) were approved by the Ethics Committee of Jichi Medical University and all subjects provided informed consent at enrollment.

Statistical analyses. Skewness and kurtosis measures were used to assess normality. Data were represented as mean±standard deviation, or, median (interquartile range), for parametric and non-parametric variables, respectively, and as n (%) for categorical variables. P-values were derived from a single unpaired 2-tailed t-test for parametric variables and Mann-Whitney test for non-parametric variables. Fisher exact test was used for categorical variables. The relationship between two variables was evaluated by a scatterplot using Pearson's correlation coefficient with the 95% confidence interval and P-values. Bivariate or multivariate linear regression analyses were performed to assess the relationship between HDL efflux values (C-CEC or HDL-SPE) and clinical and laboratory parameters including CCTA plaque parameters. Non-normally distributed data were log-transformed. Traditional risk factors such as age, gender, BMI, systolic blood pressure, lipid parameters, hs-CRP, lipid-lowering therapy, hypertension and diabetes mellitus were included for multivariate linear regression analyses depending on their availability in each clinical study. Results were reported as standardized R coefficient with the 95% confidence interval and P values. To evaluate the association of HDL-proteins with HDL-SPE or C-CEC, partial least squares regression (PLSR) analysis was performed using the pls package in R as previously reported (Gordon, S. M. et al., Atherosclerosis 278, 278-285, doi:10.1016/j.atherosclerosis.2018.09.032 (2018)). Proteins were ranked according to their variable importance for projection (VIP) scores and the strongest relationship was defined as VIP≥1.3. In Clinical Study II, controls were well-matched in race, gender, body mass index, type 2-diabetes mellitus, current smoker, triglycerides, HDL-related parameters (plasma HDL cholesterol, HDL particle number, HDL-size and apoA-I), NMR parameters (LDL particle number, LDL size, VLDL particle number and VLDL-size), plasma apo-B, hs-CRP level and coronary artery bypass grafting (CABG), but not in age, agatston score, lipid-lowering therapy and LDL cholesterol. Receiver operating characteristic (ROC) curve analyses were conducted to evaluate the contribution of HDL-C or C-CEC or HDL-SPE to the discriminatory power of CAD patients. Data were represented as area under the curve (AUC) with the 95% confidence interval. The optimal cutoff point providing the best pair of sensitivity and specificity was calculated by the lowest distance to the top-left corner of the ROC curve. Bivariate or multivariate logistic regression analyses were used to assess crude odds ratios or adjusted odds ratios of CAD for standard deviation increment in each HDL-C, C-CEC, or HDL-SPE. Traditional risk factors were included for adjustment as described above. In all analyses, P-value<0.05 was considered statistically significant. Statistical analysis was performed using Stata/IC 12.0 (StataCorp LP, College Station, TX, USA) and EZR version 1.40 (Jichi Medical University, Tochigi, Japan). EZR is an improved version of the R commander utility and included in the softpedia software database with "100% CLEAN" software award (softpedia.com/get/Science-CAD/EZR.shtml).

Results

Development of a cell-free phospholipid efflux assay. It was previously shown that apoA-I solubilized lipids from non-exchangeable head-group-tagged lissaminerhodamine phosphatidylethanolamine (*PE)- and Bodipy-cholesterol (*Chol)-labeled lipid vesicles to form pre-β-HDL-like particles containing *PE, *Chol, and apoA-I, and that vesicle-derived *PE specifically incorporated into plasma HDL both in vitro and in vivo. Based on these findings, the HDL-SPE assay was developed in which lipid-coated calcium silicate hydrate crystals (LC-CSH) served as a donor of fluorescent *PE to plasma HDL and can be readily separated from plasma at the end of the reaction by centrifugation. Besides the fluorescent tagged lipids, the LC-CSH were coated with the dimyristoylphosphatidylcholine and cholesterol in a 2:1 ratio, which was found to promote the lipid efflux process.

Figure 12A:
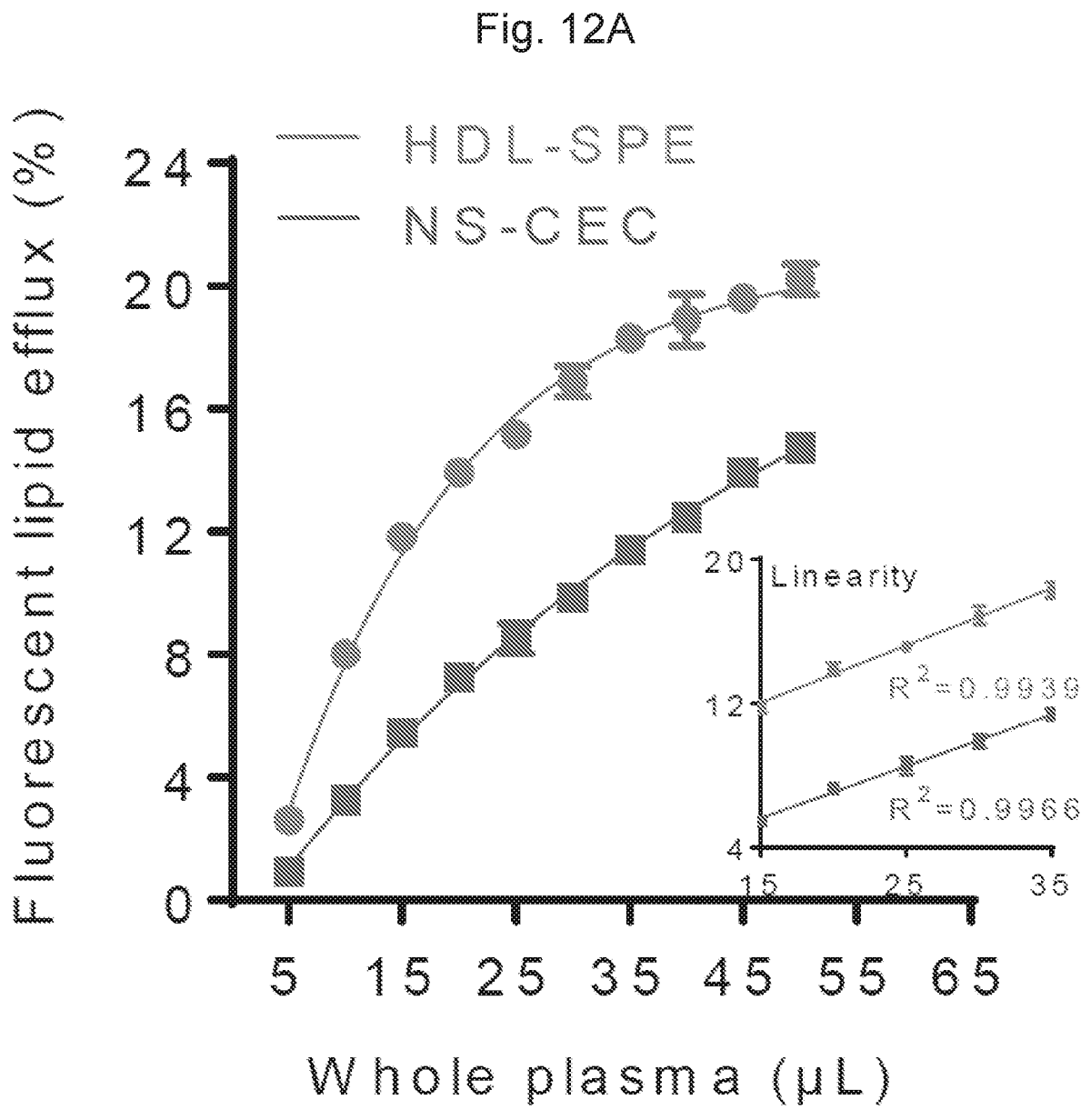
Figure 12B:
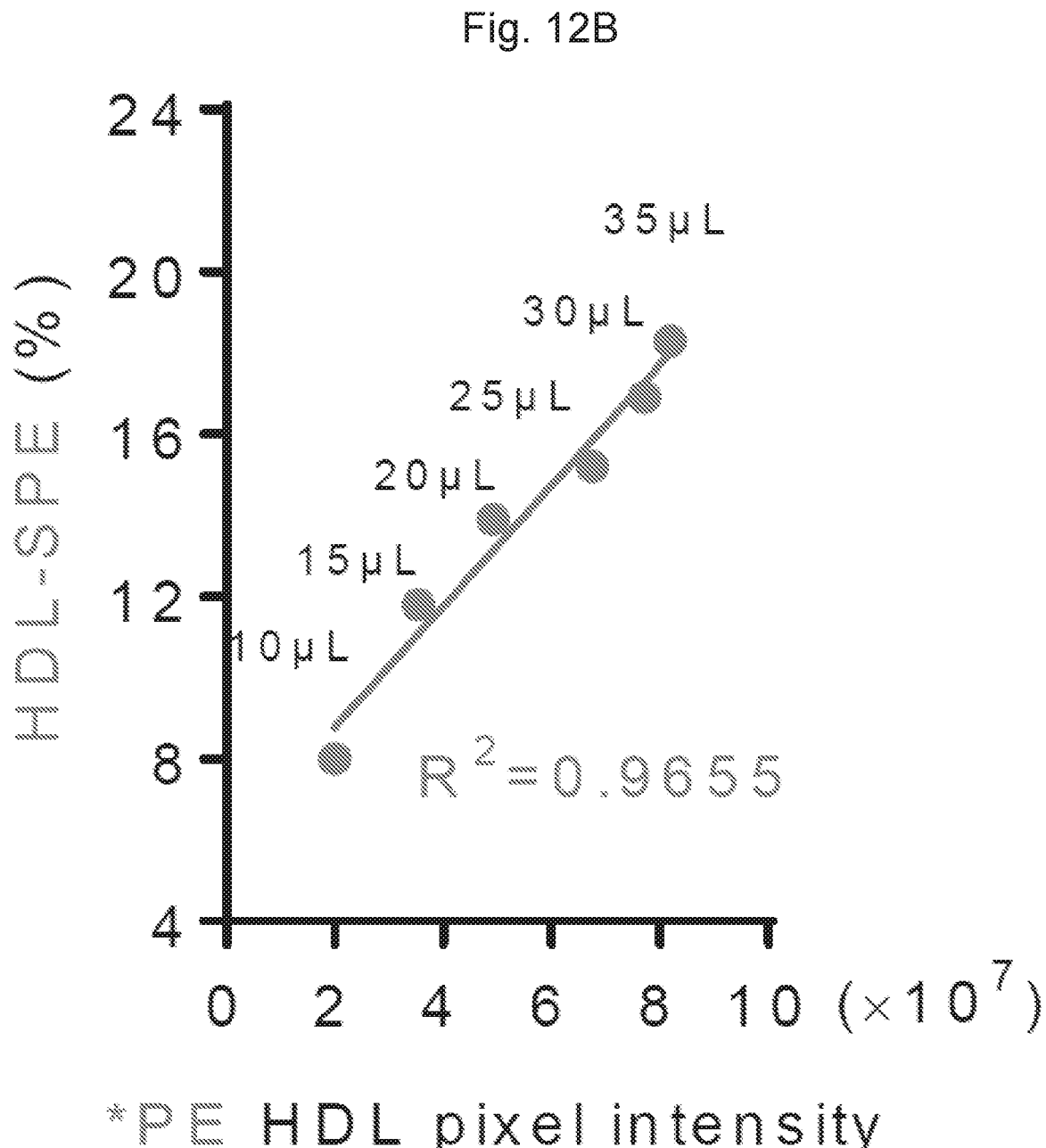
FIG. 12B is a graph showing that fluorometric and electrophoretic gel analyses of HDL-SPE highly correlate. All data are mean±SD in triplicate assays.
Figure 12C:
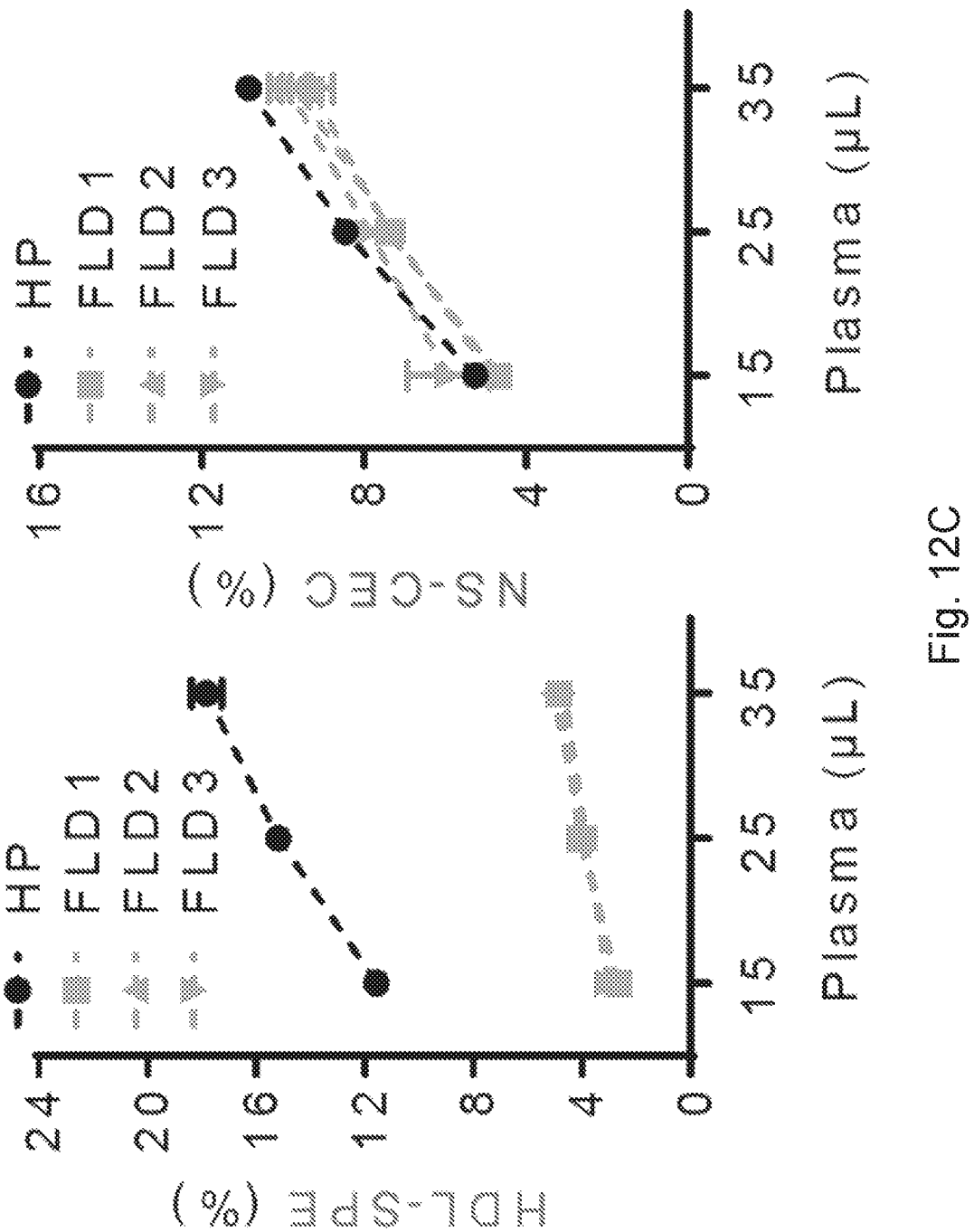
FIG. 12C presents graphs showing that substantial *PE transfers from donor particles to HDL in HP, but not in FLD plasma.
Figure 12D:
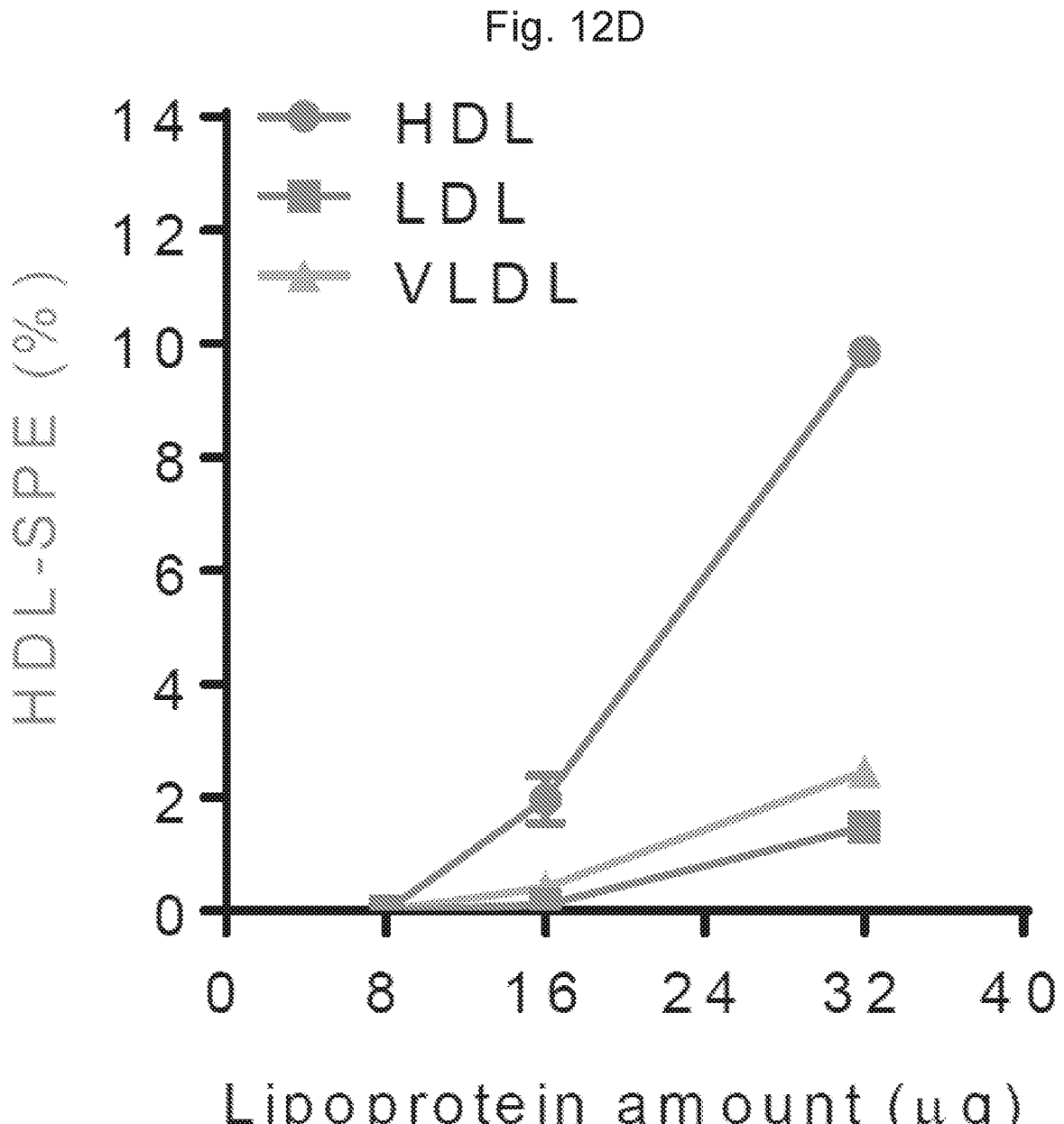
FIG. 12D is a graph showing that LC-CSH *PE effluxes to isolated HDL but not to LDL or VLDL. Various amounts of HDL, LDL, or VLDL were incubated with LC-CSH in saline.
Figure 13:
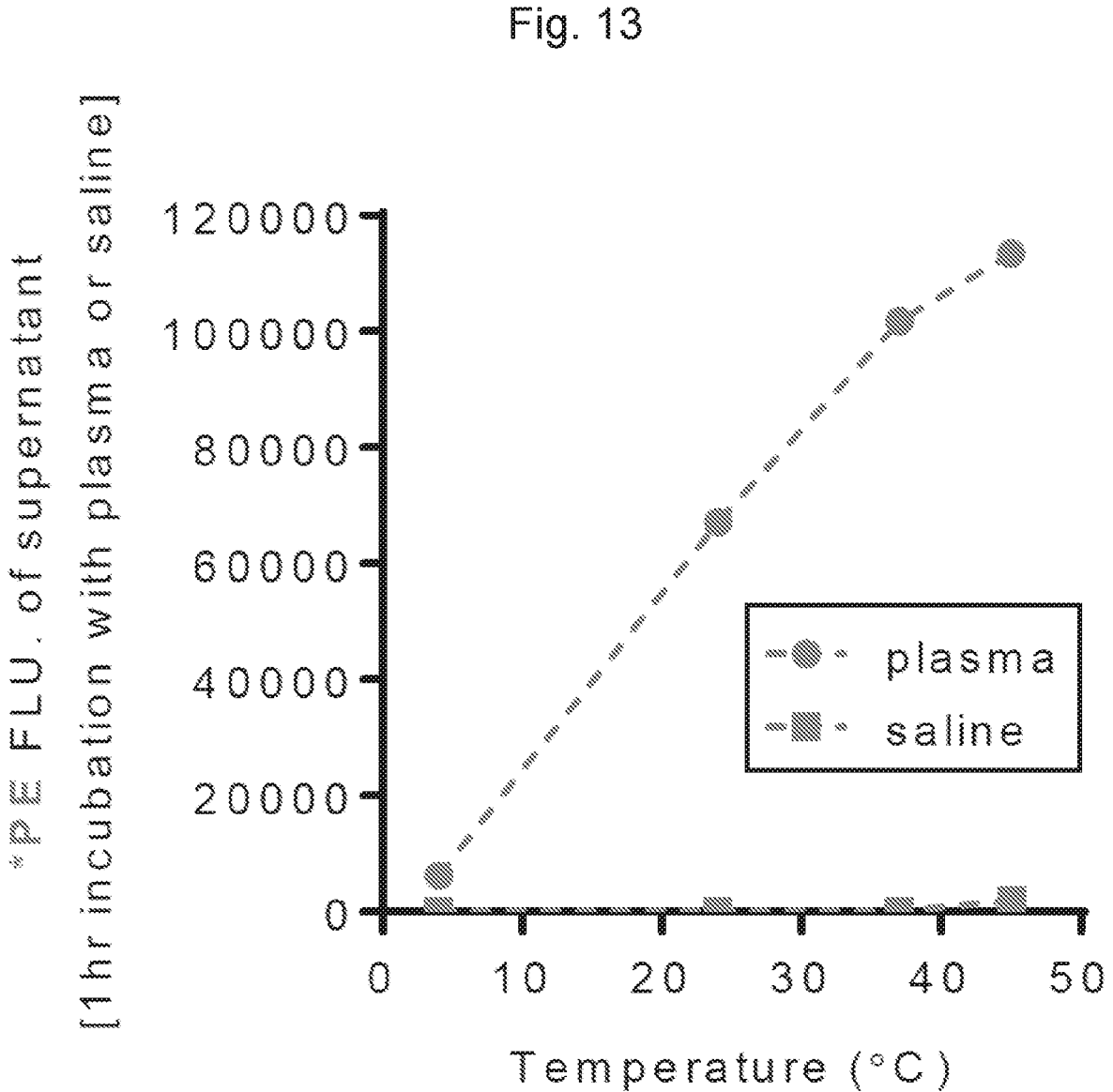
FIG. 13 is a graph showing that HDL-SPE is temperature-dependent. Pooled human plasma or saline were incubated with fluorescent lipid labeled LC-CSH using standard HDL-SPE assay conditions. FLU=fluorescence units. Note that *PE efflux to plasma is linear from 4° C. to 37° C. All data are mean±SD in triplicate assays.

Herein, the apoA-I/HDL-specificity of phospholipid efflux from LC-CSH to lipoproteins in whole human plasma, using a high-throughput HDL-SPE assay is provided. HDL-SPE was (i) dependent on plasma volume (FIG. 12A), (ii) highly correlated with HDL *PE pixel intensity on agarose gels (FIG. 12B), (iii) was markedly reduced in the plasma of Familial Lecithin:Cholesterol Acyltransferase Deficiency (FLD) patients in which HDL is nearly absent (FIG. 12C), and (iv) was largely specific to isolated HDL, but not isolated LDL or VLDL (FIG. 12D). At low plasma sample volumes, HDL-SPE dependence was linear but showed saturation at higher concentrations. HDL-SPE saturation is likely due to the saturation of binding sites for HDL proteins on the surface of LC-CSH, as will be shown below. HDL-SPE is temperature-dependent and therefore an energy-dependent process (FIG. 13), consistent with binding and release of HDL components. In contrast, non-specific cholesterol efflux capacity (NS-CEC) was more linear and did show significant saturation at the doses tested (FIG. 12A). Furthermore, NS-CEC in normal and FLD plasma was nearly identical unlike HDL-SPE (FIG. 12C). These findings suggest that different mechanisms underlie HDL-SPE and NS-CEC, namely, apoA-I/HDL-mediated binding and removal of donor particle *PE vs diffusion of donor particle *Chol to all plasma lipoproteins, respectively.

Figure 14A:
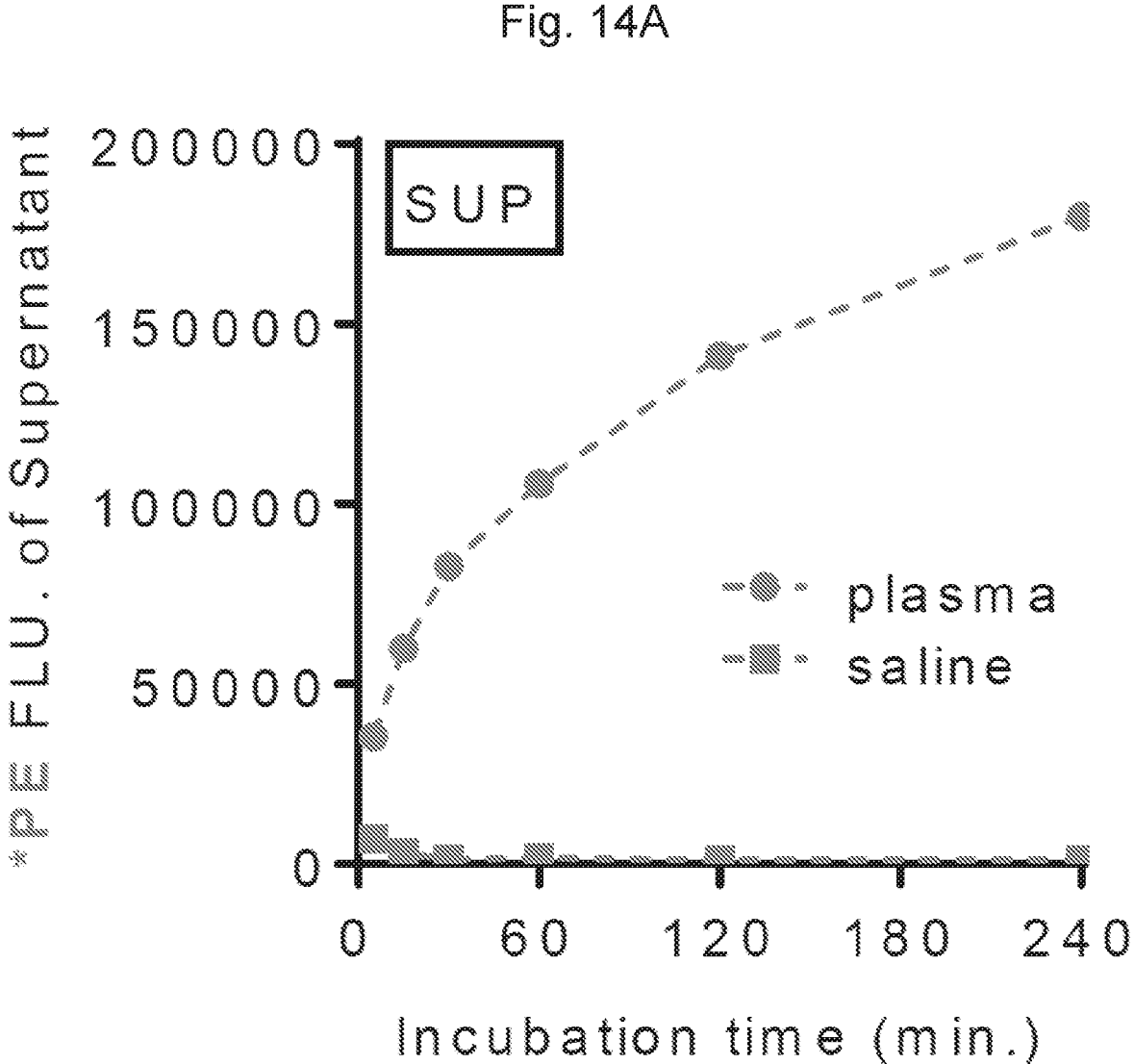
FIG. 14A is a graph showing a time course of LC-CSH *PE efflux to HP vs saline after incubation at 37° C. for indicated times.
Figure 14B:
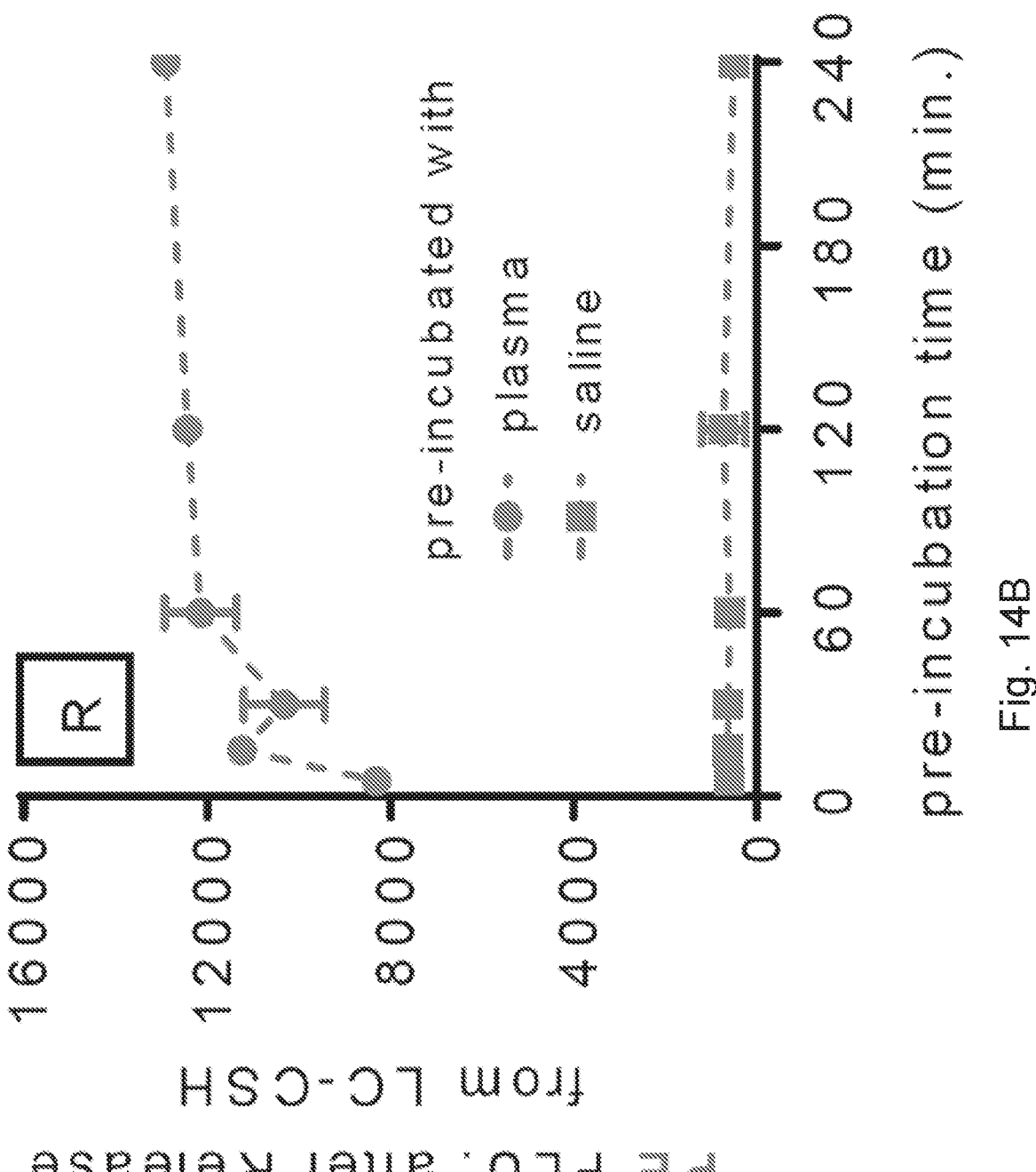
FIG. 14B is a graph showing release of *PE from LC-CSH in FIG. 18A, after washing and subsequent incubation with saline at 37° C. for 1 hr.
Figure 14C:
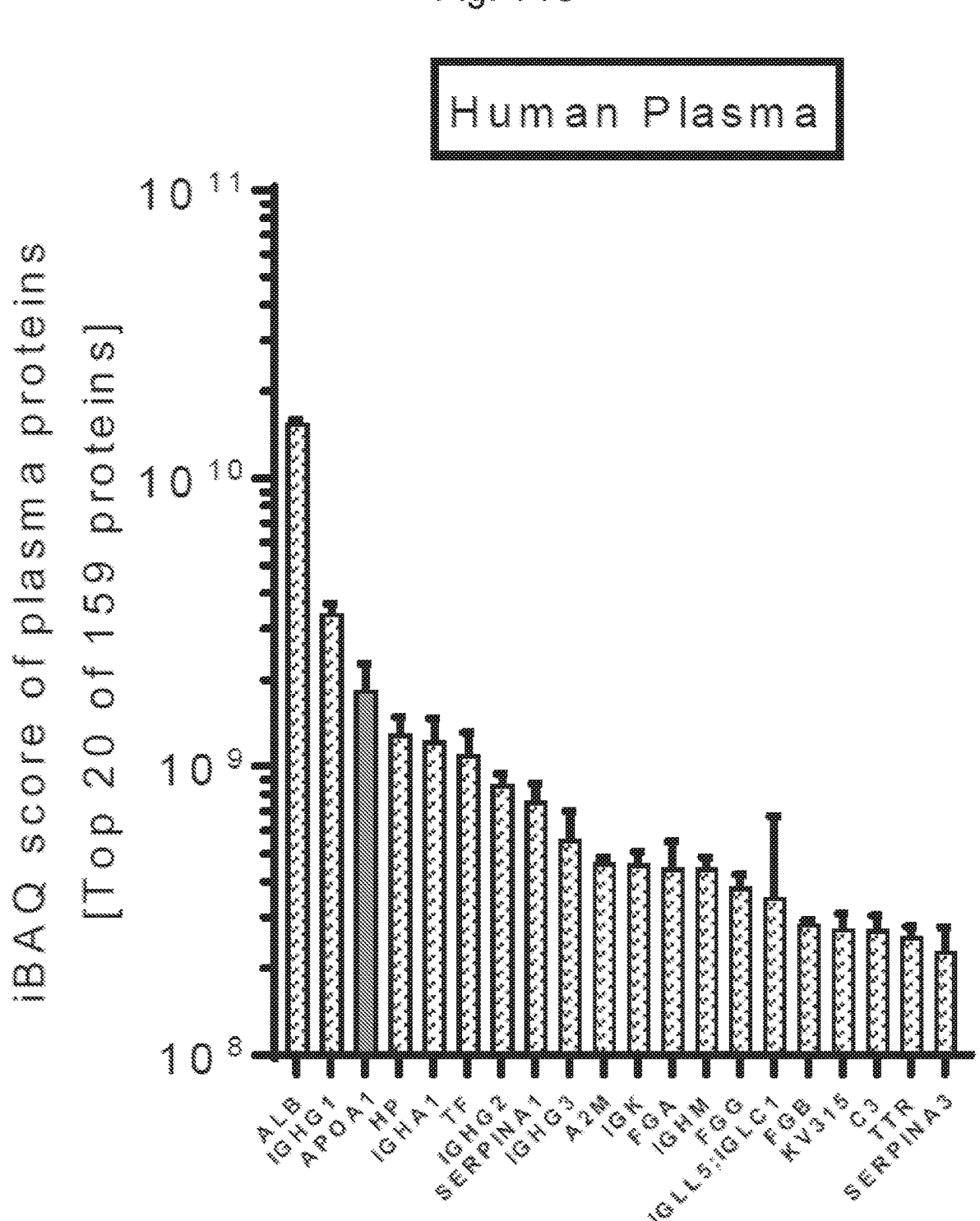
FIGS. 14C-14E are graphs showing that intensity based absolute quantification (iBAQ) analyses reveal the relative distribution of identified plasma proteins. HP proteins (14C), LC-CSH-bound proteins (14D), and LC-CSH-released proteins (14E). The middle inset includes the iBAQ ranking of apolipoproteins among plasma and LS-CSH bound proteins. The % of apolipoprotein in HP or in the LS-CSH-bound fraction are shown in parenthesis (14D inset). The 14E inset includes the iBAQ ranking of apolipoproteins among the LC-CSH-bound and LC-CSH-released proteins. The % of apolipoprotein in LCCSH-bound and LC-CSH-released proteins are shown in parentheses.
Figure 14D:
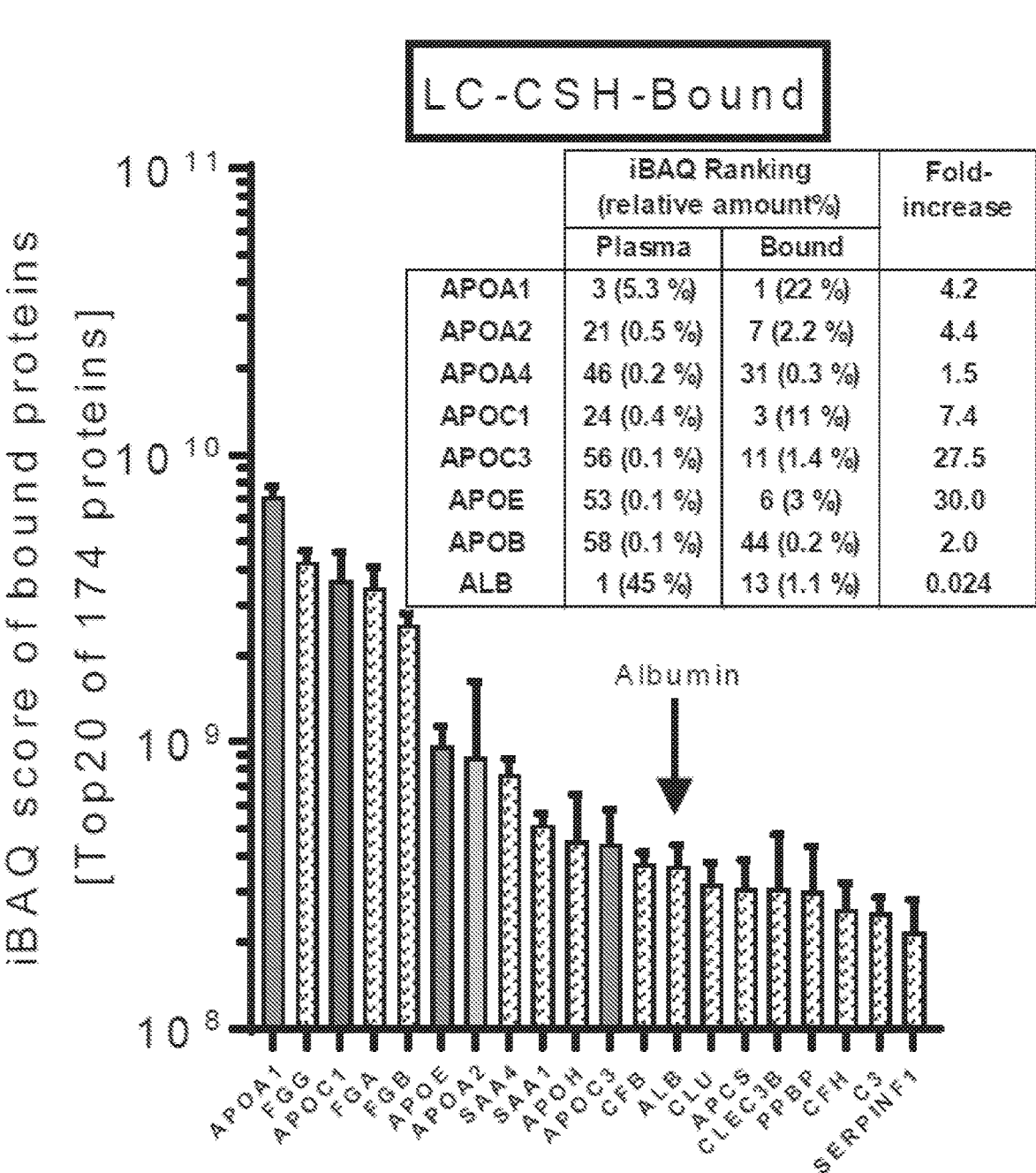
Figure 14E:
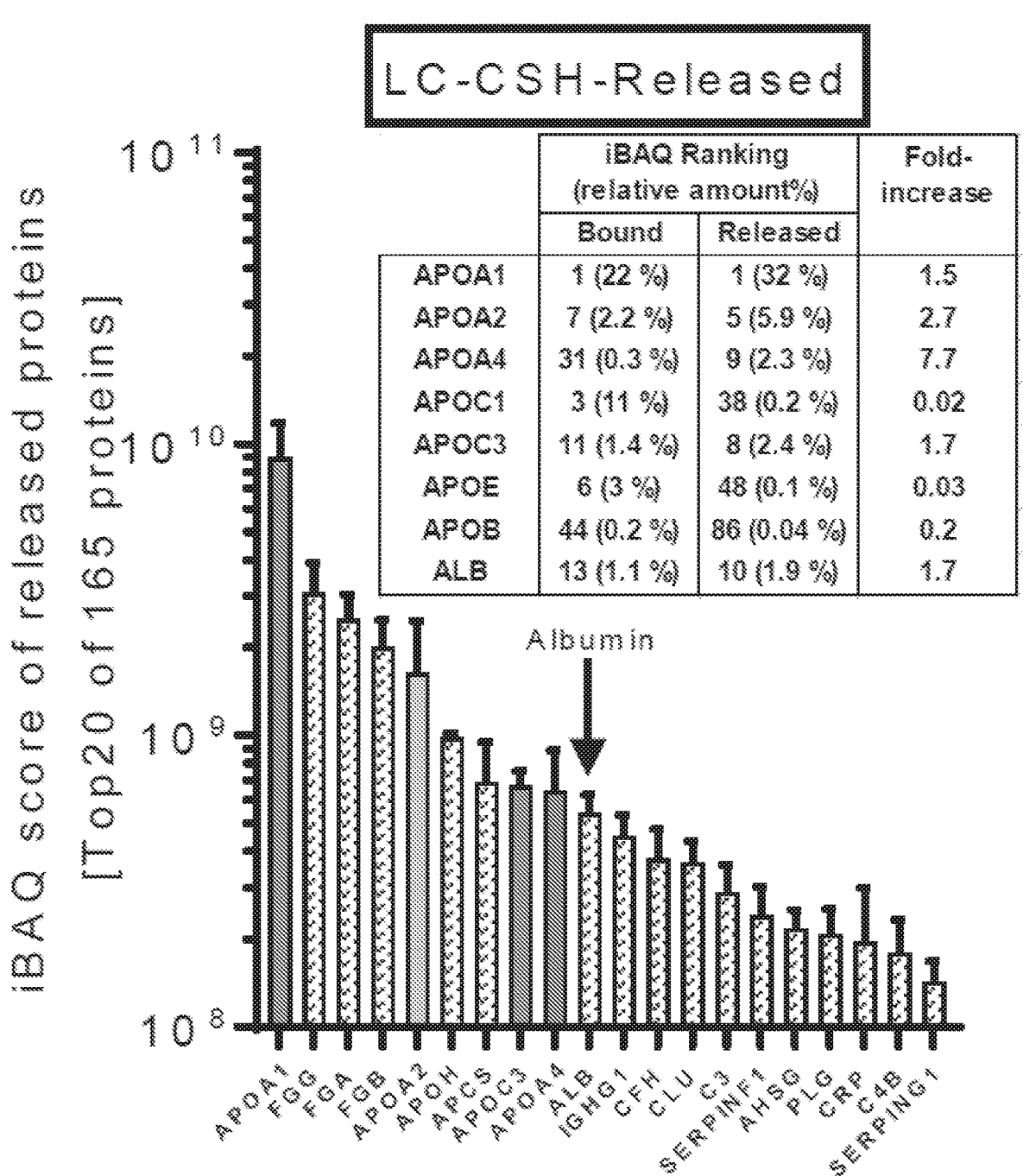

Exchangeable HDL apolipoproteins mediate HDL-SPE. Further characterization of the particles formed during HDL-SPE was performed and identified HDL-associated proteins that efflux *PE from LC-CSH. A 25 μL plasma sample was chosen in the following experiments, because it provided a sub-maximal, yet robust, fluorescent PE signal. As shown in FIG. 14A, the amount of plasma-mediated *PE efflux from LC-CSH increased over time but was linear for only the first 45 min. LC-CSH first pre-incubated with human plasma (but not saline) later effluxed *PE to saline after 1 hr at 37° C. (FIG. 14B). These findings are consistent with a model whereby plasma proteins that had initially bound to LC-CSH were then later released and removed *PE, during this process. Following a 30 min pre-incubation with human plasma, which is sufficient time to saturate LC-CSH binding sites (FIG. 14B), agarose gel electrophoresis revealed that *PE released from LC-CSH was associated only with HDL and contained very little neutral core lipid (triglycerides and cholesteryl esters) as indicated by the weak Sudan Black staining. Moreover, native gel lipoprotein electrophoresis demonstrated that mostly small *PE-tagged-HDL-like particles (<9.7 nm) were released from LC-CSH. The particle size distribution was similar in both the supernatant and the released pools. Notably, there was a concomitant loss of the larger-sized HDL in both the supernatant and the released pools compared to the original plasma. These findings are readily explained if apoA-I, and potentially other HDL-associated exchangeable apolipoproteins that are known to be continuously released from HDL, bind to LC-CSH, solubilize LC-CSH lipids, and are then subsequently released from LC-CSH as small *PE-labeled lipidated apolipoproteins. Proteomic analysis indeed confirmed that exchangeable HDL-associated proteins, primarily apoA-I, but also, apoA-II, and apoC-III, and apoA-IV all bound to, and then were released from LC-CSH (FIGS. 14C-14E). Notably, apoA-IV was one of the most highly enriched in the LC-CSH-released pool consistent with previous reports that plasma apoA-IV is easily displaced from HDL, enhances C-CEC, and moreover, is inversely associated with CAD. In contrast, apoE, which is one of the larger-sized exchangeable proteins and more firmly binds lipoproteins, was enriched in the proteins bound to LC-CSH but was not detected among the proteins that were later released from LC-CSH. Albumin, the most abundant plasma protein, was nearly 20-fold less abundant than apoA-I in both the bound and released proteins, demonstrating the specificity of binding and release of HDL-associated proteins to LC-CSH. Very little plasma apoB bound to LC-SCH and almost none was found in the released fraction consistent with the lack of *PE labeling of LDL observed by agarose gel analyses and the relative non-exchangeability of this protein. ApoA-I and other exchangeable apolipoproteins must first dissociate from HDL, bind to the surface of LC-CSH particles and are then later released into the supernatant together with LC-CSH-derived lipids, including *PE and *Chol in the form of small, lipidated apolipoprotein particles.

Figure 15A:
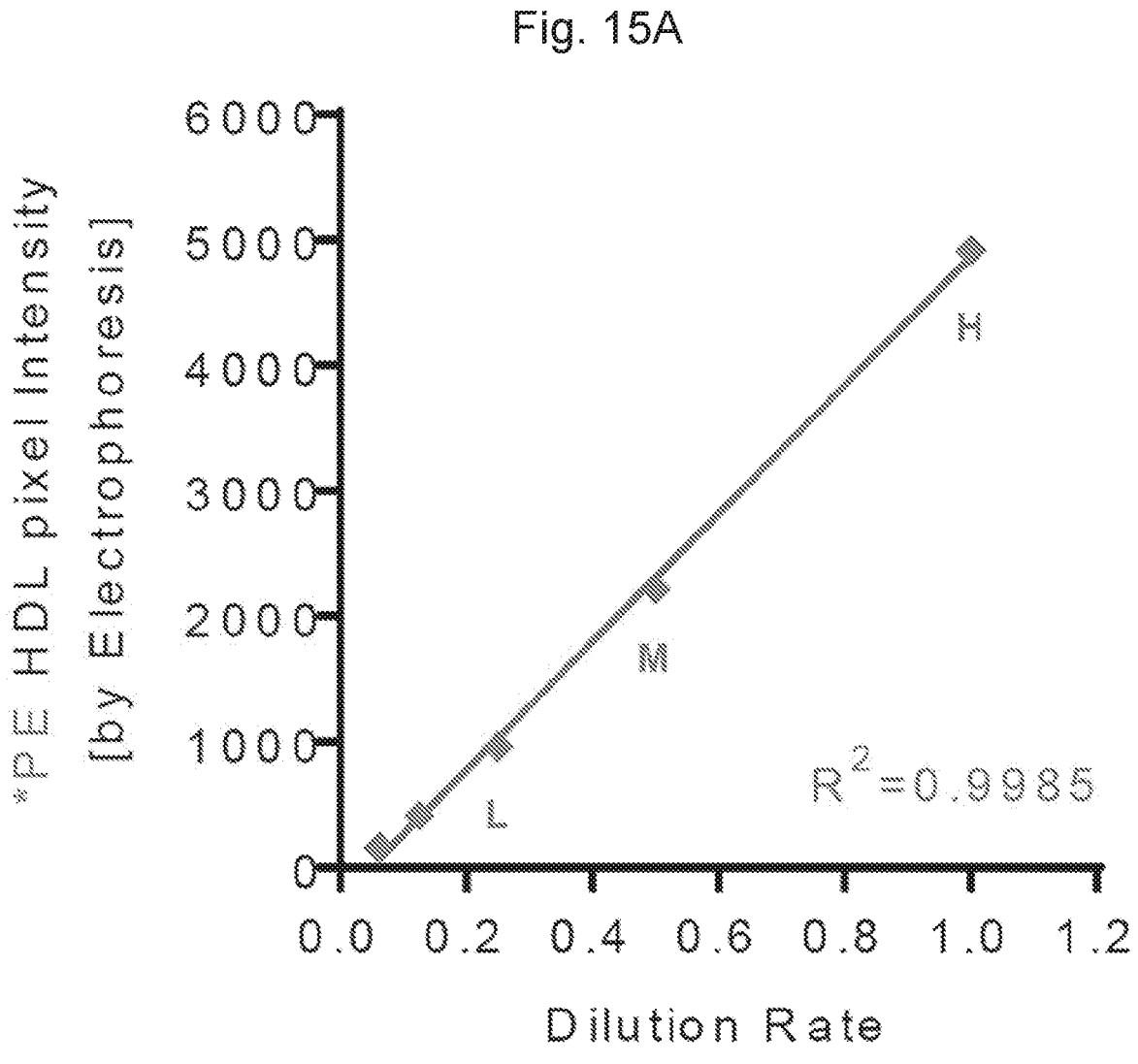
FIG. 15A presents a graph showing an isolated *PE-labeled HDL standard curve used to normalize HDL pixel intensity between gels.
Figure 15B:
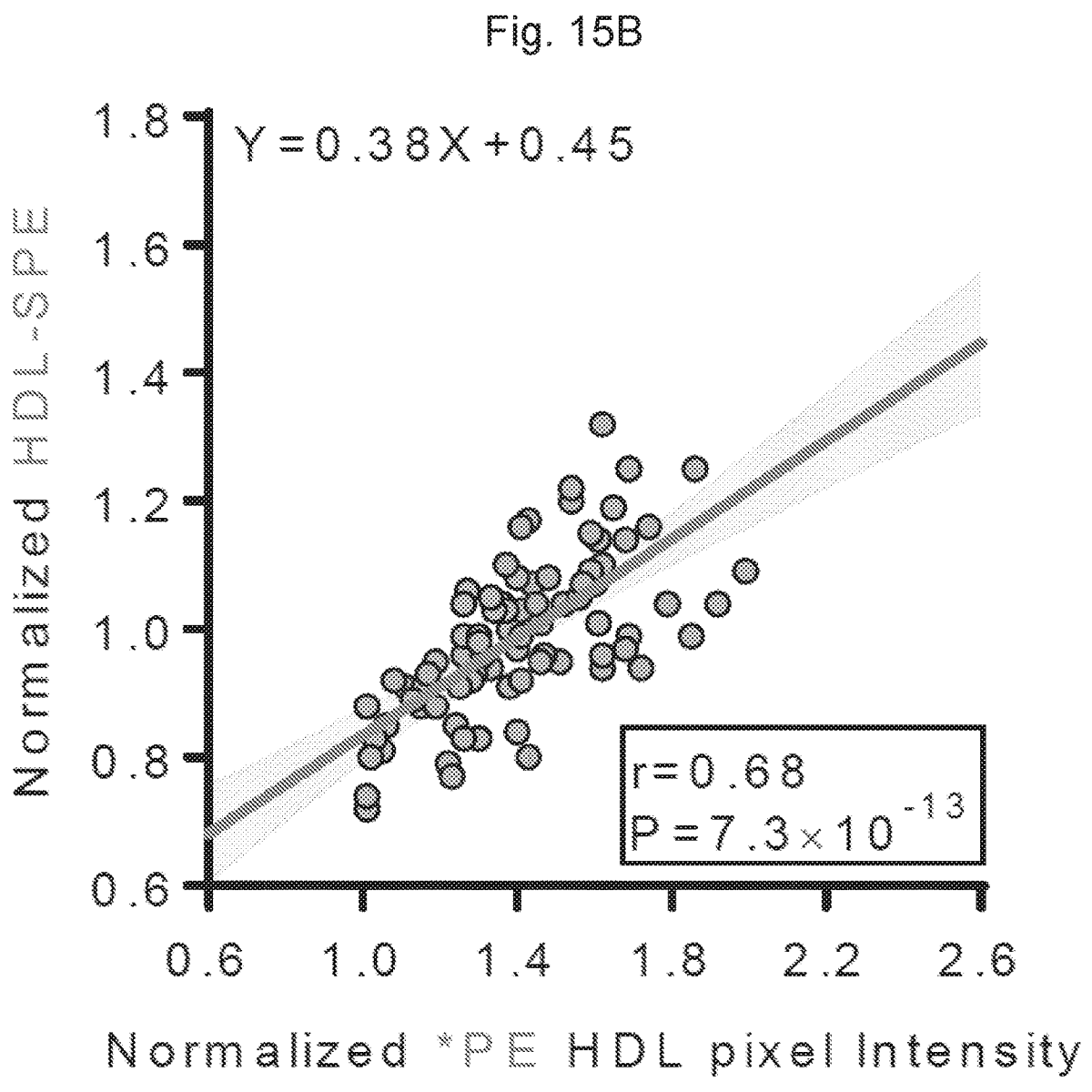

Association of HDL-SPE with CAD by CCTA. The association of the HDL-SPE and C-CEC assays to CAD a cohort of 84 known cardiovascular disease (CVD) subjects that had undergone coronary computed tomography angiography (CCTA) (Clinical Study I) was examined. This cohort was 43% male with a mean age of 60.4 years and was generally normolipidemic. Agarose gel electrophoresis demonstrated that LC-CSH *PE specifically incorporated into serum HDL in all 84 subjects consistent with the specificity of *PE incorporation into plasma HDL. Consistent with the studies using pooled human plasma (FIG. 12B), HDL-SPE also highly (r=0.68) and significantly (p=7.3×10$^{-13}$) correlated with HDL *PE gel pixel intensity (FIGS. 15A and 15B). Thus, the specificity of LC-CSH *PE efflux to HDL in both human serum and plasma was validated.

Figure 16A:
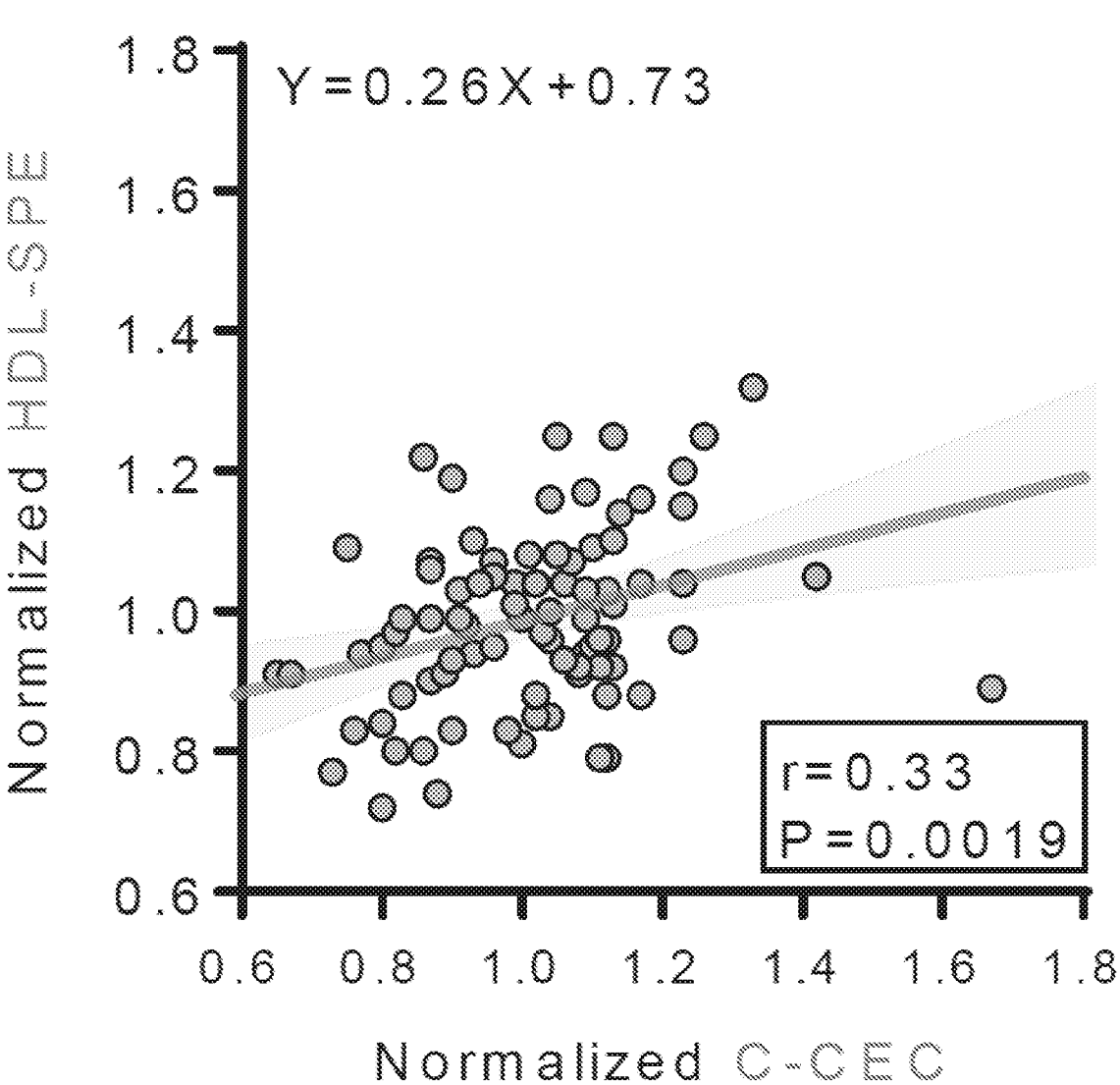
FIG. 16A is a graph showing correlation between HDL-SPE and C-CEC assays in cohort of 84 CVD subjects.
Figure 16B:
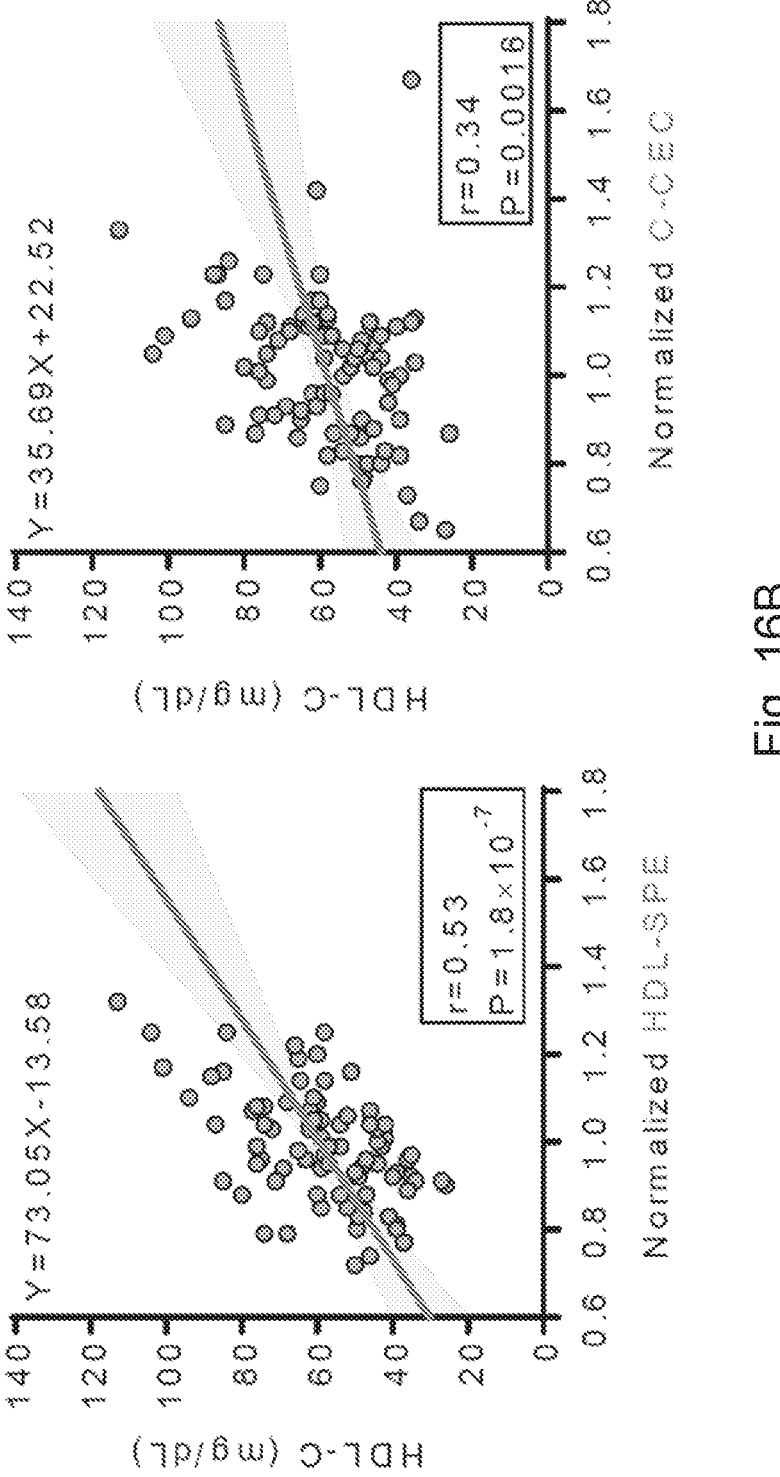
FIGS. 16B-16D present graphs showing bivariate correlation of HDL-C (16B), HDL particle number (HDL-P) (16C), and apoA-I (16D) with HDL-SPE and C-CEC. HDL-SPE and C-CEC both correlate with plasma HDL-C, HDL-P and apoA-I.
Figure 16C:
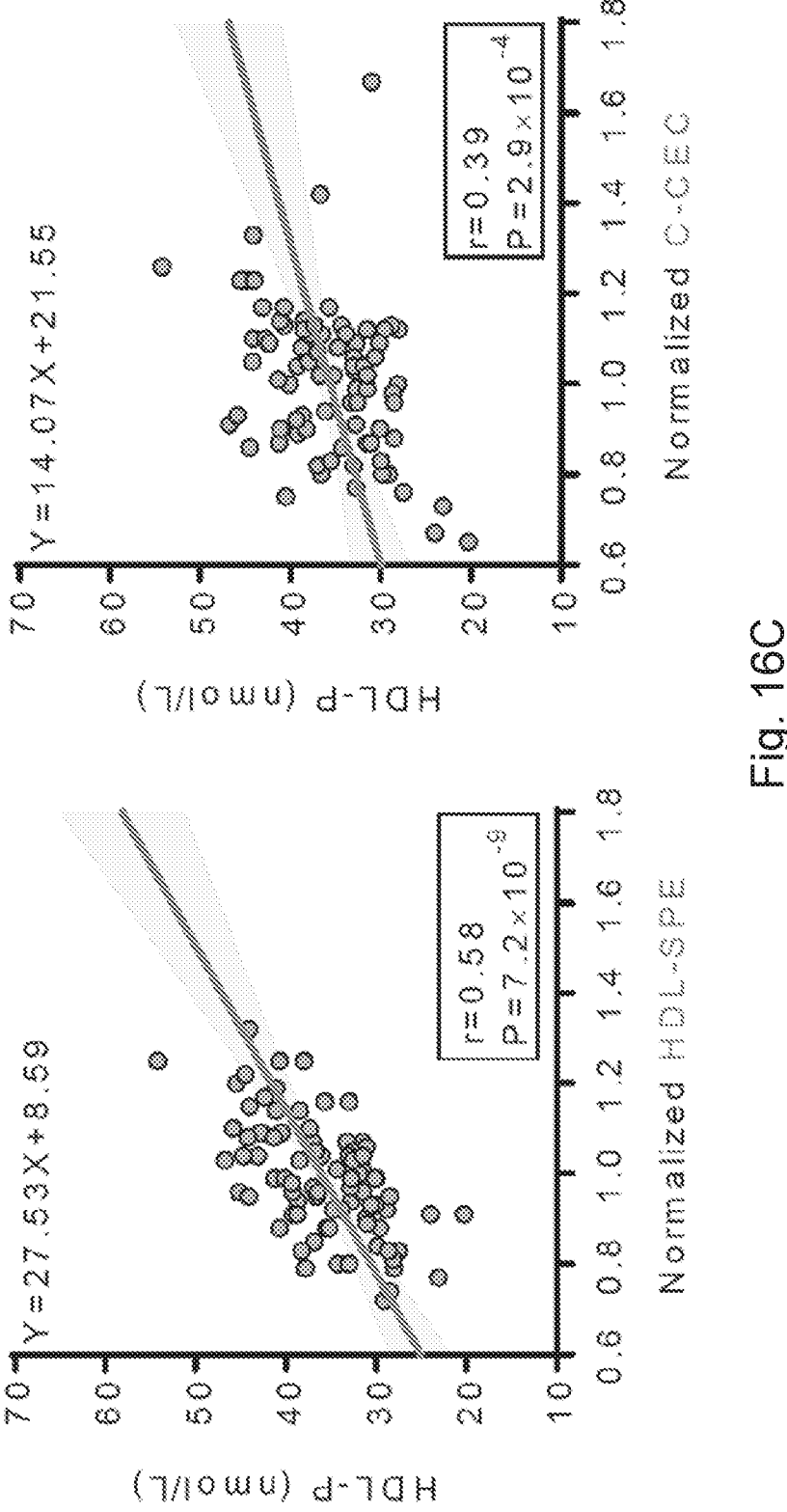
Figure 16D:
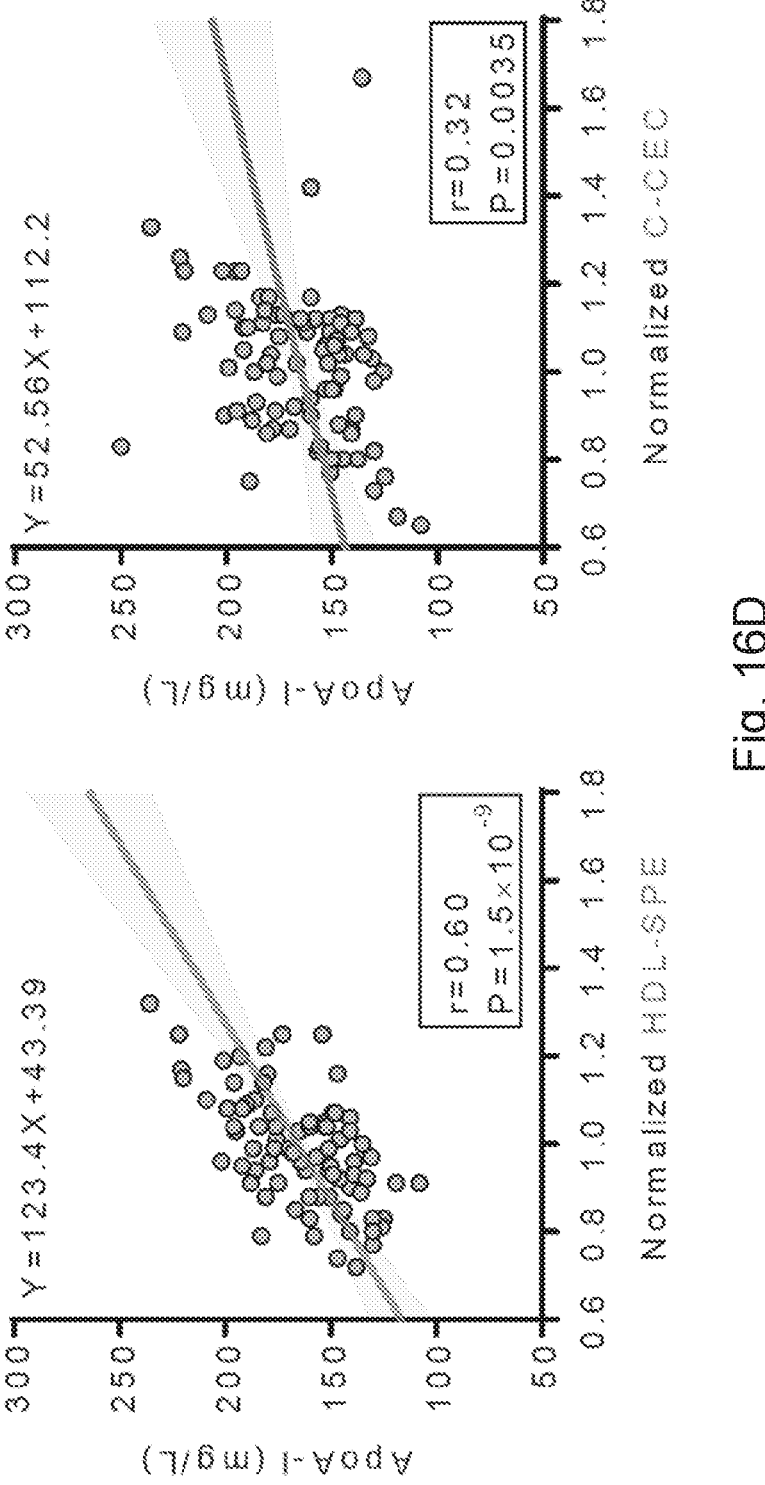

HDL-SPE and C-CEC (FIG. 16A) correlated only modestly (r=0.33) with each other, likely due to the different mechanisms underlying their respective efflux processes. Both HDL-SPE and C-CEC correlated, however, with HDL-C (FIG. 16B), HDL particle number (FIG. 16C), and apoA-I (FIG. 16D). Even after adjustment for age, gender, BMI and lipid lowering therapy, HDL-SPE maintained highly significant correlations with HDL-C, HDL-P, and apoA-I. In contrast, these parameters only modestly correlated with C-CEC (FIGS. 16B-16D). The more modest correlations that were observed between C-CEC and these HDL parameters are remarkably similar to those reported for a nested case (CVD)-control study in the JUPITER trial.

Figure 16E:
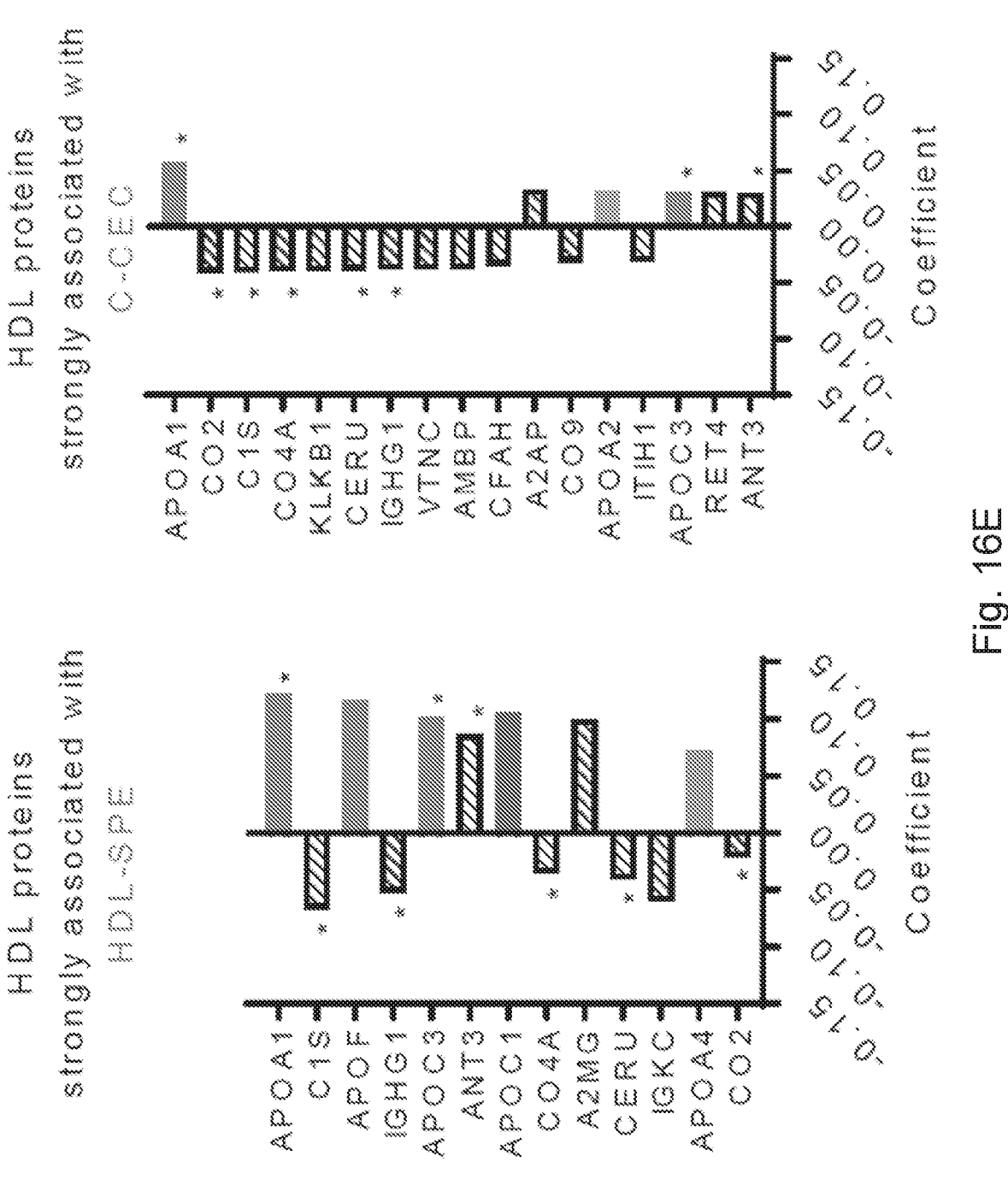
FIG. 16E presents graphs showing proteomic assessment of HDL proteins associated with HDL-SPE and C-CEC in 84 subjects in Clinical Study I. Asterisks denote identical proteins in HDL-SPE and C-CEC.
Figure 16F:
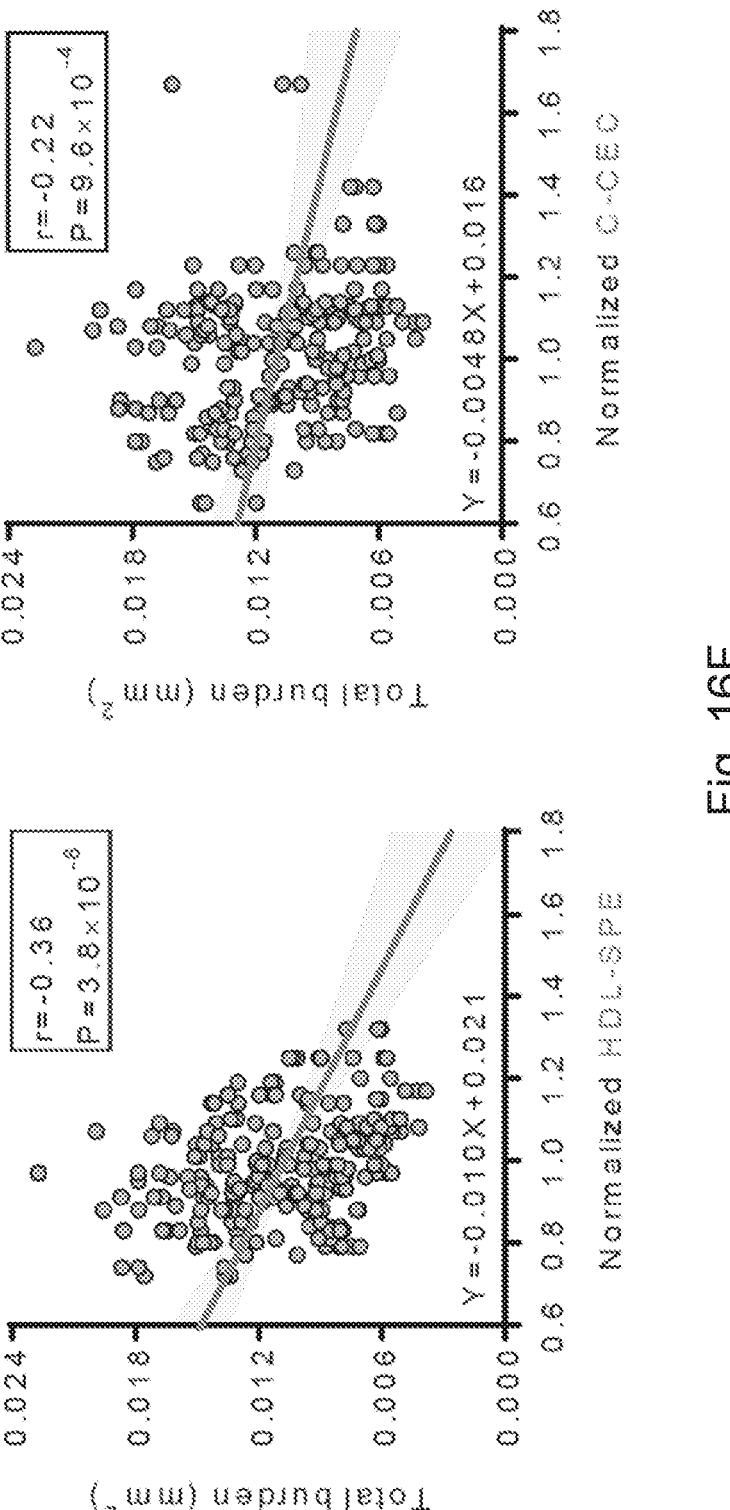
FIGS. 16F-16H present graphs showing association of HDL-SPE and C-CEC with (16F) TB, (16G) NCB, and (16H) DCB. HDL-SPE and C-CEC both inversely correlate with TCB and NCB, but not DCB.
Figure 16G:
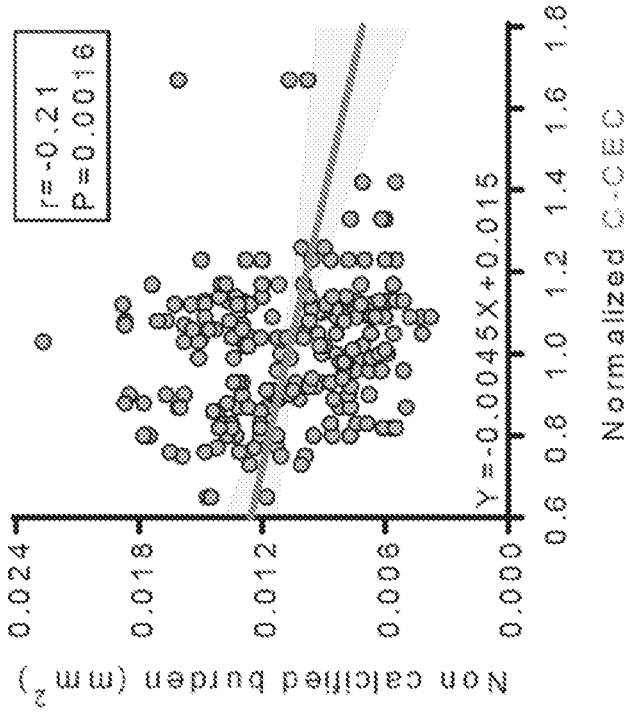
Figure 16G:
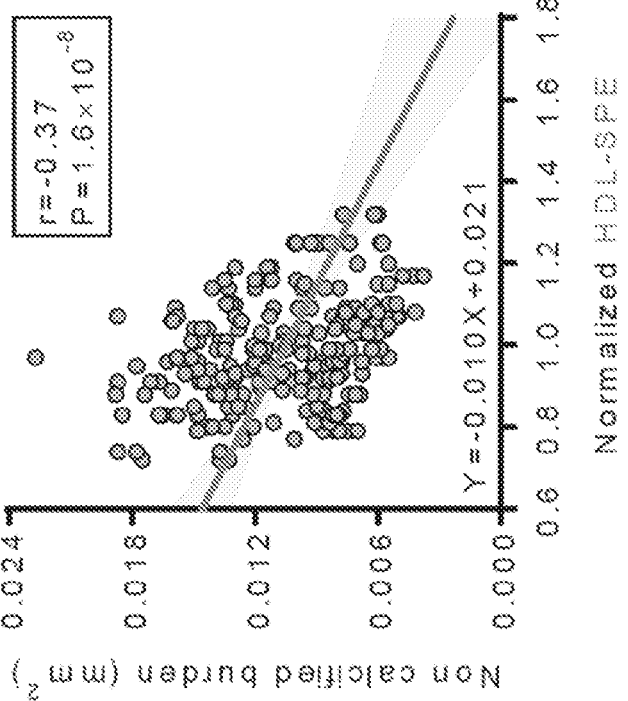

HDL proteomic analyses of the 84 subjects in Clinical Study I revealed that apoA-I was most strongly associated with both HDL-SPE and C-CEC (FIG. 16E); however, consistent with FIG. 16D, the strength of the correlation was about 2-fold greater with HDL-SPE compared to C-CEC. Moreover, consistent with the proteomic analysis of plasma proteins that mediate HDL-SPE, apoA-I, apoC-III, and apoA-IV were all strongly associated with HDL-SPE in the sera of the 84 subjects in Clinical Study I. These findings are also in accordance with the previous observation that these exchangeable apolipoproteins mediate phospholipid efflux from ABCA1-expressing cells in vitro.

Figure 16H:
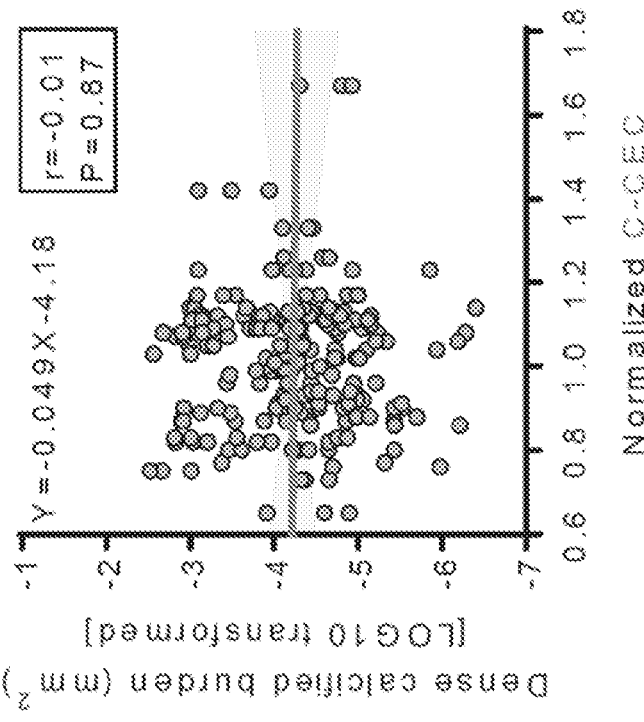
Figure 16H:
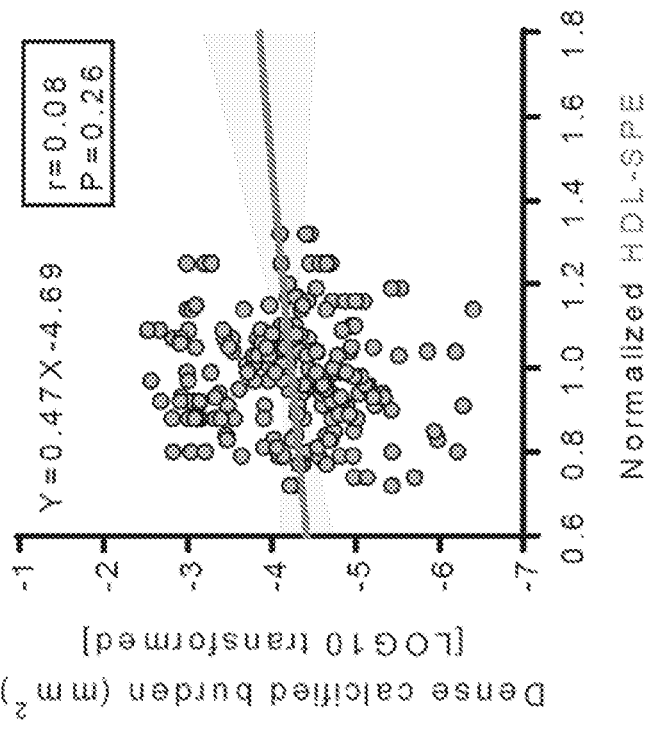
Figure 16I:
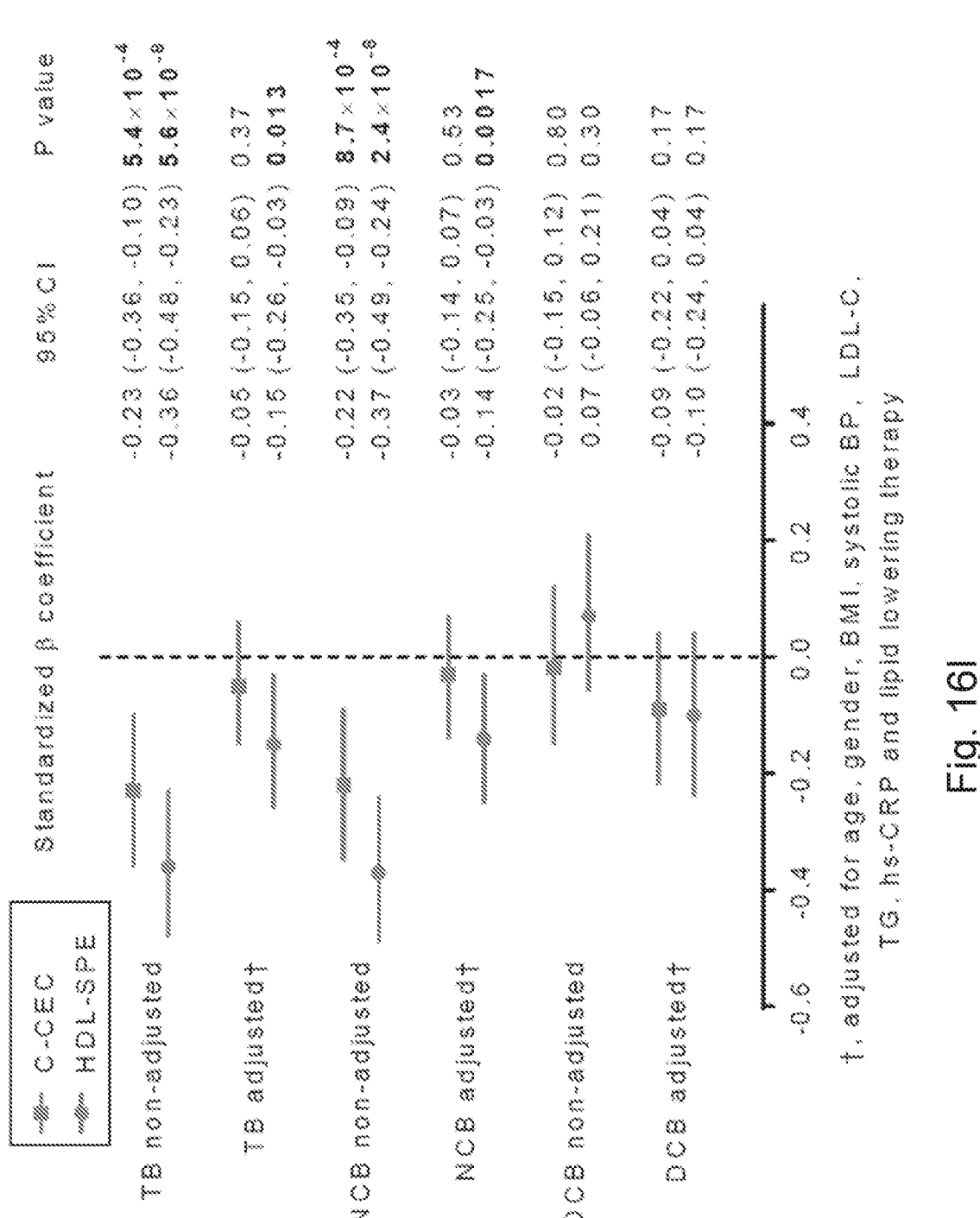
FIG. 16I is a graph showing bivariate and multivariate regression analysis of HDL-SPE and C-CEC association with TB, NCB and DCB. Only HDL-SPE remained significantly inversely correlated with TB and NCB after variable adjustment.

Next compared were the ability of the HDL-SPE and C-CEC assays to predict coronary artery plaque burden in this cohort (FIGS. 16F-16I). C-CEC has previously been shown to be inversely correlated with atherosclerotic non-calcified plaque burden in psoriasis patients. In coronary vessels non-calcified, dense calcified and total plaque burden (NCB, DCB, and TB, respectively) was measured. Bivariate analyses revealed that both HDL-SPE and C-CEC inversely correlate with total (FIG. 16F) and non-calcified plaque burden (FIG. 16G), but not DCB (FIG. 16H). The correlations between TB and NCB showed considerably greater statistical significance with HDL-SPE than C-CEC. Multivariate regression analysis revealed that after adjustment for age, gender, systolic BP, LDL-C, TG, high-sensitivity (hs)CRP and lipid-lowering therapy, HDL-SPE remained significantly inversely correlated with TB and NCB, whereas in this cohort, C-CEC did not. Bivariate analyses revealed that adjustment for BMI and HDL-C eliminated the association of C-CEC with TB and NCB. In contrast, the association of HDL-SPE with TB and NCB was independent of BMI and HDL-C. Since NCB reflects plaque lipid-burden, the inverse correlation of HDL-SPE with NCB may reflect the ability of apoA-I to remove arterial plaque lipids in vivo.

Figure 17A:
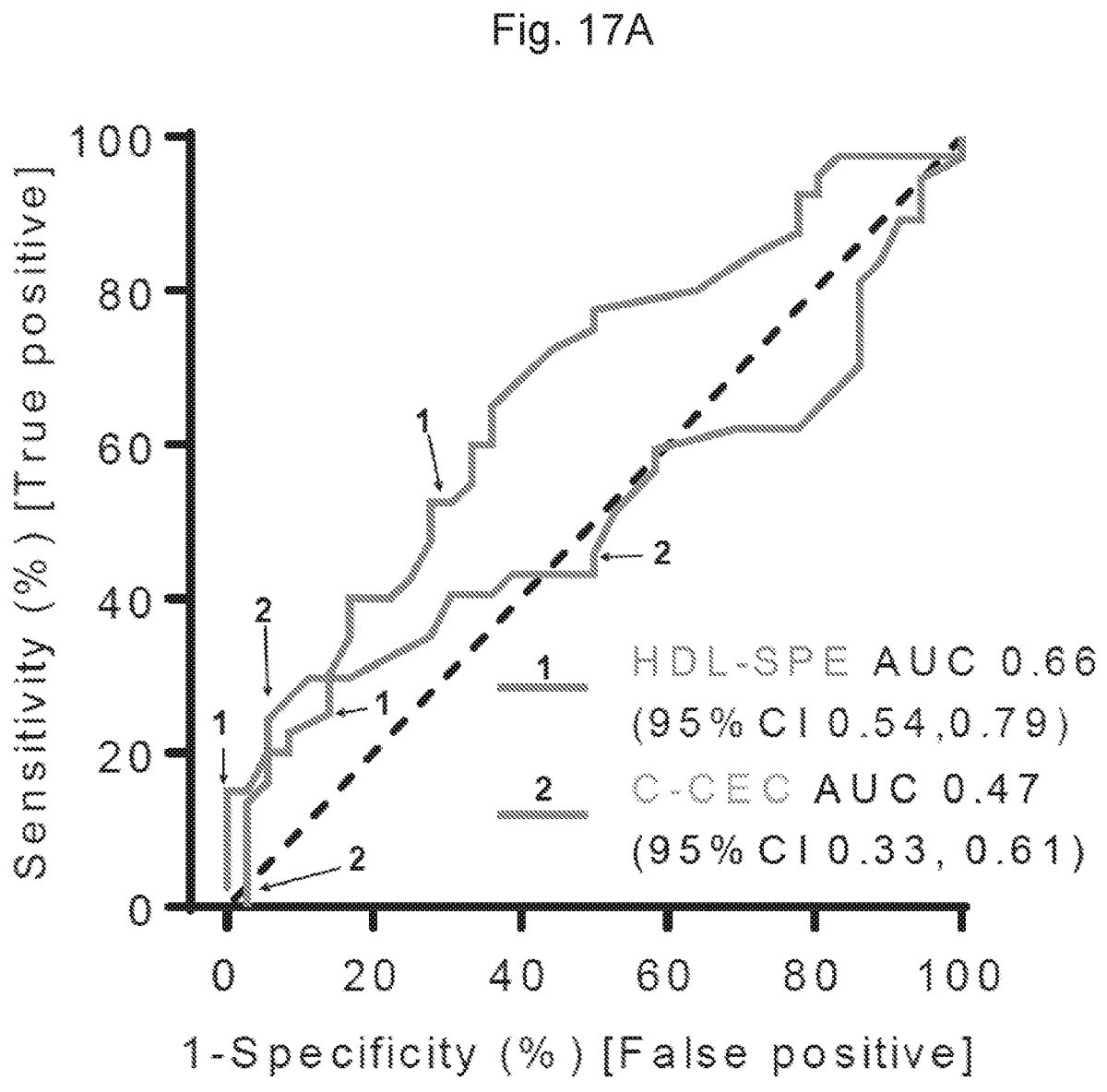
Figure 17B:
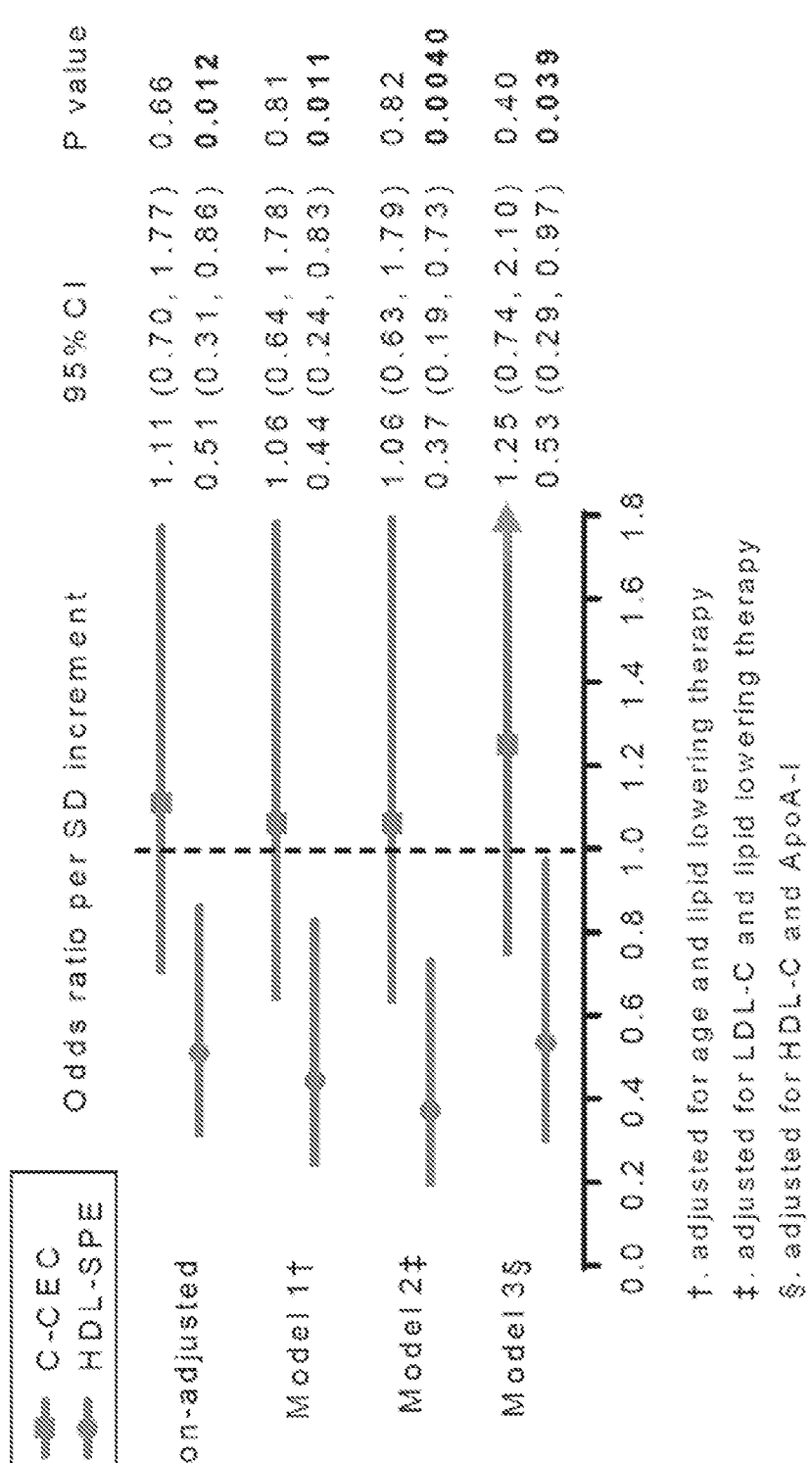
FIG. 17B is a graph showing odds ratios reported per SD increment for HDL-SPE and C-CEC based on univariate (non-adjusted) as well as conditional logistic multivariate regression analyses adjusted for risk factors and biomarkers as indicated.

HDL-SPE can detect dysfunctional HDL and predict severe CAD. An additional 76 severe CAD cases (n=40) and well-matched non-CAD subjects (n=36) were included in this study (Clinical Study II). Severe CAD was defined as CAD-RADS 5 (total coronary occlusion) and non-CAD was defined as CAD-RADS 0/1 (no significant stenosis/minimum stenosis). Non-CAD and CAD subjects were well-matched for gender, BMI, HDL clinical parameters (apoA-I, HDL-C, and HDL particle number and size), but not for age, lipid lowering therapy or LDL-C. HDL-SPE and CAD were significantly inversely associated (P=0.004) and ROC analysis demonstrated an optimum cut-point of 0.99 for HDL-SPE to be predictive of severe CAD compared to non-CAD, with an AUC of 0.66 and a sensitivity of 65% and specificity of 64% (FIG. 17A). Multivariate logistic regression analysis revealed that HDL-SPE, but not C-CEC, could predict CAD in this cohort, even after adjustment for age and lipid-lowering therapy, LDL-C and lipid-lowering therapy, or, HDL-C and apoA-I (FIG. 17B). HDL-SPE was also predictive of CAD after adjustment for HDL-C and apoA-I, suggesting the inverse association of HDL-SPE is independent of these parameters. This finding indicates that HDL-SPE can detect dysfunctional apoA-I/HDL.

Figure 18A:
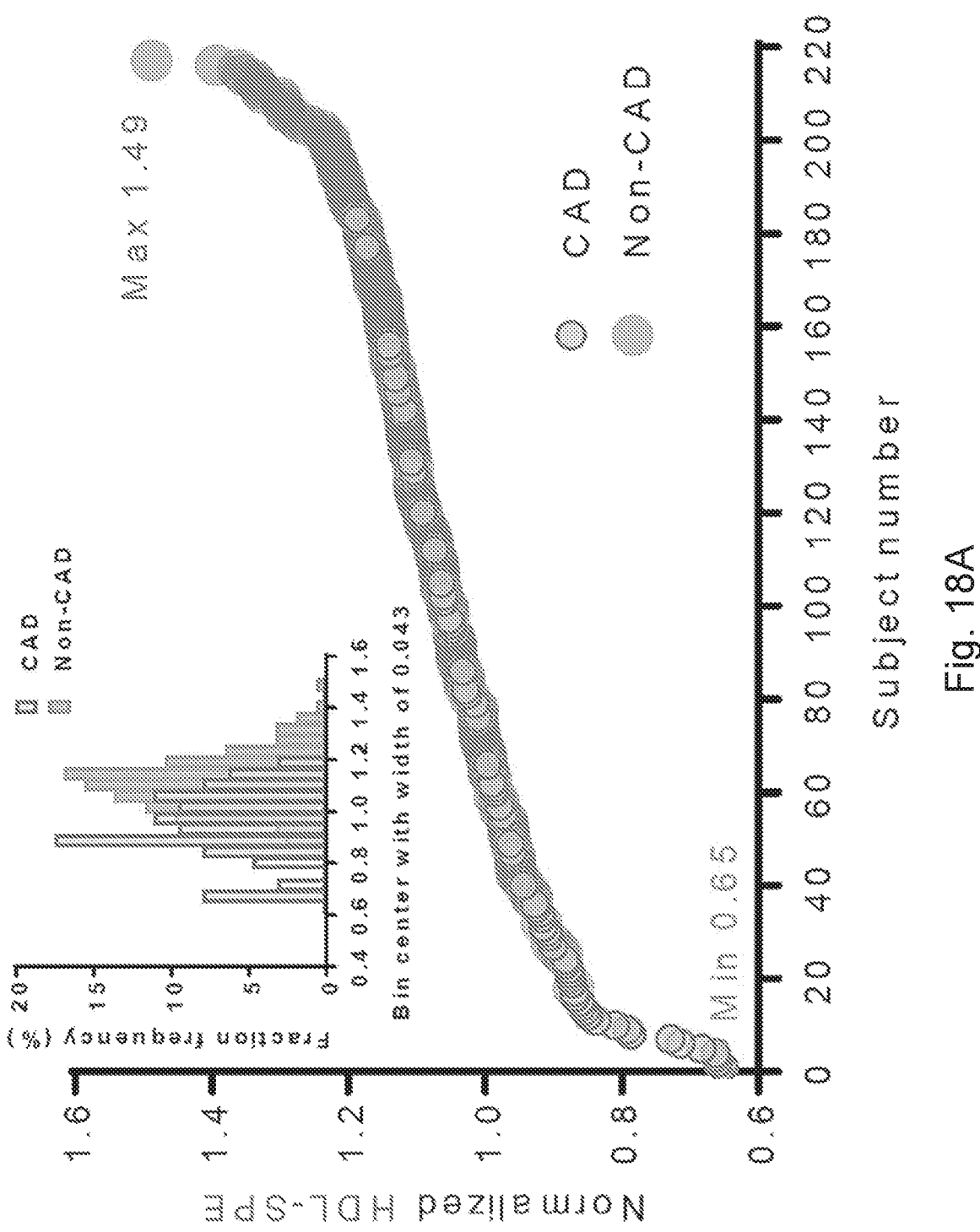
FIG. 18A is a graph showing ranked and frequency distribution (inset) of HDL-SPE values among CAD and non-CAD subjects.

HDL-SPE, but not HDL-C, can predict CAD in a Japanese cohort. A Japanese cohort (n=217) used in this study included both CAD (n=63) and non-CAD subjects (n=154) and CAD was evaluated based on standard coronary angiography (Clinical Study III). CAD and non-CAD subjects had significant differences in age, gender, hypertension, lipid lowering therapy, diabetes mellitus, and LCL-C. No significant difference in HDL-C was observed in the CAD vs non-CAD subjects. However, HDL-SPE was significantly reduced in CAD subjects. HDL-SPE values were normally distributed and ranged from 0.65-1.49 relative units (FIG. 18A). Interestingly, 23.8% of CAD/0% of non-CAD subjects had HDL-SPE<0.87, whereas 15.7% of non-CAD/0% of CAD subjects had HDL-SPE>1.19. The potential clinical applicability of the HDL-SPE assay is underscored by the observation that the efflux values did not drop off in the lower range or reach saturation at the highest values (FIG. 18A).

Figure 18B:
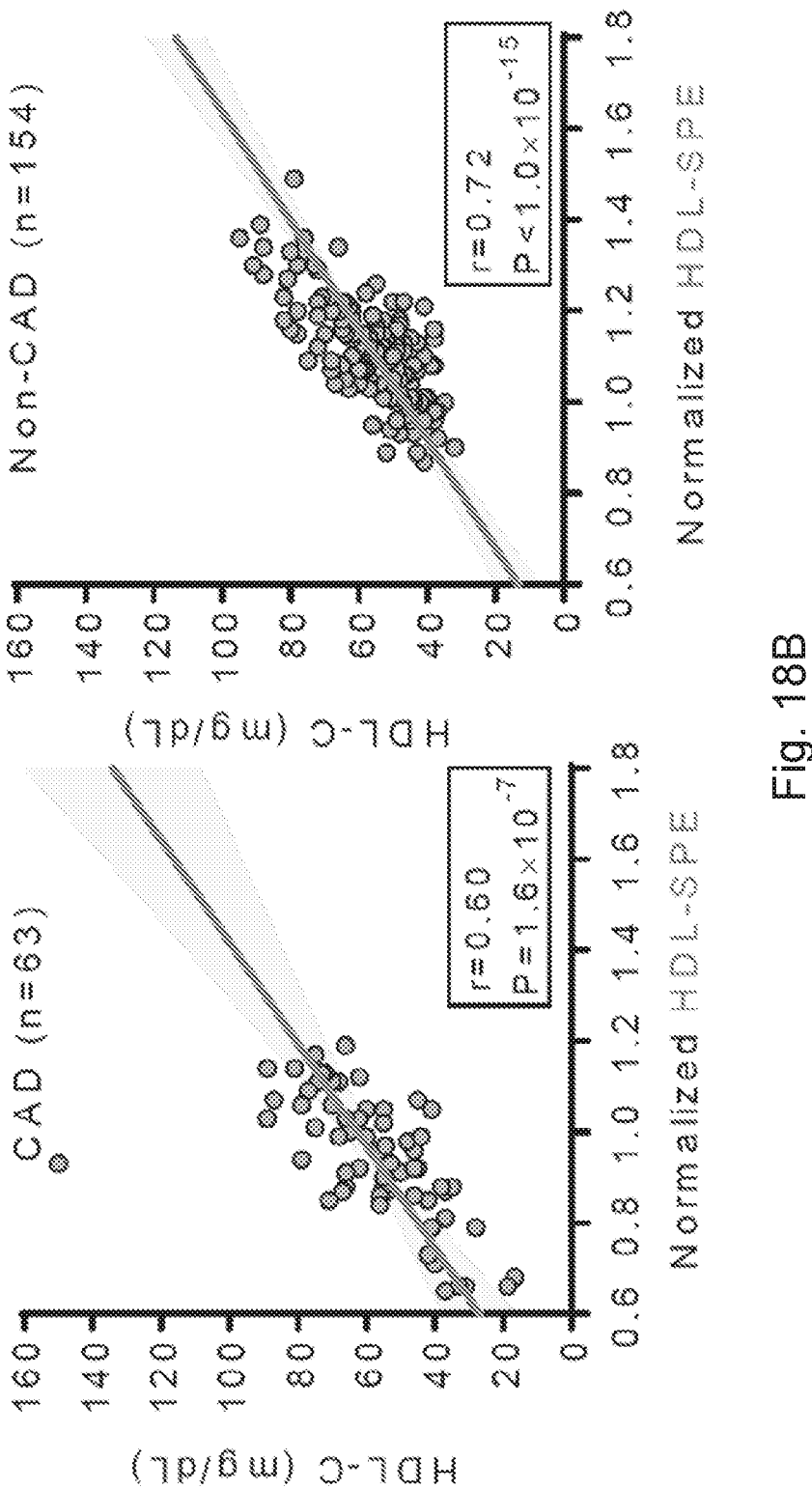
FIG. 18B presents graphs showing HDL-C significantly correlates with HDL-SPE.
Figure 18C:
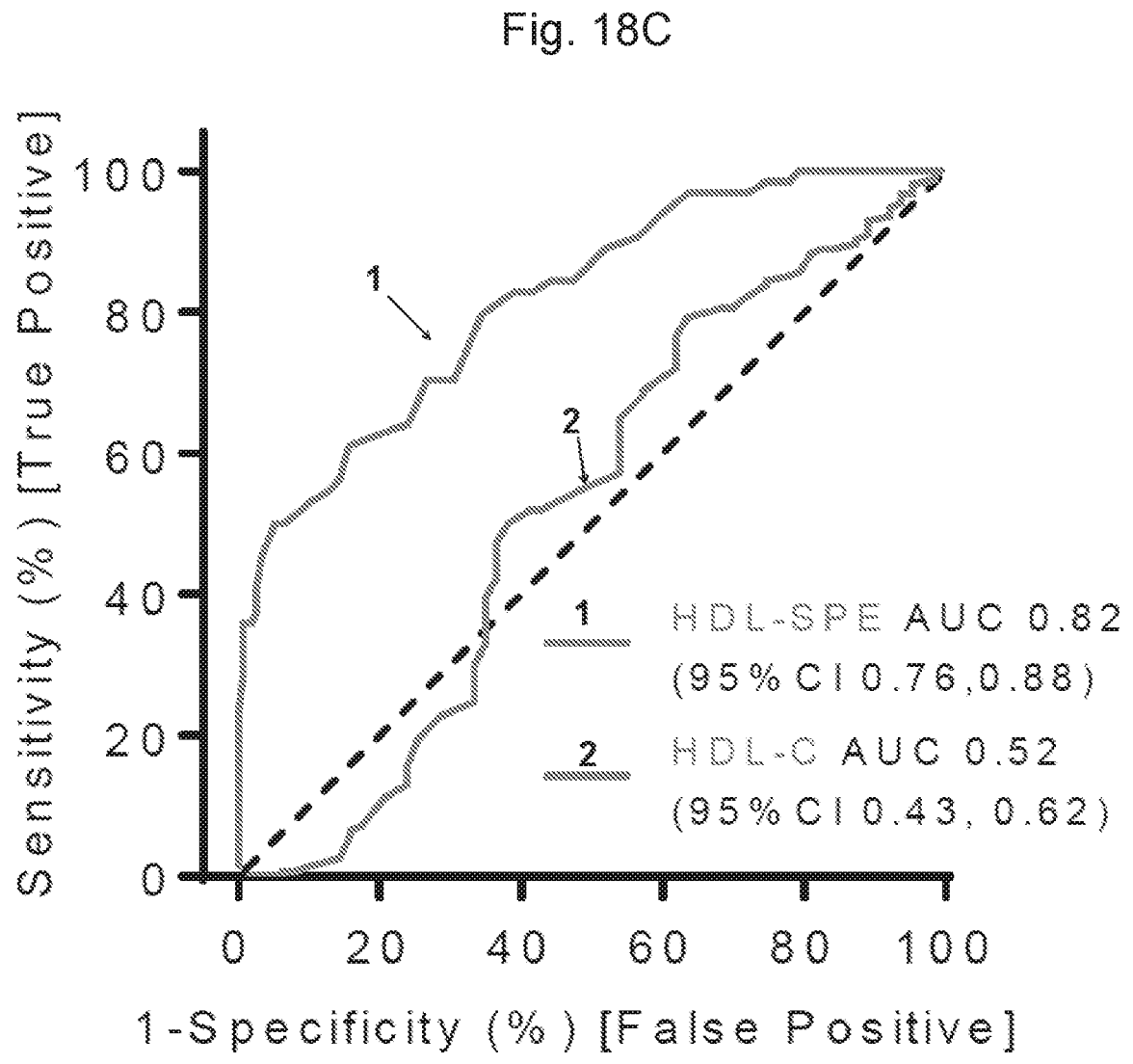
Figure 18D:
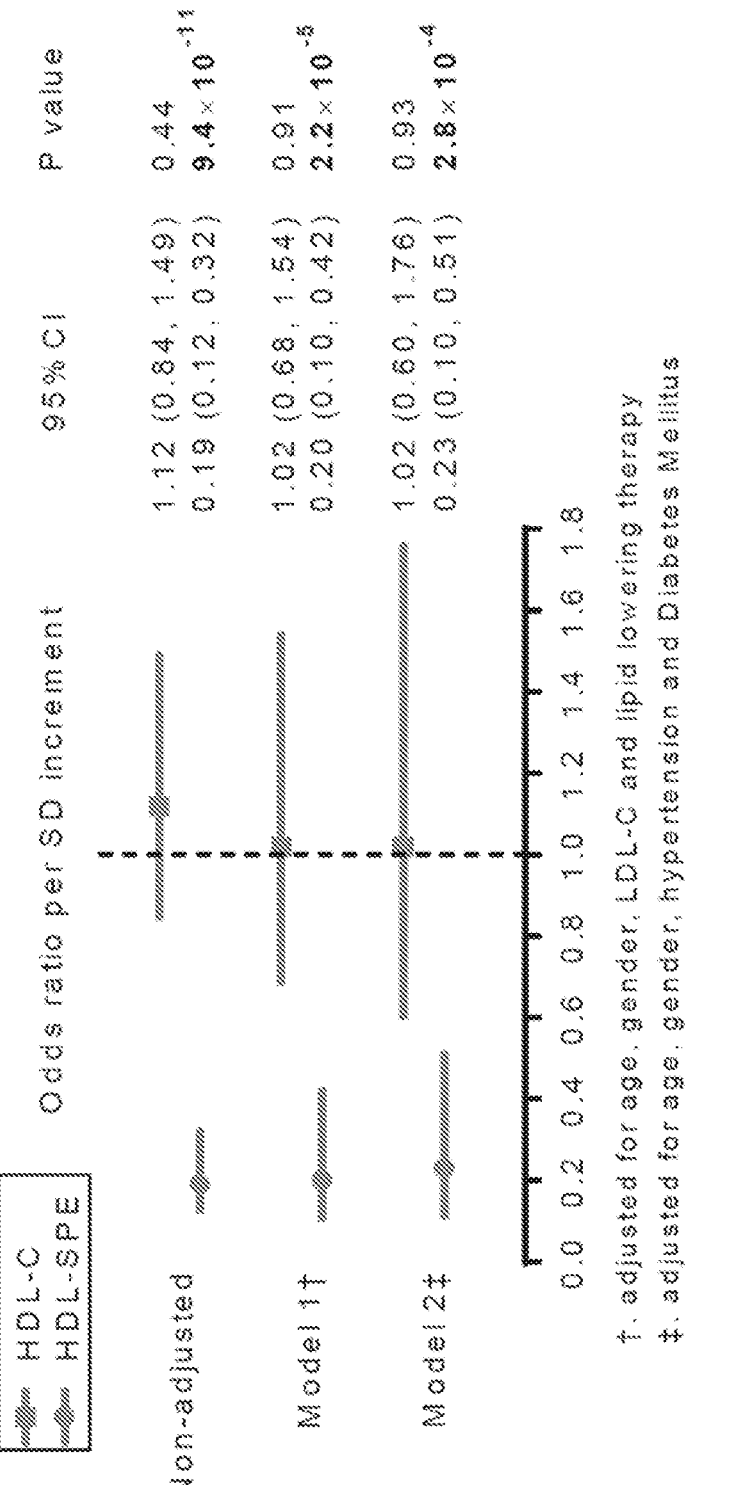
FIG. 18D is a graph showing odds ratios reported per SD increment for HDL-SPE and HDL-C based on univariate (non-adjusted) as well as conditional logistic multivariate regression analyses adjusted for risk factors and biomarkers as indicated.

HDL-C strongly correlated with HDL-SPE (FIG. 18B). However, HDL-SPE, but not HDL-C, was significantly inversely correlated with CAD in this cohort. ROC analysis demonstrated a cut-point of 1.03 for HDL-SPE to be predictive of severe CAD compared to non-CAD with an AUC of 0.82 and a sensitivity of 70.3% and specificity of 73.4% (FIG. 18C). The inverse association of HDL-SPE and CAD was only slightly reduced and remained highly statistically significant after adjustment for age, gender and LDL-C and, lipid lowering therapy (Model 1), or, hypertension and diabetes mellitus (Model 2) (FIG. 18D).

Figure 18E:
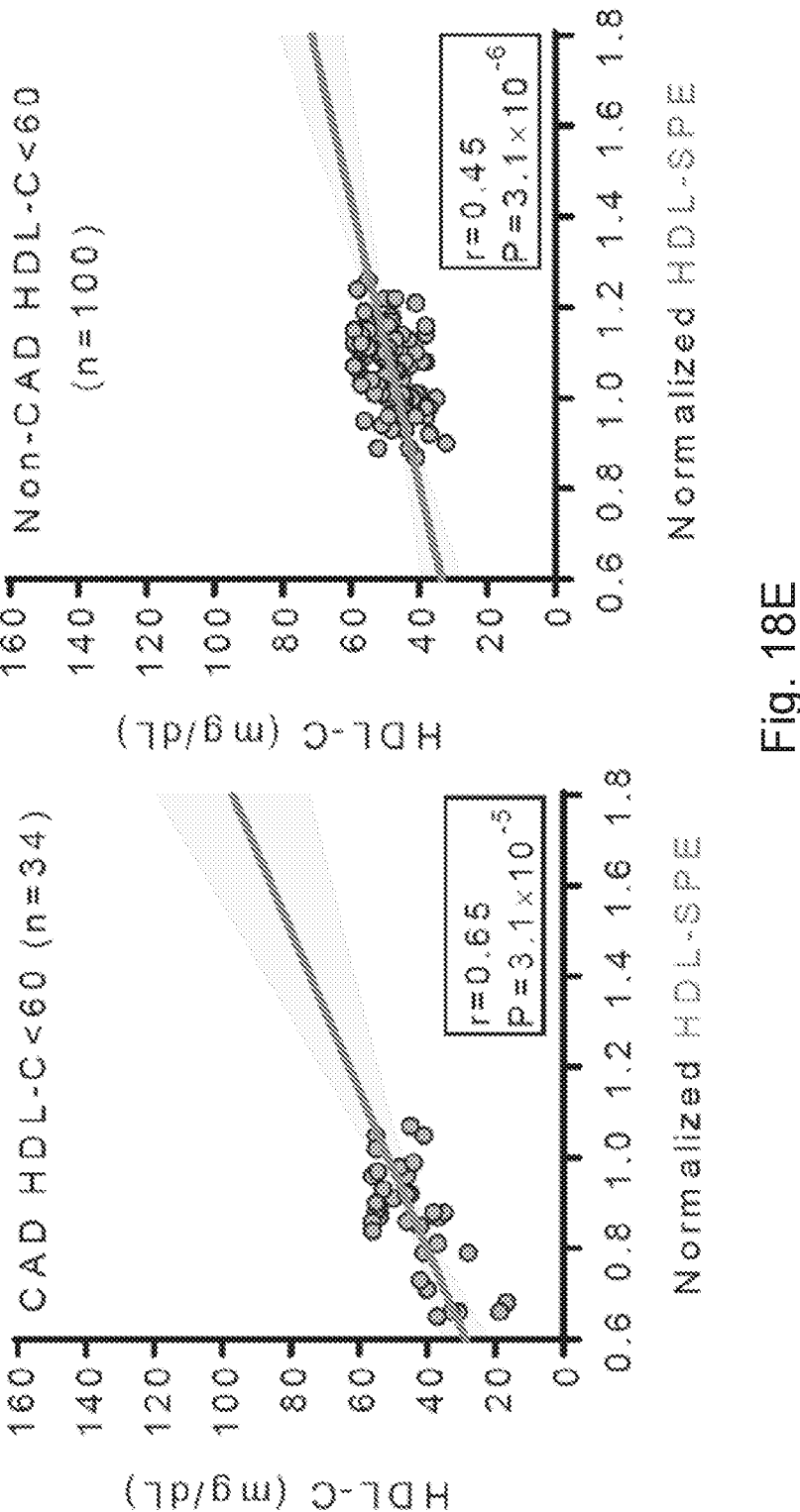
FIG. 18E presents graphs showing that both CAD and non-CAD HDL-C<60 mg/dL significantly correlates with HDL-SPE.
Figure 18F:
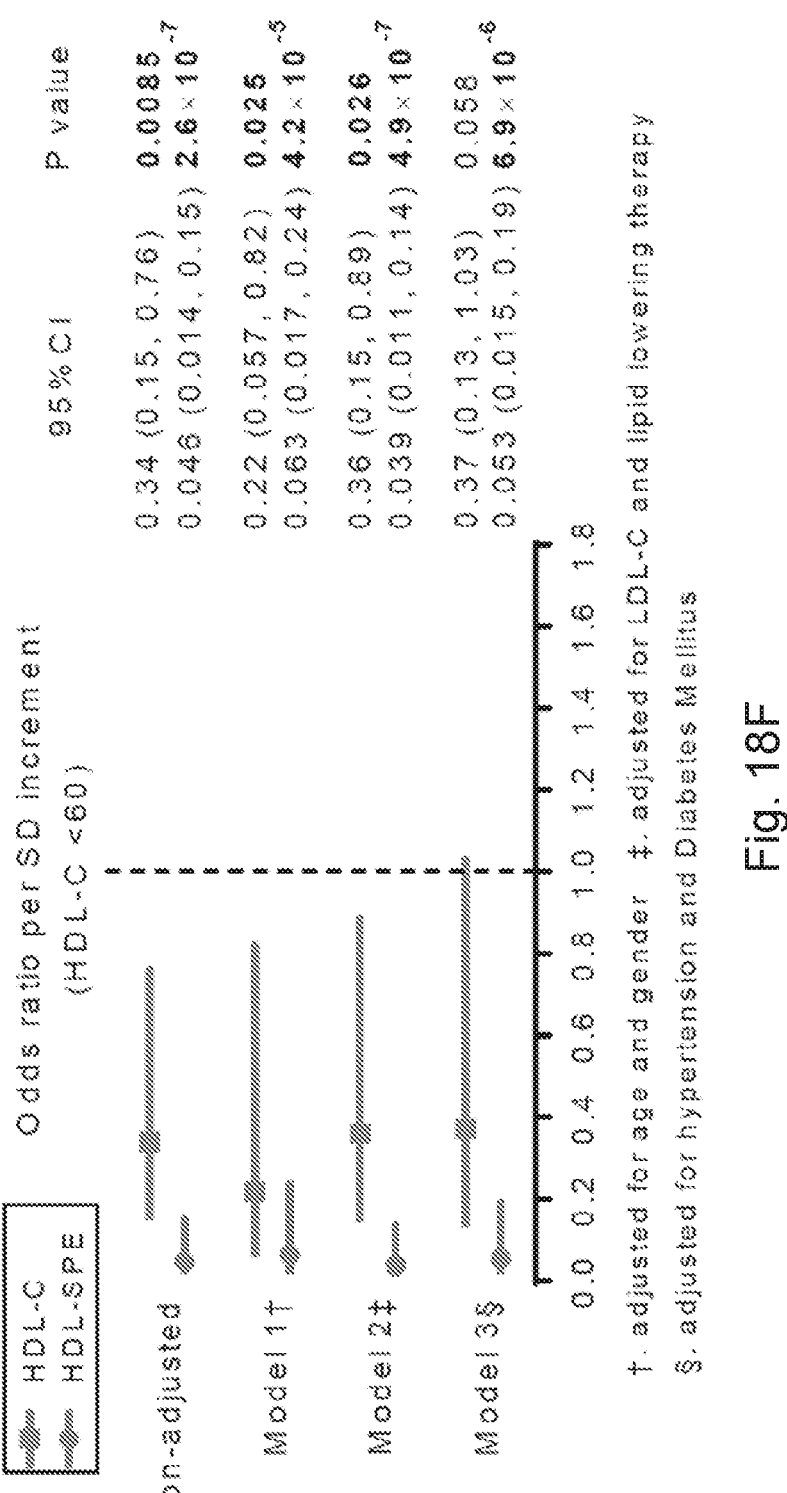
FIG. 18F is a graph showing odds ratios reported per SD increment for HDL-SPE and HDL-C<60 mg/dL based on univariate (non-adjusted) as well as conditional logistic multivariate regression analyses adjusted for risk factors and biomarkers as indicated.
Figure 18G:
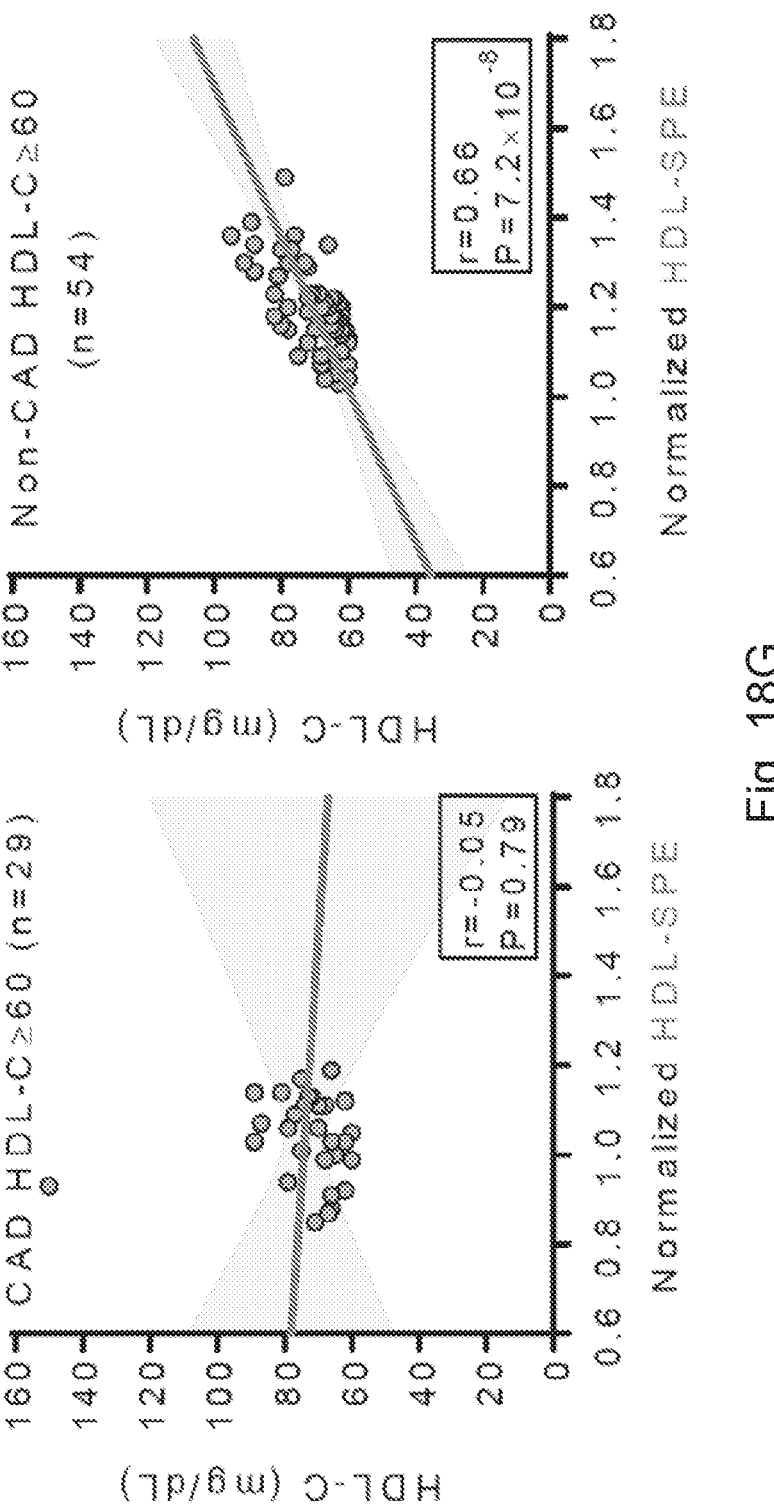
FIG. 18G presents graphs showing that non-CAD but not CAD HDL-C>60 mg/dL significantly correlates with HDL-SPE.

Next evaluated was the association of HDL-C in the CAD vs non-CAD subjects with HDL-SPE, by comparing subjects with HDL-C<60 mg/dL to those with HDL-C>60 mg/dL. This cut-off was chosen based on the previous observation in an Asian CAD cohort that HDL-C>60 mg/dL was associated with increased risk of CVD mortality, as well as a reduced C-CEC. In the Japanese cohort, HDL-C<60 mg/dL and HDL-SPE significantly correlated in both cases and controls (FIG. 18E). The inverse association of HDL-SPE with CAD was highly significant (FIG. 18F) even after adjustment for traditional risk factors. HDL-C was also inversely associated with CAD with borderline statistical significance in the HDL-C<60 mg/dL subjects (FIG. 18F). In contrast, although HDL-C>60 mg/dL and HDL-SPE correlated in the non-CAD subjects, there was no correlation at all between HDL-SPE and HDL-C in the CAD cases (FIG. 18G), even after adjustment for traditional risk factors and biomarkers.

Figure 18H:
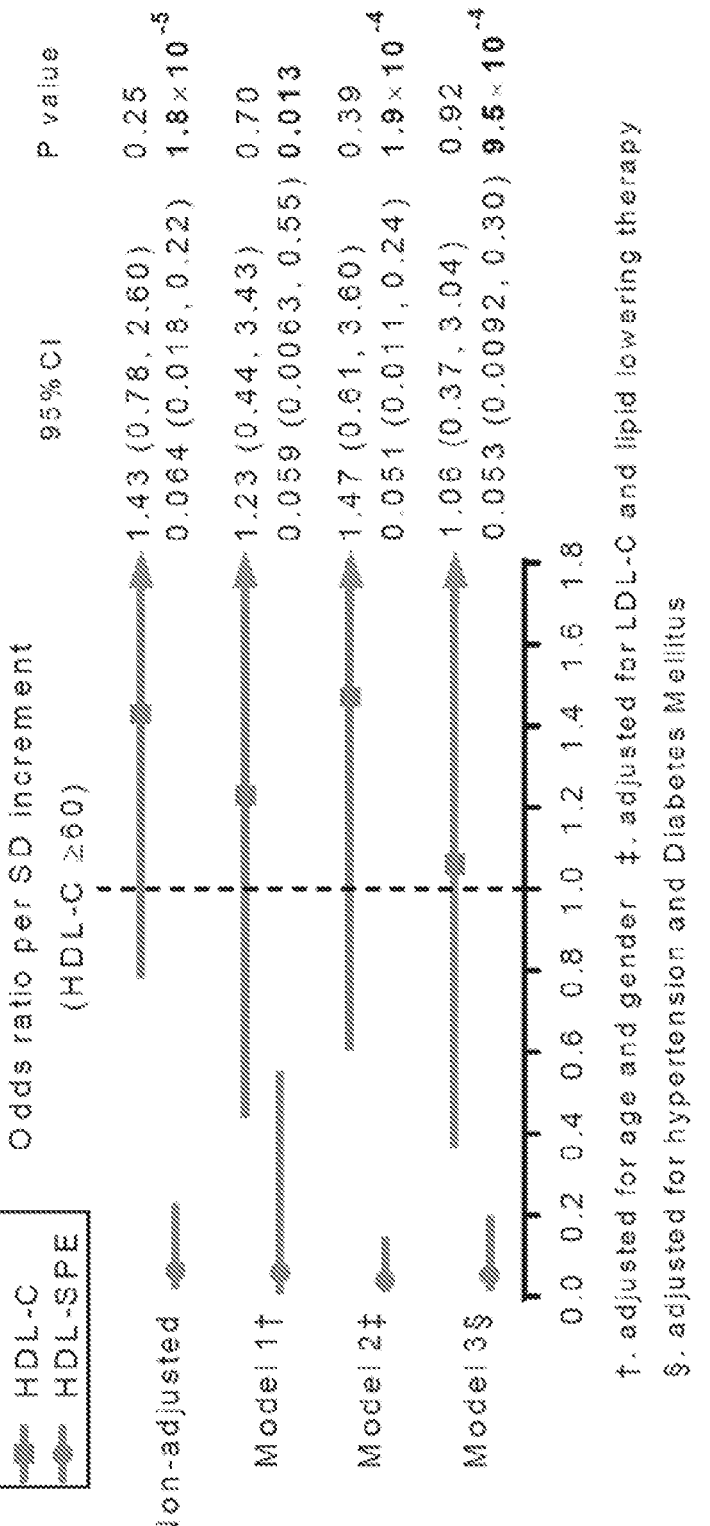
FIG. 18H is a graph showing odds ratios reported per SD increment for HDL-SPE and HDL-C<60 mg/dL based on bivariate (non-adjusted) as well as multivariate logistic regression analyses adjusted for risk factors and biomarkers as indicated.

The inverse association of HDL-SPE with CAD (FIG. 18H) was highly significant even after the same adjustments as in FIG. 18F. Remarkably, there was no association of HDL-C with CAD in the HDL-C>60 mg/dL subjects (FIG. 18H). Thus, HDL-SPE can predict CAD in cases with HDL-C>60 independent of HDL-C, which again is consistent with the ability of the HDL-SPE assay to detect dysfunctional HDL.

Discussion

HDL-C is currently used to assess CAD risk, but has limitations in that there is a complex parabolic relationship between HDL-C and cardiovascular events, and it is known to be inferior as a risk marker to functional based assays of HDL, such as C-CEC. Described herein is a cell-free HDL-specific phospholipid efflux assay (HDL-SPE) to assess CAD risk based on apoA-I/HDL functionality in whole plasma that can be readily automated. It was confirmed that HDL-SPE is indeed mediated by apo-AI and other exchangeable apolipoproteins (A-II, A-IV, C-III). The steps necessary for apoA-I and the other apolipoproteins to mediate HDL-SPE include their (i) dissociation from plasma HDL, (ii) binding to LC-CSH and, (iii) solubilization of LC-CSH lipids and subsequent release as *PE-labeled apolipoprotein particles. Apolipoprotein dissociation from HDL is a requisite permissive step in the HDL-SPE assay that has previously been shown to be associated with atherosclerosis and CAD. The *PE-apolipoprotein particles released from LC-CSH are likely similar to the types of pre-β-HDL particles generated in vivo from the interaction of apoA-I with ABCA1-generated cell membrane lipid domains. Cholesterol, and possibly phosphatidylethanolamine, may create packing defects in the donor particle lipid membrane surface that enable apolipoprotein binding and subsequent solubilization of donor particle lipids. In addition, the CSH crystals have regions of high curvature which may also facilitate generation of these potential packing defects.

The evaluation of the HDL-SPE assay in the three clinical cohorts indicates that it adds value in CAD prediction over not only the C-CEC assay but also more conventional measures of HDL, such as apoA-I, HDL-C, and HDL particle number and size. In the Clinical Study I, apoA-I plasma concentration, HDL-C and HDL particle number correlated more highly and significantly with HDL-SPE than with C-CEC. Conversely, no LDL-associated clinical parameters correlated with HDL-SPE. In addition, in Clinical Study II, HDL-SPE was a strong inverse predictor of CAD independent of apoA-I plasma concentration, HDL-C and HDL particle number. HDL-SPE, but not HDL-C, predicted CAD in a Japanese cohort. Taken together, these findings strongly suggest that the inverse association of HDL-SPE with CAD risk is based on its ability to detect HDL functionality. HDL-SPE, but not C-CEC was significantly inversely proportional to total plaque burden and non-calcified plaque burden (NCB), even after adjustment for traditional risk factors. The C-CEC assay has been shown to be superior to HDL-C in predicting incident CVD events, and similarly, the HDL-SPE may also be useful for this purpose but unlike the C-CEC assay, it can be developed into a routine test.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of assessing the risk for development of a disease in a patient, the method comprising:
    (i) incubating a sample of body fluid from the patient with donor particles, wherein the sample of body fluid is whole plasma, urine, or saliva, and wherein the donor particles are coated with a lipid and a first quantity of a detectably labeled, non-exchangeable lipid probe (NELP), which NELP is phosphatidylethanolamine (PE), prior to incubating the donor particles with the sample,
    wherein the detectably labeled NELP is effluxed by HDL,
    wherein the sample of body fluid comprises high density lipoprotein (HDL) and one or more HDL-associated protein(s) comprising apolipoprotein A-I (apoA-I),
    wherein the apoA-I specifically transfers at least a portion of the detectably labeled NELP from the donor particles to the HDL to produce detectably labeled NELP-associated HDL having a second quantity of detectably labeled NELP;
    (ii) separating the detectably labeled NELP-associated HDL into a first portion and the donor particles into a second portion;
    (iii) measuring the second quantity of detectably labeled NELP in the first portion;
    (iv) determining a detectably labeled NELP efflux value for the patient, wherein the detectably labeled NELP efflux value for the patient equals the second quantity of detectably labeled NELP divided by the first quantity of detectably labeled NELP; and
    (v) comparing the detectably labeled NELP efflux value for the patient to a reference standard, wherein the reference standard is the detectably labeled NELP efflux value of control human body fluid sample(s) determined by carrying out (i)-(iv) using the control human body fluid sample(s) in place of the sample of body fluid from the patient;
    wherein a detectably labeled NELP efflux value for the patient that is equal to or higher than the reference standard is indicative of a lower risk for development of the disease in the patient,
    wherein a detectably labeled NELP efflux value for the patient that is lower than the reference standard is indicative of a higher risk for development of the disease in the patient,
    wherein the disease is an inflammatory disease or cardio-vascular disease.

2. The method of claim 1, wherein the disease is stroke, myocardial infarction, coronary artery disease (CAD), heart attack, arrhythmia, heart failure, congenital heart defects, cardiomyopathy, peripheral artery disease, angina, valve disease, high blood pressure, an inherited heart condition, or an inflammatory disease.

3. The method of claim 1,
    wherein a detectably labeled NELP efflux value for the patient that is equal to or higher than the reference standard is indicative of a lower non-calcified plaque burden in the patient, and
    wherein a detectably labeled NELP efflux value for the patient that is lower than the reference standard is indicative of a higher non-calcified plaque burden in the patient.

4. The method of claim 1,
    wherein a detectably labeled NELP efflux value for the patient that is equal to or higher than the reference standard is indicative of a lower total plaque burden in the patient, and
    wherein a detectably labeled NELP efflux value for the patient that is lower than the reference standard is indicative of a higher total plaque burden in the patient.

5. A method of lowering the risk for development of a disease in a patient, the method comprising:
    receiving an identification of the patient as having higher risk for development of the disease, wherein the risk for development of the disease has been assessed by the method of claim 1; and
    (i) administering one or both of a lipoprotein-modifying drug and an anti-inflammatory drug to the patient identified as having the higher risk for development of the disease and/or (ii) recommending lifestyle changes to the patient identified as having the higher risk for development of the disease,
    wherein the disease is an inflammatory disease or cardio-vascular disease.

6. The method of claim 1, wherein the lipid is a phosphatidylcholine.

7. The method of claim 1, wherein the donor particles comprise a lipid-binding particulate material.

8. The method of claim 1, further comprising applying a sterol to the donor particles prior to incubating the donor particles with the sample.

9. The method of claim 8, wherein the molar ratio of the lipid to the sterol on the donor particles is from 4:1 to 2:1.

10. The method of claim 8, wherein the sterol is cholesterol.

11. The method of claim 1, wherein the detectably labeled NELP comprises a hydrophilic portion, a hydrophobic portion, and a detectable label positioned on the hydrophilic portion.

12. The method of claim 1, comprising incubating the sample of body fluid from the patient with the donor particles at a temperature of from 10° C. to 90° C.

13. The method of claim 1, comprising incubating the sample of body fluid from the patient with the donor particles for a period of from 1 minute to 24 hours.

14. The method of claim 1, wherein separating the detectably labeled NELP-associated HDL into the first portion and the donor particles into the second portion comprises centrifuging the detectably labeled NELP-associated HDL and the donor particles.

15. The method of claim 14, wherein the first portion is a supernatant and the second portion is a pellet.

16. The method of claim 1, wherein separating the detectably labeled NELP-associated HDL into the first portion and the donor particles into the second portion comprises filtering the detectably labeled NELP-associated HDL from the donor particles.

17. The method of claim 1, wherein the method is carried out in less than two hours.

18. The method of claim 1, wherein the method is cell-free.

19. The method of claim 1, wherein the detectably labeled NELP comprises a radiolabel, a chemiluminescent label, or a fluorescent label.

20. The method of claim 1, wherein the lipid is 1,2-dimyristoyl-sn-glycero-3-phosphocholine (DMPC) or a lecithin.

21. The method of claim 1, wherein the sample of body fluid comprises whole plasma.

22. A method of measuring the quantity of functional high density lipoprotein (HDL) in a sample of body fluid from a patient, the method comprising:

(i) incubating a sample of body fluid from the patient with donor particles, wherein the sample of body fluid is whole plasma, urine, or saliva, and wherein the donor particles are coated with a lipid and a first quantity of detectably labeled, non-exchangeable lipid probe (NELP), which NELP is phosphatidylethanolamine (PE), prior to incubating the donor particles with the sample, wherein the detectably labeled NELP is effluxed by HDL, wherein the sample of body fluid comprises HDL and one or more HDL-associated protein(s) comprising apolipoprotein A-I (apoA-I), wherein the apoA-I specifically transfers at least a portion of the detectably labeled NELP from the donor particles to the HDL to produce detectably labeled NELP-associated HDL having a second quantity of detectably labeled NELP;

(ii) separating the detectably labeled NELP-associated HDL into a first portion and the donor particles into a second portion;

(iii) measuring the second quantity of detectably labeled NELP in the first portion; and (iv) determining a detectably labeled NELP efflux value for the patient, wherein the detectably labeled NELP efflux value for the patient equals the second quantity of detectably labeled NELP divided by the first quantity of detectably labeled NELP, wherein the detectably labeled NELP efflux value is indicative of the quantity of functional HDL in the sample of body fluid from the patient.

23. The method of claim 22, wherein the sample of body fluid comprises whole plasma.

* * * * *